(12) United States Patent
Weigel et al.

(10) Patent No.: US 7,507,556 B2
(45) Date of Patent: Mar. 24, 2009

(54) NUCLEIC ACIDS ENCODING RAT HYALURONAN RECEPTOR FOR ENDOCYTOSIS

(75) Inventors: Paul H. Weigel, Edmond, OK (US); Janet Weigel, Edmond, OK (US); Bin Zhou, Edmond, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 450 days.

(21) Appl. No.: 10/990,844

(22) Filed: Nov. 17, 2004

(65) Prior Publication Data

US 2005/0059118 A1 Mar. 17, 2005

Related U.S. Application Data

(62) Division of application No. 09/842,930, filed on Apr. 25, 2001, now Pat. No. 6,979,555.

(60) Provisional application No. 60/245,320, filed on Nov. 2, 2000, provisional application No. 60/199,538, filed on Apr. 25, 2000.

(51) Int. Cl.
*C07H 21/02* (2006.01)
*C07K 14/705* (2006.01)

(52) U.S. Cl. ............... 435/69.1; 435/252.3; 435/320.1; 536/23.5; 530/395; 530/350

(58) Field of Classification Search ........................ None
See application file for complete search history.

(56) References Cited

U.S. PATENT DOCUMENTS

| 5,206,353 | A |  | 4/1993 | Berger et al. |
| 5,284,999 | A |  | 2/1994 | Chin et al. |
| 5,696,237 | A |  | 12/1997 | Fitzgerald et al. |
| 6,060,037 | A |  | 5/2000 | Waldman |
| 7,153,670 | B2 | * | 12/2006 | Hastings et al. ............ 435/69.1 |

FOREIGN PATENT DOCUMENTS

WO WO94/01548 * 1/1994

OTHER PUBLICATIONS

Ohara et al., GENEMBL Locus AK024503, Sep. 29, 2000, accessed Jun. 19, 2002.*
Blum et al., GENEMBL Locus HSM801377, Feb. 18, 2000, accessed Jun. 19, 2002.*
Tao et al., GENEMBL Locus AF160476, Jul. 12, 2000, accessed Jun. 19, 2002.*
Marra et al., GenCOR Locus AA821602, Feb. 17, 1998, accessed Jun. 19, 2002.*
Bonaldo et al., GenCOR Locus BE656181, Sep. 6, 2000, accessed Jun. 19, 2002.*
Hillier et al., et al., GenCOR Locus T47504, Feb. 1, 1995, accessed Jun. 19, 2002.*
Hillier et al., GenCOR Locus T91781, Mar. 22, 1995, accessed Jun. 19, 2002.*
Raja et al, J. Biol. Chem. 263:16661 (1988).
McGary et al, Biochem. J. 257:875 (1989).
Forsberg and Gustafson, Biochim. Biophys. Acta, 1078:12 (1991).
Laurent and Fraser, FASEB J. 6:2397 (1992).
Yannariello-Brown et al, J. Biol. Chem 267:20451 (1992).
McGary et al, Hepatology, 18:1465 (1993).
DeBleser et al, Gut, 35:1509 (1994).
McCourt et al, J. Biol. Chem. 269:30081 (1994).
Fuxe et al., Evidence for receptors for hyaluronan in discrete nerve cell population of the brain, Brain Research, 1996, vol. 736, pp. 329-337, see entire document.
Yannariello-Brown et al, Glycobiol. 7:15 (1997).
McCourt and Gustafson, It. J. Biochem. Cell Biol. 29:1179 (1997).
Hayflick et al, Immunol. Res. 17:313 (1998).
McCourt et al, Hepatology 30:1276 (1999).
Zhou et al., Purification and subunit characterization of the rat liver endocytic hyaluronan receptor, J. Biol. Chem., Nov. 26, 1999, vol. 274, Issue 48, pp. 33831-33834, see entire document.
Weigel et al., "Glycans as Endocytosis Signals: the Cases of the Asialoglycoprotein and Hyaluronana/chondroitin Sulfate Receptors", Biochim. Biophys. Acta, vol. 1572(2-3):341-363, especially pp. 354-357 (2002).

* cited by examiner

*Primary Examiner*—Lorraine Spector
(74) *Attorney, Agent, or Firm*—Dunlap Codding, P.C.

(57) ABSTRACT

A purified nucleic acid segment encoding a functionally active hyaluronan receptor for endocytosis (HARE) or an active peptide fragment thereof, and methods for producing functionally active HARE or an active peptide fragment thereof therefrom, wherein the functionally active HARE or an active peptide fragment thereof is able to specifically bind HA, chondroitin and chondroitin sulfate.

18 Claims, 42 Drawing Sheets

(7 of 42 Drawing Sheet(s) Filed in Color)

Super-large HAR Complex

Antibody Inhibition of HA
Endocytosis by HARE in LECs

Antibody Inhibition of HA Binding to HARE on LECs is Temperature Dependent

Immunolocalization of HARE
in Bone Marrow

Control

Bars = 50 um

Figure 21

Figure 25
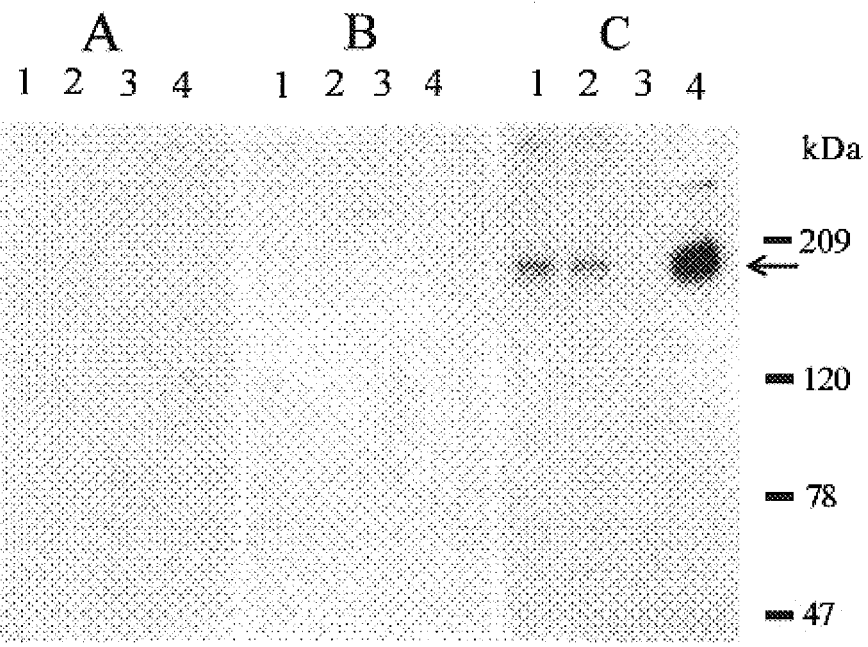
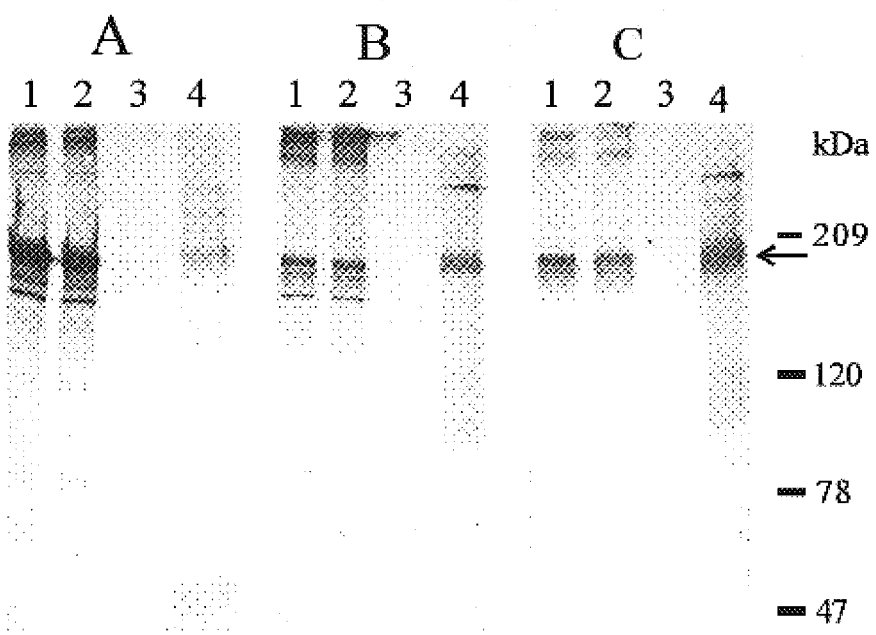

Degradation of internalized HA by transfected SK-Hep1 cell lines expressing the 175-kDa HARE Hyperosmolarity inhibits HA endocytosis mediated by HARE in transfected SK-Hep1 cells Specific monoclonal antibodies against HARE inhibit HA endocytosis in SK-Hep1 transfectants expressing the 175-kDa HARE

Amplification of the 1394 amino acid HARE Open Reading Frame from a human lymph node cDNA Library Schematic Organization of the Human HARE Gene on Chromosome 12
(encoding 1357 of the 1394 amino acids disclosed here)

NUCLEIC ACIDS ENCODING RAT HYALURONAN RECEPTOR FOR ENDOCYTOSIS

CROSS-REFERENCE TO RELATED APPLICATIONS

This application is a divisional of U.S. Ser. No. 09/842,930, filed Apr. 25, 2001, now U.S. Pat. No. 6,979,555 which claims the benefit of U.S. Provisional Application Serial No. 60/245,320, filed Nov. 2, 2000, and U.S. Provisional Application Serial No. 60/199,538, filed Apr. 25, 2000; the contents of each of which are hereby expressly incorporated herein by reference in their entirety.

FEDERALLY SPONSORED RESEARCH OR DEVELOPMENT

The government owns certain rights in the present invention pursuant to a grant from the National Institutes of Health (GM 35978).

BACKGROUND OF THE INVENTION

1. Field of the Invention

The present invention generally relates to a HA Receptor for Endocytosis, and more particularly, but not by way of limitation, to methods of purifying such HA Receptor for Endocytosis.

2. Brief Description of the Related Art

HA, also referred to herein as hyaluronic acid, or hyaluronan, is an important and often abundant extracellular matrix component of all tissues, in particular cartilage, skin and vitreous humor (Evered and Whelan, *The Biology of Hyaluronan*, Ciba Fnd. Symposium, 143:1 (1989)). HA plays a key role in development, morphogenesis and differentiation, in cell adhesion and proliferation, and in inflammation and wound healing (Evered and Whelan, *The Biology of Hyaluronan*, Ciba Fnd. Symposium, 143:1 (1989); Toole, *J. Intern. Med.* 242:35 (1997); Knudson and Knudson, *FASEB J.* 7:1233 (1993); Laurent and Fraser, *FASEB J.* 6:2397 (1992)). In humans, the total body turnover of HA is several grams per day (Evered and Whelan, *The Biology of Hyaluronan*, Ciba Fnd. Symposium, 143:1 (1989)). Although local turnover of HA occurs in avascular tissues, particularly cartilage (Hua et al, *J. Cell Sci.* 106:365 (1993); Aguiar et al, *Exp. Cell Res.* 252:292 (1999)), two major clearance systems are responsible for HA degradation and removal in the body (Laurent and Fraser, *FASEB J.* 6:2397 (1992)). The first is the lymphatic system, which accounts for about 85% of the HA turnover, and the second is in the liver, which accounts for the other approximately 15% of the total body HA turnover.

Throughout the body, HA is continuously synthesized and degraded in almost all tissues. At the same time, chondroitin sulfate and other glycosaminoglycans are also released from the cleavage of proteoglycans, especially aggregating proteoglycans associated with HA. Large native HA molecules (about $10^7$ Da) are partially degraded into large fragments (about $10^6$ Da) that are released from the matrix and enter the lymphatic system, thereafter flowing to lymph nodes.

The lymph nodes completely degrade the majority of HA (about 85%) by currently unknown mechanisms. Neither the responsible cell type, the receptor involved, nor the location in lymph nodes at which HA uptake and degradation occurs has been determined. The remaining HA (about 15%) that escapes degradation in the lymph nodes ultimately flows into the blood at the thoracic duct. Since HA is an exceptionally viscous polysaccharide in solution, it would be deleterious for the blood concentration of HA, even at relatively low molecular weight, to increase. Clearance of this circulating HA and the other glycosaminoglycan degradation fragments, such as chondroitin sulfate, is presumably important for normal health (Evered and Whelan, *The Biology of Hyaluronan*, Ciba Fnd. Symposium, 143:1 (1989); Laurent and Fraser, *FASEB J.* 6:2397 (1992)). Elevated serum HA levels are associated with a variety of diseases and pathological conditions such as liver cirrhosis, rheumatoid arthritis, psoriasis, scleroderma, fibromyalgia and some cancers (Yamad et al, *Acta Haematol.* 99:212 (1998); Lai et al, *J. Lab Clin. Med.* 131:354 (1998); Yaron et al, *J. Rheumatol.* 24:2221 (1997)).

Liver endothelial cells (LECs) in vertebrate liver express a very active, recycling endocytic receptor that removes these extracellular matrix-derived fragments of HA and other glycosaminoglycans, including chondroitin sulfate, from the blood (Laurent and Fraser, *FASEB J.* 6:2397 (1992); DeBleser et al, *Gut*, 35:1509 (1994); Raja et al, *J. Biol. Chem.* 263:16661 (1988); McGary et al, *Biochem. J.* 257:875 (1989); McGary et al, *Hepatology,* 18:1465 (1993)). ICAM-1, a 90 kDa protein also known as CD54 (Hayflick et al, *Immunol. Res.* 17:313 (1998)), was previously misidentified as the LEC HA Receptor for Endocytosis (HARE) (Forsberg and Gustafson, *Biochim. Biophys. Acta,* 1078:12 (1991); McCourt et al, *J. Biol. Chem.* 269:30081 (1994)). This research attempted to purify the HA receptor without the use of an assay to measure HA-binding activity. The claim that the HA Receptor for Endocytosis had been purified was subsequently acknowledged to be an artifact due to the nonspecific binding of ICAM-1 to the HA affinity resin (McCourt and Gustafson, *Int. J. Biochem. Cell Biol.* 29:1179 (1997); McCourt et al, *Hepatology* 30:1276 (1999)). In any case, since ICAM-1 is not a coated pit-targeted endocytic receptor, it is not the true HA receptor in LECs.

In addition to the normal turnover of HA in tissues throughout the body, a wide range of biomedical and clinical applications use exogenous HA that is also removed from the lymphatics or ultimately from the blood and degraded by the LEC HARE. For example, HA is used extensively in eye surgery, in the treatment of joint diseases including osteoarthritis, and is being developed as a drug delivery vehicle. Numerous studies have explored the benefit of HA during wound healing. The exogenous HA introduced in these various applications is naturally degraded by the lymph and LEC systems noted above. Despite the very large endocytic and degradative capacity of the LEC HARE and its importance in removing HA from the blood, prior to the present invention the HARE had not been successfully purified, molecularly cloned or expressed from a cDNA.

In two previous studies, one using a photoaffinity derivative of HA (Yannariello-Brown et al, *J. Biol. Chem.* 267: 20451 (1992)) and the other using a novel ligand blot assay with $^{125}$I-HA (Yannariello-Brown et al, *Glycobiol.* 7:15 (1997)), two specific HA-binding proteins in isolated rat LECs were identified at about 175 kDa and about 300 kDa. However, it was not until the present invention that the role of these two proteins in degradation of HA was determined.

SUMMARY OF THE INVENTION

The present invention is related to a functionally active Hyaluronan Receptor for Endocytosis (HARE) and active fragments thereof, wherein the HARE or active fragments thereof is able to specifically bind at least one of HA, chondroitin and chondroitin sulfate and endocytose the bound HA, chondroitin or chondroitin sulfate into a cell via a clathrin-coated pit pathway. Broadly, the present invention includes purified nucleic acid segments encoding a functionally active HARE and active peptide fragments thereof, as well as a purified, functionally active HARE protein and purified active peptide fragments thereof. Active peptide fragments of HARE include a soluble fragment of the HARE protein, such as an extracellular domain of HARE, as well as a peptide containing an HA-binding domain of HARE, wherein such active peptide fragments of HARE retain the ability to specifically bind at least one of HA, chondroitin and chondroitin sulfate. The invention also encompasses complementary nucleic acid sequences to the nucleic acid sequences encoding a functionally active HARE and active peptide fragments thereof, nucleic acid sequences which will hybridize to the nucleic acid sequences encoding a functionally active HARE or active peptide fragments thereof or such complementary sequence, nucleic acid sequences which but for the degeneracy of the genetic code, or encoding of functionally equivalent amino acids, would hybridize to the nucleic acid sequence encoding a functionally active HARE or active peptide fragments thereof or the complementary sequence thereof, and primers which will hybridize to and amplify a nucleic acid sequence encoding a functionally active HARE or active peptide fragments thereof.

In one embodiment, the present invention includes a method of making an antibody, such as a monoclonal antibody, by immunizing a non-human animal with an immunogenic fragment of HARE. The immunogenic fragment may comprise a sequence in accordance with at least a portion of SEQ ID NO:2 or SEQ ID NO:25. In preferred embodiments, the immunogenic fragment comprises an HA-binding domain of HARE. The method of making an antibody may further include identifying a hybridoma cell producing a monoclonal antibody specific for HARE, and culturing such hybridoma cell under conditions that permit production of the monoclonal antibody. Such method may further include isolating the monoclonal antibody from the hybridoma cell. The antibody will selectively bind an epitope of HARE, and in a preferred embodiment, the antibody will also inhibit binding of at least one of HA, chondroitin and chondroitin sulfate to HARE. Such antibody would be useful not only in vitro for purification of functionally active HARE from various biological samples such as liver, spleen, lymph nodes and bone marrow, such as with the use of an affinity matrix comprising the antibody bound to a solid support, but would also be useful in vivo, wherein the antibody could be "humanized" such that administration of the antibody to a human would not result in an immune response to the antibody molecule itself and could be utilized in methods of treatment for certain diseases and disorders. The method of "humanizing" an antibody involves removing portions of the antibody which my be antigenic in a human and substituting like portions of a human antibody therefor.

The present invention also encompasses a recombinant vector, such as a plasmid, cosmid, phage or virus vector, which comprises a purified nucleic acid segment having a coding region encoding a functionally active HARE, such as a nucleotide sequence in accordance with SEQ ID NO:1 or SEQ ID NO:24. The recombinant vector may be an expression vector and have a promoter operatively linked to the HARE coding region. A host cell, such as a eucaryotic cell, may be transfected, electroporated or transduced with such recombinant vector to produce a recombinant host cell expressing functionally active HARE. In a preferred embodiment, the purified nucleic acid segment encoding a functionally active HARE is integrated into a chromosome of the recombinant host cell. The recombinant host cell containing the recombinant vector having a coding region encoding a functionally active HARE may produce a functionally active HARE which binds and endocytoses at least one of HA, chondroitin and chondroitin sulfate. Such recombinant host cell may be utilized in a method of purifying HARE, by culturing the recombinant host cell under conditions that allow for expression of functionally active HARE from the recombinant DNA segment, then separating and purifying the functionally active HARE from the recombinant host cell.

In another embodiment of the present invention, a method of identifying compounds which inhibit binding of at least one of HA, chondroitin and chondroitin sulfate to HARE is provided. The method includes providing a purified fragment of HARE capable of binding at least one of HA, chondroitin and chondroitin sulfate, forming a first affinity matrix comprising the purified fragment of HARE bound to a solid support, contacting a test compound with the first affinity matrix to form a treated affinity matrix, contacting at least one of HA, chondroitin and chondroitin sulfate with the first affinity matrix and contacting HA with the treated affinity matrix, and determining that the test compound inhibits binding of at least one of HA, chondroitin and chondroitin sulfate to HARE when at least one of HA, chondroitin and chondroitin sulfate binds to a greater extent to the first affinity matrix than to the treated affinity matrix. The purified fragment of HARE may be a soluble fragment of HARE, such as an extracellular domain of HARE or an HA-binding domain of HARE.

In yet another embodiment of the present invention, a method of treating a liquid solution containing at least one of HA, chondroitin and chondroitin sulfate is provided. Such method includes providing an affinity matrix comprising a functionally active fragment of HARE, as described herein above, bound to a solid support, and exposing a quantity of the liquid solution to the affinity matrix wherein at least one of HA, chondroitin and chondroitin sulfate contained in the liquid solution is removed therefrom. Such liquid solution may be blood or plasma, such as when blood or plasma is removed from a dialysis patient and filtered to remove contaminants and waste.

Other objects, features and advantages of the present invention will become apparent from the following detailed description when read in conjunction with the accompanying figures and appended claims.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 21. Nucleic acid (SEQ ID NO:1) and deduced amino acid (SEQ ID NO:2) sequences of the 4.7-kb cDNA encoding the rat 175 kDa HARE. The artificial cDNA containing 4708 nucleotides encodes a 1431 amino acid recombinant 175 kDa HARE protein, whose deduced amino acid sequence begins with a serine. Amino acid sequences verified by peptide sequence analysis of the purified HARE are underlined and the two N-terminal peptides found in the purified protein are underlined and in italics. Putative N-glycosylation sites are in boldface and in italics. Cys residues are highlighted in boldface and italics. The predicted transmembrane domain of the type I membrane protein is underlined and in boldface. The three shaded regions in the cytoplasmic domain are potential motifs for targeting the receptor to clathrin-coated pits.

FIG. 25. Western blot and $^{125}$I-HA ligand blot analysis of recombinant 175 kDa HARE expression in COS 7 cells. COS 7 cells were transfected with two different clones containing the 175 kDa HARE cDNA (lanes 1 and 2) fused at its 5' end with the Ig k-light chain leader sequence. Lane 3 is untransfected COS 7 cells and lane 4 is a positive control containing rat LEC extract. Expression of the 175 kDa HARE was analyzed by SDS-PAGE of cells extracts with (A) and without (B and C) reduction followed by transfer to nitrocellulose. The blots were incubated with 2 µg/ml $^{125}$I-HA with (B) or without (A and C) excess unlabeled HA (300 µg/ml) to assess nonspecific and total binding, respectively. After ligand blotting (top panel), the membrane was subjected to Western analysis (lower panel) as described in Materials and Methods.

FIG. 28. Alignment of the rat 175 kDa HARE deduced amino acid sequence with a family of hypothetical protein sequences of unknown function. Sequences were aligned with DNAsis (Version 2.50), saved as a text file and edited in Microsoft Word. The hypothetical protein sequences, all of which are human, are designated by their GenBank protein accession numbers. Our deposited sequences for the rat 175 kDa HARE (rHARE) are under accession numbers AY007370 and AAG13634 for the nucleic acid (SEQ ID NO:1) and protein (SEQ ID NO:2) sequences, respectively. The recombinant 175 kDa HARE that was constructed in order to demonstrate the functionality of this receptor starts with serine (arrow). Residues in HARE identical to two or more of the other sequences are shaded in yellow. Conserved cysteine residues are in boldface and shaded red. The residues under the solid bold line are identified as an extracellular Link domain (Xlink), a putative HA-binding domain. The dashed line is above the approximate boundaries of a single putative transmembrane domain in each protein. Regions within boxes denote candidate φXXB motifs for targeting to coated pits.

FIG. 33. Nucleic acid (SEQ ID NO:24) and deduced protein (SEQ ID NO:25) sequences of the human 190 kDa HARE. The HARE nucleotide sequence was assembled based on the sequences of BAB15793 and specific RT-PCR products derived from human spleen (Table III). The solid bars underline 17 consensus N-glycosylation sites. The arrow indicates a nucleotide sequence error in BAB15793 (omission of an A, in boldface) that results in a frame-shift, which adds 210 amino acids (in italics) and deletes eight at the N-terminal end of the ORF derived from BAB15793. A second error in the BAB15793 nucleotide sequence at T$^{1386}$ (rather than C) and noted in boldface is silent. Amino acid sequences within solid or dashed boxes indicate the peptides of the authentic human 190 kDa HARE (immunoaffinity purified from human spleen) that were identified, respectively, by direct sequencing (Table IV) or by molecular mass analysis (Table V). Human spleen HARE amino acid sequences that were not in the BAB15793 protein sequence but were confirmed in RT-PCR products are boxed and underlined.

FIG. 35. Sequence alignment of the human (SEQ ID NO:25) and rat (SEQ ID NO:2) HARE proteins. Sequences for the two smaller HARE proteins were aligned using SIM (at www.ExPASy) and then saved as a Microsoft Word file for highlighting and annotation. Identical residues found in both sequences are shaded in yellow. Conserved consensus N-linked glycosylation sides are in boldface and highlighted in gray. Solid black bars indicate potential —N—X-Cys-glycosylation sites, two of which are conserved. Cysteine residues are boldface and shaded red where identical between the two proteins. The arrow denotes the beginning of the least conserved regions of the two proteins; their cytoplasmic domains. The residues under the solid blue line are identified as an extracellular Link domain (Xlink), a putative hyaluronan-binding domain. The residues under the dashed blue line indicate the single predicted transmembrane domains. The three conserved candidate φXXB motifs are within the two blue boxes. Ser, Thr or Tyr residues that are predicted (by NetPhos 2.0; Blom et al, *J. Molec. Biol.* 294:1351 (1999)) to be phosphorylated are shown in boldface white with red highlighting. Our deposited sequence for the rat 175 kDa HARE is under accession numbers AY007370 and AAG13634 for the nucleic acid (SEQ ID NO:1) and protein (SEQ ID NO:2) sequences, respectively.

for 10 min—5 cycles; 94° C. for 20 sec, 60° C. for 10 min—25 cycles. The PCR reaction mixtures were electrophoresed in a 1% agarose gel and visualized by staining with ethidium bromide. The molecular weight (MW) markers used were the kb markers from Life Technologies.

Figure 38:
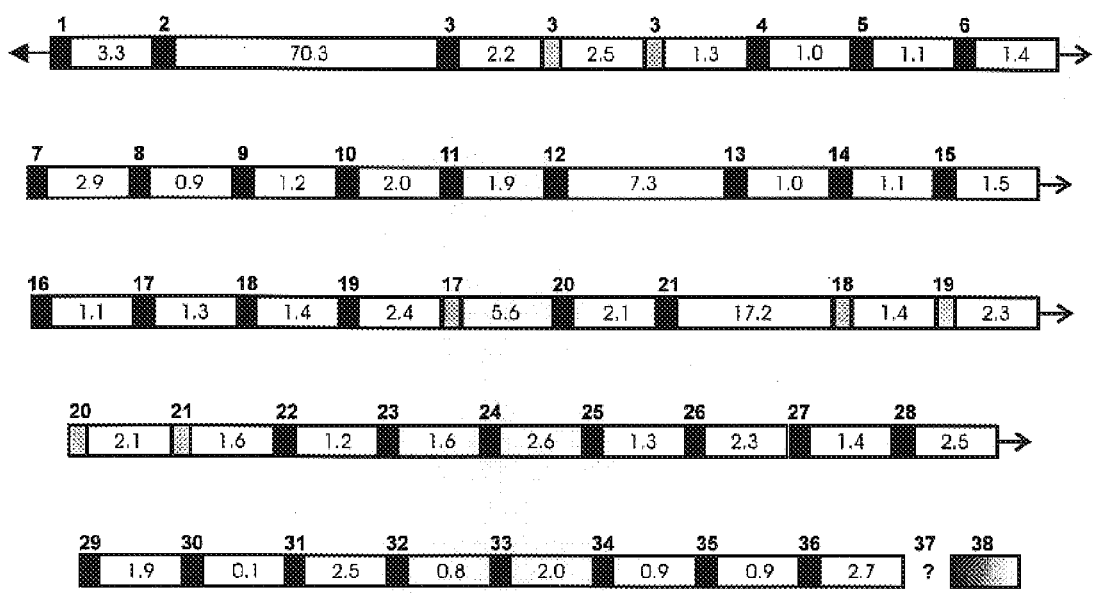

FIG. 38. Schematic organization of the human HARE gene on chromosome 12.

Figure 39:
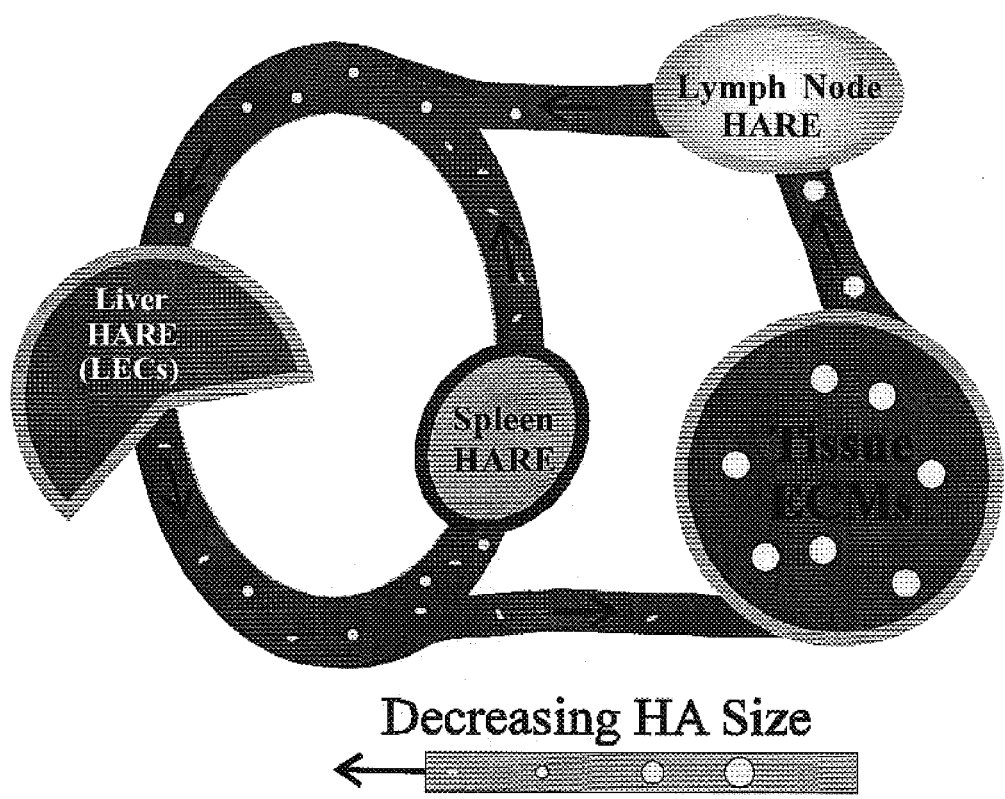

FIG. 39. Scheme for HA turnover and metabolism in humans. The scheme depicts the overall turnover of HA present initially in the ECM of tissues throughout the body. Partially degraded HA is flushed from the ECM into lymph by the flow of fluid through the tissue. Some HA may be degraded locally in the tissue, but most is delivered to and removed by lymph nodes. The remaining HA enters the blood and ≧85% is cleared by the liver; the spleen removes ~10%. HARE, which is expressed on the surface of sinusoidal endothelial cells of lymph node and liver, binds the circulating HA and removes it from the lymph or blood by internalization through the clathrin coated pit endocytic pathway. The average size and concentration of the HA decreases in going from ECM to lymph node to blood (Laurent and Fraser, *FASEB J.* 6:2397 (1992); Laurent and Fraser, *Degradation of Bioactive Substances: Physiology and Pathophysiology,* 249, CRC Press, Boca Raton, Fla. (1991); Tengblad et al, *Biochem. J.* 236:521 (1986)).

DETAILED DESCRIPTION OF THE INVENTION

Before explaining at least one embodiment of the invention in detail, it is to be understood that the invention is not limited in its application to the details of construction and the arrangement of the components or steps or methodologies set forth in the following description or illustrated in the drawings. The invention is capable of other embodiments or of being practiced or carried out in various ways. Also, it is to be understood that the phraseology and terminology employed herein is for the purpose of description and should not be regarded as limiting.

One embodiment of the present invention envisions a purified mammalian HARE or an active fragment thereof, comprising a polypeptide which is able to specifically bind at least one of HA, chondroitin and chondroitin sulfate. Such purified mammalian HARE may be a protein having a molecular weight in a range of from about 175 kDa to about 190 kDa, and may comprise a sequence in accordance with at least one of SEQ ID NO:2 and SEQ ID NO:25. Alternatively, the purified mammalian HARE may be a protein having a molecular weight in a range of from about 300 kDa to about 315 kDa, wherein the protein may comprise at least two disulfide-bonded subunits. Further, the purified mammalian HARE may be a protein having at least 40% to at least 90% sequence identity to one of SEQ ID NO:2 and SEQ ID NO:25. The purified mammalian HARE fragment may comprise a soluble fragment of HARE, such as an extracellular domain of HARE, or an HA-binding domain of HARE.

The present invention further includes a purified composition comprising a functionally active HARE polypeptide or an active polypeptide fragment thereof, wherein the functionally active HARE or the active polypeptide fragment thereof is able to specifically bind at least one of HA, chondroitin and chondroitin sulfate. Such polypeptides may have an amino acid sequence selected from the group consisting of at least a portion of the sequence in accordance with SEQ ID NO:2 and at least a portion of the sequence in accordance with SEQ ID NO:25. When the purified composition is an active polypeptide fragment of HARE, the active polypeptide fragment may be a soluble fragment of HARE, such as an extracellular domain of HARE or an HA-binding domain of HARE.

The term "functionally active HARE" as used herein will be understood to include a protein or peptide which is able to specifically bind at least one of HA, chondroitin and chondroitin sulfate, and when present on a surface of a cell, is able to endocytose the bound HA, chondroitin or chondroitin sulfate. The term "active peptide fragment of HARE" as used herein will be understood to include polypeptides which are able to specifically bind at least one of HA, chondroitin and chondroitin sulfate. Such active peptide fragments of HARE may include soluble fragments of HARE. One of ordinary skill in the art, given this Specification containing descriptions of the cytoplasmic, transmembrane and extracellular domains of HARE (as discussed in more detail herein below in the Example), should be able to identify and select portions of the HARE protein (e.g., the extracellular domain of HARE or portions thereof, such as an HA-binding domain of HARE) which retain the ability to bind at least one of HA, chondroitin and chondroitin sulfate.

As used herein, the terms ™nucleic acid segments™, "DNA sequence", ™DNA segment™ and "nucleic acid sequences" are used interchangeably and refer to a DNA molecule which has been isolated free of total genomic DNA of a particular species. Therefore, a ™purified™ DNA or nucleic acid segment as used herein refers to a DNA segment which contains a HA Receptor for Endocytosis (™HARE™) coding sequence or fragment thereof yet is isolated away from, or purified free from, unrelated genomic DNA, for example, mammalian host genomic DNA. Included within the term ™DNA segment™, are DNA segments and smaller fragments of such segments, and also recombinant vectors, including, for example, plasmids, cosmids, phage, viruses, and the like.

Similarly, a DNA segment comprising an isolated or purified HARE gene refers to a DNA segment including HARE coding sequences isolated substantially away from other naturally occurring genes or protein encoding sequences. In this respect, the term ™gene™ is used for simplicity to refer to a functional protein, polypeptide or peptide encoding unit. As will be understood by those skilled in the art, this functional term includes genomic sequences, cDNA sequences or combinations thereof. ™Isolated substantially away from other coding sequence™ means that the gene of interest, in this case HARE or a fragment thereof, forms the significant part of the coding region of the DNA segment, and that the DNA segment does not contain large portions of naturally-occurring coding DNA, such as large chromosomal fragments or other functional genes or DNA coding regions. Of course, this refers to the DNA segment as originally isolated, and does not exclude genes or coding regions later added to, or intentionally left in the segment by the hand of man.

Preferably, DNA sequences in accordance with the present invention will further include genetic control regions which allow for the expression of the sequence in a selected recombinant host. Of course, the nature of the control region employed will generally vary depending on the particular use (e.g., cloning host) envisioned. One of ordinary skill in the art, given this Specification, would be able to identify and select genetic control regions which can be utilized in accordance with the present invention to enhance expression of a HARE gene. Examples of specific genetic control regions which may be utilized are described in more detail herein below with regard to specific recombinant host cells.

In particular embodiments, the invention concerns isolated DNA segments and recombinant vectors incorporating DNA sequences which encode a HARE gene or a fragment thereof, that includes within its amino acid sequence an amino acid sequence in accordance with at least a portion of SEQ ID NO:2 or SEQ ID NO:25. Moreover, in other particular embodiments, the invention concerns isolated DNA segments and recombinant vectors incorporating DNA sequences which encode a gene that includes within its DNA sequence the DNA sequence of a HARE gene or DNA or fragment thereof, and in particular to a HARE gene or cDNA or fragment thereof, corresponding to rat liver or human spleen HARE. For example, where the DNA segment or vector encodes a full length HARE protein, or is intended for use in expressing the HARE protein, preferred sequences are those which are essentially as set forth in SEQ ID NO:2 or SEQ ID NO:25. In an alternative embodiment, where the DNA segment may encode a functional portion of the HARE protein, such as a soluble form of the protein which still retains the ability to bind at least one of HA, chondroitin and chondroitin sulfate, for example a peptide containing an extracellular domain of HARE or an HA-binding domain of HARE, preferred sequences are at least a portion of those which are essentially as set forth in SEQ ID NO:2 or SEQ ID NO:25. It is within the abilities of one of ordinary skill in the art, given this Specification, to identify the DNA segments encoding the cytoplasmic, transmembrane and extracellular domains of the HARE protein and to locate and select the portions of the amino acid sequences of SEQ ID NO:2 or SEQ ID NO:25 which encode the extracellular domain of HARE, or a portion thereof, and not the cytoplasmic or transmembrane domain of HARE.

Nucleic acid segments having functional HARE activity may be isolated by the methods described herein. The term ™a sequence essentially as set forth in SEQ ID NO:2™ or "a sequence essentially as set forth in SEQ ID NO:25™ means that the sequence substantially corresponds to at least a portion of SEQ ID NO:2 or SEQ ID NO:25, respectively, and has relatively few amino acids which are not identical to, or a biologically functional equivalent of, the amino acids of SEQ ID NO:2 or SEQ ID NO:25, respectively. The term ™biologically functional equivalent™ is well understood in the art and is further defined in detail herein as a gene having a sequence essentially as set forth in SEQ ID NO:2 or SEQ ID NO:25, and that is associated with the ability to bind and endocytose at least one of HA, chondroitin and chondroitin sulfate.

One of ordinary skill in the art would appreciate that a nucleic acid segment encoding a functionally active HARE may contain conserved or semi-conserved amino acid substitutions to the sequences set forth in SEQ ID NO:2 and SEQ ID NO:25 and yet still be within the scope of the invention.

In particular, the art is replete with examples of practitioners ability to make structural changes to a nucleic acid segment (i.e. encoding conserved or semi-conserved amino acid substitutions) and still preserve its enzymatic or functional activity. See for example: (1) Risler et al. "Amino Acid Substitutions in Structurally Related Proteins. A Pattern Recognition Approach." *J. Mol. Biol.* 204:1019-1029 (1988) [". . . according to the observed exchangeability of amino acid side chains, only four groups could be delineated; (i) Ile and Val; (ii) Leu and Met, (iii) Lys, Arg, and Gln, and (iv) Tyr and Phe."]; (2) Niefind et al. "Amino Acid Similarity Coefficients for Protein Modeling and Sequence Alignment Derived from Main-Chain Folding Anoles." *J. Mol. Biol.* 219:481-497 (1991) [similarity parameters allow amino acid substitutions to be designed]; and (3) Overington et al. "Environment-Specific Amino Acid Substitution Tables: Tertiary Templates and Prediction of Protein Folds," *Protein Science* 1:216-226 (1992) ["Analysis of the pattern of observed substitutions as a function of local environment shows that there are distinct patterns . . . " Compatible changes can be made.] Standardized and accepted functionally equivalent amino acid substitutions are presented in Table I.

These references and countless others indicate that one of ordinary skill in the art, given a nucleic acid sequence, could make substitutions and changes to the nucleic acid sequence without changing its functionality. Also, a substituted nucleic acid segment may be highly similar and retain its functional activity with regard to its unadulterated parent, and yet still fail to hybridize thereto under standard stringent hybridization conditions. However, while hybridization may not occur at such stringent hybridization conditions, hybridization may be observed at less stringent, relaxed hybridization conditions. Stringent and relaxed hybridization conditions are discussed in more detail herein below.

TABLE I

| Amino Acid Group | Conservative and Semi-Conservative Substitutions |
| --- | --- |
| NonPolar R Groups | Alanine, Valine, Leucine, Isoleucine, Proline, Methionine, Phenylalanine, Tryptophan |
| Polar, but uncharged, R Groups | Glycine, Serine, Threonine, Cysteine, Asparagine, Glutamine |
| Negatively Charged R Groups | Aspartic Acid, Glutamic Acid |
| Positively Charged R Groups | Lysine, Arginine, Histidine |

Another preferred embodiment of the present invention is a purified nucleic acid segment that encodes a protein in accordance with SEQ ID NO:2 or SEQ ID NO:25, further defined as a recombinant vector. As used herein, the term ™recombinant vector™ refers to a vector that has been modified to contain a nucleic acid segment that encodes a HARE protein, or fragment thereof, such as a soluble form of the protein or an HA-binding domain of the protein. The recombinant vector may be further defined as an expression vector comprising a promoter operatively linked to said HARE encoding nucleic acid segment.

Yet another preferred embodiment of the present invention is a purified nucleic acid segment that encodes an active portion of the protein in accordance with a portion of SEQ ID NO:2 or SEQ ID NO:25. For example, the invention also includes a purified nucleic acid segment encoding a soluble form of the protein, such as a portion of the protein containing the extracellular domain but not the cytoplasmic or transmembrane domains of the protein, which retains the ability to bind at least one of HA, chondroitin and chondroitin sulfate, or a portion of the protein containing an active HA-binding domain of HARE.

A further preferred embodiment of the present invention is a host cell, made recombinant with a recombinant vector comprising a HARE gene. In a preferred embodiment, the recombinant host cell is a eukaryotic cell. As used herein, the term ™engineered™ or ™recombinant™ cell is intended to refer to a cell into which a recombinant gene, such as a gene encoding HARE, has been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a cDNA gene, a copy of a genomic gene, or will include genes positioned adjacent to a promoter not naturally associated with the particular introduced gene. In a preferred embodiment, the recombinantly introduced gene may be integrated into the genome of the host cell.

Where one desires to use a eucaryotic host system, such as yeast or Chinese hamster ovary, African green monkey kidney cells, VERO cells, or the like, it will generally be desirable to bring the HARE gene under the control of sequences which are functional in the selected alternative host. In another alternative, the vector may contain a cassette which signals for the sequence to be integrated into the chromosome. The appropriate DNA control sequences, as well as their construction and use, are generally well known in the art as discussed in more detail herein below.

In preferred embodiments, the HARE-encoding DNA segments further include DNA sequences, known in the art functionally as origins of replication or ™replicons™, which allow replication of contiguous sequences by the particular host. Such origins allow the preparation of extrachromosomally localized and replicating chimeric segments or plasmids, to which HARE DNA sequences are ligated. In one instance, the employed origin is one capable of replication in bacterial hosts suitable for biotechnology applications. However, for more versatility of cloned DNA segments, it may be desirable to alternatively or even additionally employ origins recognized by other host systems whose use is contemplated (such as in a shuttle vector).

The isolation and use of other replication origins such as the SV40, polyoma or bovine papilloma virus origins, which may be employed for cloning or expression in a number of higher organisms, are well known to those of ordinary skill in the art. In certain embodiments, the invention may thus be defined in terms of a recombinant transformation vector which includes the HARE coding gene sequence together with an appropriate replication origin and under the control of selected control regions.

Thus, it will be appreciated by those of skill in the art that other methods may be used to obtain the HARE gene or cDNA, in light of the present disclosure. For example, polymerase chain reaction or RT-PCR produced DNA fragments may be obtained which contain full complements of genes or cDNAs from a number of sources, including other eukaryotic sources, such as cDNA libraries. Virtually any molecular cloning approach may be employed for the generation of DNA fragments in accordance with the present invention. Thus, the only limitation generally on the particular method employed for DNA isolation is that the isolated nucleic acids should encode a biologically functional equivalent HARE.

Once the DNA has been isolated, it is ligated together with a selected vector. Virtually any cloning vector can be employed to realize advantages in accordance with the invention. Typical useful vectors include plasmids, cosmids, phages and viral vectors for use in prokaryotic or eukaryotic organisms. Examples include pKK223-3, pSA3, pcDNA3.1, recombinant lambda, SV40, polyoma, adenovirus, bovine papilloma virus and retroviruses.

One procedure that would further augment HARE gene copy number is the insertion of multiple copies of the gene into the vector. Another technique would include integrating the HARE gene or multiple copies thereof into chromosomal DNA.

Where a eukaryotic source such as tissues rich in sinusoidal cells of the reticuloendothelial system such as liver, spleen, lymph node and bone marrow is employed, one will desire to proceed initially by preparing a cDNA library. This is carried out first by isolation of mRNA from the above cells, followed by preparation of double stranded cDNA using an enzyme with reverse transcriptase activity and ligation with the selected vector. Numerous possibilities are available and known in the art for the preparation of the double stranded cDNA, and all such techniques are believed to be applicable.

A preferred technique involves reverse transcription. Once a population of double stranded cDNAs is obtained, a cDNA library is prepared in the selected host by accepted techniques, such as by ligation into the appropriate vector and amplification in the appropriate host. Due to the high number of clones that are obtained, and the relative ease of screening large numbers of clones by the techniques set forth herein, one may desire to employ phage expression vectors, such as λgt11, λgt12, λGem11, and/or λZAP for the cloning and expression screening of cDNA clones.

In certain other embodiments, the invention concerns isolated DNA segments and recombinant vectors that include within their sequence a nucleic acid sequence essentially as set forth in SEQ ID NO:1 or SEQ ID NO:24. The term ™essentially as set forth in SEQ ID NO:1™ or ™essentially as set forth in SEQ ID NO:24™ is used in the same sense as described above and means that the nucleic acid sequence substantially corresponds to a portion of SEQ ID NO:1 or SEQ ID NO:24, respectively, and has relatively few codons which are not identical, or functionally equivalent, to the codons of SEQ ID NO:1 or SEQ ID NO:24, respectively. The term ™functionally equivalent codon™ is used herein to refer to codons that encode the same amino acid, such as the six codons for arginine or serine, as set forth in Table I, and also refers to codons that encode biologically equivalent amino acids.

It will also be understood that amino acid and nucleic acid sequences may include additional residues, such as additional N— or C-terminal amino acids or 5' or 3' nucleic acid sequences, and yet still be essentially as set forth in one of the sequences disclosed herein, so long as the sequence meets the criteria set forth above, including the maintenance of biological protein activity where protein expression and receptor activity (i.e., HA, chondroitin or chondroitin sulfate binding) is concerned. The addition of terminal sequences particularly applies to nucleic acid sequences which may, for example, include various non-coding sequences flanking either of the 5' or 3' portions of the coding region or may include various internal sequences, which are known to occur within genes.

Allowing for the degeneracy of the genetic code as well as conserved and semi-conserved substitutions, sequences which have between about 40% and about 80%; or more preferably, between about 80% and about 90%; or even more preferably, between about 90% and about 99%; of nucleotides which are identical to the nucleotides of SEQ ID NO:1 or SEQ ID NO:24 will be sequences which are ™essentially as set forth in SEQ ID NO:1™ or ™essentially as set forth in SEQ ID NO:24™, respectively. Sequences which are essentially the same as those set forth in SEQ ID NO:1 or SEQ ID NO:24, respectively, may also be functionally defined as sequences which are capable of hybridizing to a nucleic acid segment containing the complement of SEQ ID NO:1 under stringent or relaxed hybridizing conditions. Suitable standard hybridization conditions will be well known to those of skill in the art and are clearly set forth herein.

The term ™standard hybridization conditions™ as used herein is used to describe those conditions under which substantially complementary nucleic acid segments will form standard Watson-Crick base-pairing. A number of factors are known that determine the specificity of binding or hybridization, such as pH, temperature, salt concentration, the presence of agents, such as formamide and dimethyl sulfoxide, the length of the segments that are hybridizing, and the like. When it is contemplated that shorter nucleic acid segments will be used for hybridization, for example fragments between about 14 and about 100 nucleotides, salt and temperature preferred conditions for hybridization will include 1.2-1.8×HPB at 40-50° C. When it is contemplated that longer nucleic acid segments will be used for hybridization, for example fragments greater than 100 nucleotides, salt and temperature preferred conditions for hybridization will include 1.2-1.8×HPB at 60-70° C.

The term "standard hybridization conditions" includes stringent hybridization conditions as well as relaxed hybridization conditions. In general, when the temperature is increased and salt concentration (ionic strength) is decreased in the wash, the conditions become more stringent; these conditions favor hybrid interactions that have a higher degree of complementarity. When the annealing and wash conditions are at lower temperature and higher ionic strength, less complementary hybrids, which might not be present under more stringent conditions, can be stabilized. For example, to screen the λ-ZAP EXPRESS™ rat LECs cDNA library relatively high-stringency conditions (60° C. overnight in QUIKHYB™ hybridization solution followed by two washes for 15 minutes each at room temperature with 2×SSC, 0.1% SDS and two washes for 30 minutes each at 50° C. with 0.1×SSC, 0.1% SDS) were used. However, less stringent hybridization conditions were used to screen a genomic DNA library that was expected to contain numerous exons separated by noncomplementary introns (40° C. overnight in QUIKHYB™ hybridization solution, two washes for 15 minutes each at room temperature with 2×SSC, 0.1% SDS and one wash for 30 minutes at 40° C. with 0.1×SSC-0.1% SDS).

Naturally, the present invention also encompasses DNA segments which are complementary, or essentially complementary, to the sequence set forth in SEQ ID NO:1 or SEQ ID NO:24. Nucleic acid sequences which are ™complementary™ are those which are capable of base-pairing according to the standard Watson-Crick complementarity rules. As used herein, the term ™complementary sequences™ means nucleic acid sequences which are substantially complementary, as may be assessed by the same nucleotide comparison set forth above, or as defined as being capable of hybridizing to the nucleic acid segment of SEQ ID NO:1 or SEQ ID NO:24.

The present invention also includes primers which may be utilized to amplify the coding region of HARE or portions thereof. For example, purified nucleic acid segments according to SEQ ID NO:3 and SEQ ID NO:4 (Table II) are capable of hybridizing to SEQ ID NO:1, while purified nucleic acid segments according to SEQ ID NO:5 and SEQ ID NO:6 (Table III) are capable of hybridizing to SEQ ID NO:24. Other primers which may be utilized in accordance with the present invention are listed in Tables II and III. However, it is to be understood that the present invention is not limited to such primers, and a person of ordinary skill in the art, given this Specification, will be able to identify and select primers which can be utilized to amplify the coding region of HARE, or a portion thereof, such as an extracellular domain or an HA-binding domain of HARE. The present invention also includes primers which are engineered to introduce a restriction site into a DNA sequence to aid in cloning of such DNA sequence. Examples include SEQ ID NO:21, SEQ ID NO:22 and SEQ ID NO:23. However, it is within the skill of one in the art to create restriction sites in a DNA segment which aid in ligation of such DNA segment to a vector having a particular cloning site consisting of a set of restriction sites, and therefore, the present invention is not limited to the primers listed herein.

The nucleic acid segments of the present invention, regardless of the length of the coding sequence itself, may be combined with other DNA sequences, such as promoters, polyadenylation signals, additional restriction enzyme sites, multiple cloning sites, epitope tags, poly histidine regions, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

Naturally, it will also be understood that this invention is not limited to the particular nucleic acid sequences of SEQ ID NO:1 and SEQ ID NO:24 and amino acid sequences of SEQ ID NO:2 and SEQ ID NO:25. Recombinant vectors and isolated DNA segments may therefore variously include the HARE coding regions themselves, coding regions bearing, selected alterations or modifications in the basic coding region, or they may encode larger polypeptides which nevertheless include HARE-coding regions or may encode biologically functional equivalent or precursor proteins or peptides which have variant amino acids sequences.

The DNA segments of the present invention encompass biologically functional equivalent HARE proteins and peptides. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the functional activity or to antigenicity of the HARE protein.

A preferred embodiment of the present invention is a purified composition comprising a polypeptide having an amino acid sequence in accordance with SEQ ID NO:2 or an amino acid sequence in accordance with SEQ ID NO:25. The term "purified" as used herein, is intended to refer to a HARE protein composition, wherein the HARE protein or appropriately modified HARE protein (e.g. containing a $[HIS]_6$ tail) is purified to any degree relative to its naturally-obtainable state. The invention also includes a purified composition comprising a polypeptide having an amino acid sequence in accordance with a portion of SEQ ID NO:2 or SEQ ID NO:25 wherein the polypeptide is capable of selectively binding at least one of HA, chondroitin and chondroitin sulfate. The ligand blot assay described herein below and utilized herein may be utilized to assay for such an HA-binding domain of HARE.

Turning to the expression of the HARE gene whether from genomic DNA, or a cDNA, one may proceed to prepare an expression system for the recombinant preparation of the HARE protein. The engineering of DNA segment(s) for expression in a eukaryotic system may be performed by techniques generally known to those of skill in recombinant expression.

Another embodiment of the present invention is a method of preparing a protein composition comprising growing a recombinant host cell comprising a vector that encodes a protein which includes an amino acid sequence in accordance with SEQ ID NO:2 or SEQ ID NO:25 or an amino acid sequence which is functionally similar with conserved or semi-conserved amino acid changes. The host cell will be grown under conditions permitting nucleic acid expression and protein production followed by recovery of the protein so produced. The production of HARE, including the host cell, conditions permitting nucleic acid expression, protein production and recovery will be known to those of skill in the art in light of the present disclosure of the HARE gene, and the HARE gene protein product HARE, and by the methods described herein.

It is similarly believed that almost any eukaryotic expression system may be utilized for the expression of HARE e.g., baculovirus-based, glutamine synthase-based, dihydrofolate reductase-based systems, SV-40 based, adenovirus-based, cytomegalovirus-based, yeast-based, and the like, could be employed. For expression in this manner, one would position the coding sequences adjacent to and under the control of a promoter. It is understood in the art that to bring a coding sequence under the control of such a promoter, one positions the 5' end of the transcription initiation site of the transcriptional reading frame of the protein between about 1 and about 50 nucleotides "downstream" of (i.e., 3' of) the chosen promoter.

Where eukaryotic expression is contemplated, one will also typically desire to incorporate into the transcriptional unit which includes the HARE gene or DNA, an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

It is contemplated that virtually any of the commonly employed host cells can be used in connection with the expression of HARE in accordance herewith. Examples of preferred cell lines for expressing HARE cDNA of the present invention include cell lines typically employed for eukaryotic expression such as 239, AtT-20, HepG2, VERO, HeLa, CHO, WI 38, BHK, COS-7, 293, RIN and MDCK cell lines. This will generally include the steps of providing a recombinant host bearing the recombinant DNA segment encoding a functionally active HARE or an active peptide fragment thereof and capable of expressing the functionally active HARE or the active peptide fragment thereof; culturing the recombinant host under conditions that will allow for expression of the recombinant DNA segment; and separating and purifying the functionally active HARE protein or the active peptide fragment thereof which is able to specifically bind at least one of HA, chondroitin and chondroitin sulfate from the recombinant host.

Generally, the conditions appropriate for expression of the cloned HARE gene or cDNA will depend upon the promoter, the vector, and the host system that is employed. For example, where one employs the lac promoter, one will desire to induce transcription through the inclusion of a material that will stimulate lac transcription, such as isopropylthiogalactoside. Where other promoters are employed, different materials may be needed to induce or otherwise up-regulate transcription.

The present invention further includes antibodies raised against the Hyaluronan Receptor for Endocytosis proteins or fragments thereof described herein, and which are able to selectively bind an epitope of the HARE. In one instance, binding of the antibody to the HARE inhibits the binding of at least one of HA, chondroitin and chondroitin sulfate to HARE and subsequently prevents endocytosis of at least one of HA, chondroitin and chondroitin sulfate by the HARE. Methods of producing such antibodies generally involve immunizing a non-human animal with an immunogenic fragment of the HARE protein. In a preferred embodiment, the immunogenic fragment may comprise an HA-binding domain of HARE. Methods of producing such antibodies are well known to a person of ordinary skill in the art, and therefore no further description is required.

In a preferred embodiment, the antibody of the present invention is a monoclonal antibody. The term "monoclonal antibody" as used herein refers to a homogenous preparation of antibody molecules, produced by a hybridoma, all of which exhibit the same primary structure and antigenic specificity. That is, all of the antibody molecules of a particular monoclonal antibody preparation recognize and selectively bind the same epitope of HARE. The monoclonal antibodies are produced by methods generally well known to a person of ordinary skill in the art, and briefly involve culturing the hybridoma cell producing the monoclonal antibody specific for HARE under conditions that permit production of such monoclonal antibody.

The monoclonal antibodies of the present invention may be utilized in methods requiring administration of such or similar monoclonal antibody to a subject, such as a human. However, when the monoclonal antibodies are produced in a non-human animal, such as a rodent, administration of such antibodies to a human patient will normally elicit an immune response, wherein the immune response is directed towards the antibodies themselves. Such reactions will limit the duration and effectiveness of the therapy. To overcome such problem, the monoclonal antibodies of the present invention may be "humanized", that is, the antibodies are engineered such that antigenic portions thereof are removed and like portions of a human antibody are substituted therefor, while the antibodies' affinity for an epitope of HARE is retained. This engineering may only involve a few amino acids, or may include entire framework regions of the antibody, leaving only the complementarity determining regions of the antibody intact. Several methods of humanizing antibodies are known in the art and are disclosed in U.S. Pat. No. 6,180,370, issued to Queen et al on Jan. 30, 2001; U.S. Pat. No. 6,054,927, issued to Brickell on Apr. 25, 2000; U.S. Pat. No. 5,869,619, issued to Studnicka on Feb. 9, 1999; U.S. Pat. No. 5,861,155, issued to Lin on Jan. 19, 1999; U.S. Pat. No. 5,712,120, issued to Rodriquez et al on Jan. 27, 1998; and U.S. Pat. No. 4,816,567, issued to Cabilly et al on Mar. 28, 1989, the Specifications of which are all hereby expressly incorporated herein by reference. Therefore, no further explanation of methods of humanizing antibodies is required herein.

Such monoclonal antibodies may be utilized to purify functionally active HARE from a biological sample containing HARE via affinity purification. In preferred embodiments, the biological sample may be a tissue rich in sinusoidal cells of the reticuloendothelial system, such as at least one of liver, spleen, lymph nodes and bone marrow. However, it is to be understood that the biological sample may be any sample containing a functionally active HARE.

Affinity purification of proteins utilizing antibodies raised against such proteins is well known to a person of ordinary skill in the art. Briefly, an affinity matrix comprising a monoclonal antibody of the present invention bound to a solid support may be produced by methods well known in the art, and the biological sample may be contacted with the affinity matrix such that HARE in the biological sample binds to the monoclonal antibody of the affinity matrix. The HARE bound to the monoclonal antibody of the affinity matrix may be separated from the remainder of the biological sample by methods well known in the art. The HARE protein is then released from the monoclonal antibody of the affinity matrix and eluted from the affinity column by the addition of a solution, referred to as an eluate, which disrupts the binding between the HARE protein and the antibody. Such eluates are well known in the art, and may include solutions having a lower pH, solutions having a higher salt concentration, and the like. In preferred embodiments, the solution utilized for elution of the HARE protein is based on the ability of the solution to retain the functional activity of the HARE protein. That is, exposure to low pH or high salt may affect the conformations of some proteins, and therefore an eluate is chosen that does not have any effect on the activity of the protein to be eluted.

In another embodiment of the present invention, a method of identifying compounds which inhibit binding of at least one of HA, chondroitin and chondroitin sulfate to HARE is provided. The method includes providing a purified fragment of HARE capable of binding at least one of HA, chondroitin and chondroitin sulfate, forming a first affinity matrix comprising the purified fragment of HARE bound to a solid support, contacting a test compound with the first affinity matrix to form a treated affinity matrix, contacting at least one of HA, chondroitin and chondroitin sulfate with the first affinity matrix and contacting HA with the treated affinity matrix, and determining that the test compound inhibits binding of at least one of HA, chondroitin and chondroitin sulfate to HARE when at least one of HA, chondroitin and chondroitin sulfate binds to a greater extent to the first affinity matrix than to the treated affinity matrix. The purified fragment of HARE may be a soluble fragment of HARE, such as an extracellular domain of HARE or an HA-binding domain of HARE.

In yet another embodiment of the present invention, a method of treating a liquid solution containing at least one of HA, chondroitin and chondroitin sulfate is provided. Such method includes providing an affinity matrix comprising a functionally active fragment of HARE, as described herein above, bound to a solid support, and exposing a quantity of the liquid solution to the affinity matrix wherein at least one of HA, chondroitin and chondroitin sulfate contained in the liquid solution is removed therefrom. Such liquid solution may be blood or plasma, such as when blood or plasma is removed from a dialysis patient and filtered to remove contaminants and waste.

The following examples illustrate the practice of the preferred embodiments of the present invention. However, the present invention is not limited to the examples set forth.

EXAMPLE

Materials and Methods

Preparation of LECs and LEC membranes. LECs were isolated from male Harlan Sprague-Dawley rats (Harlan, Indianapolis, Ind.) by a modified collagenase perfusion procedure (Oka and Weigel, *J. Cell Biochem.* 36:169 (1988)), followed by differential centrifugation and then discontinuous Percoll gradient fractionation. The final LECs were collected from the 25/50% interface and washed three times with phosphate-buffered saline at 4° C., and are greater than about 95% pure. For preparation of LEC membranes, the cells were hypotonically swollen, homogenized, and centrifuged at 1000×g. The supernatant was then centrifuged at 105,000×g to obtain the total membrane fraction, which was stored frozen at −80° C. with no loss in HARE activity.

LEC Culture and HA Endocytosis. The LECs were collected from the first PBS wash after Percoll gradient fractionation. They were washed twice with RPMI-1640 (GIBCO) containing penicillin/streptomycin (100 units each) and 2 mM glutamine and plated at 1.5-2×10$^6$ cells/ml on fibronectin-coated (50 µg/ml) 24-well tissue culture plates for endocytosis experiments or glass coverslips for microscopy. After incubation at 37° C. for two hours in a 5% $CO_2$ atmosphere, the cells were washed three times with PBS, once with RPMI-1640 and put back in RPMI-1640 without serum if they were to be used immediately or with 2% heat inactivated bovine serum if they were to be cultured overnight before use.

Ligand Blot Assay. Samples were solubilized in an SDS sample buffer: 16 mM Tris-HCl, pH 6.8, 2% SDS, 5% glycerol, and 0.01% bromophenol blue. No reducing agent was added unless as noted. Cell or membrane samples were sonicated on ice for 10-20 seconds. After SDS-PAGE, the gel was electrotransferred to a 0.1 µm nitrocellulose membrane for 2 hours at 24 volts at 4° C. using 25 mM Tris, pH 8.3, 192 mM glycine, 20% methanol, and 0.01% SDS. The nitrocellulose was treated with TBS, 0.05% TWEEN™-20 at 4° C. for two hours or overnight, and then incubated with 2 µg/ml $^{125}$I-HA in TBS with or without a 150-fold excess of non-labeled HA (as competitor) to assess total or nonspecific binding, respectively. The nitrocellulose membrane was washed five times (five minutes each) with 0.05% TWEEN™-20 in TBS and dried, and the $^{125}$I-HA bound to protein was detected by autoradiography with Kodak BioMax film. Nonspecific binding in this assay is typically less than about 5%.

Figure 1:
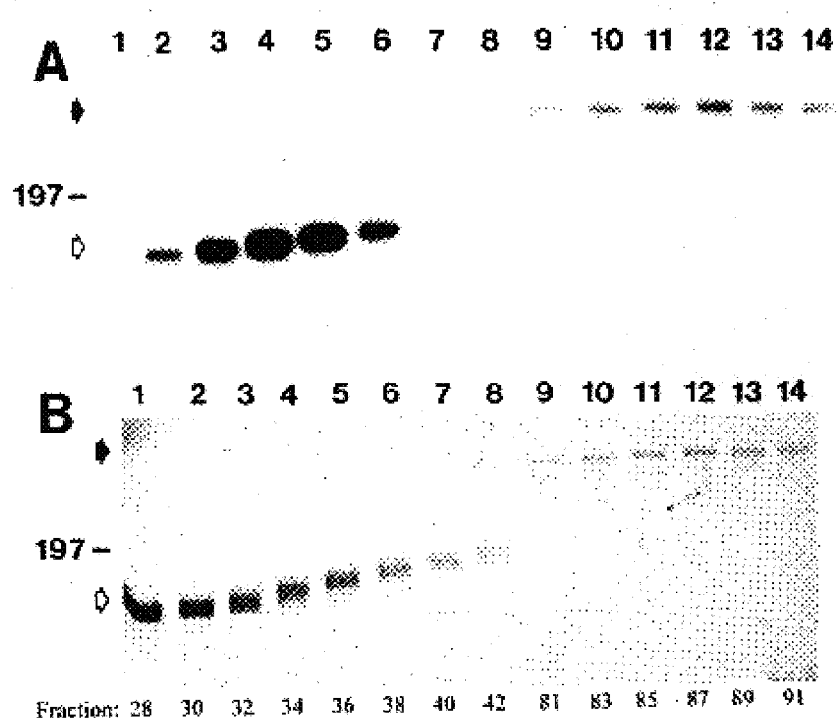
FIG. 1. Partial purification of the 175HARE from rat LECs by preparative SDS-PAGE. LEC membranes were solubilized in 1% NP-40 and the extract fractionated over RCA-I-Sepharose. HARE was eluted with lactose, concentrated and run on a preparative 5% polyacrylamide gel set up for continuous elution as described in Material and Methods. Collected fractions (0.5 mil/tube) containing HARE were found using a dot blot assay and a crude polyclonal Ab. Positive fractions were then subjected to SDS-PAGE and electotransfer and then either ligand blotted with $^{125}$I-HA followed by autoradiography (A) or stained with CPTS (B) to identify the 175HARE (open arrows) and the 300HARE (closed arrows). The increasing $M_r$ of the 175HARE (also referred to herein as the 175 kDa HARE) and 300HARE (also referred to herein as the 300 kDa HARE) may be due in part to heterogeneous size of these glycoproteins. Fractions 30-38 with very active 175HARE were pooled for monoclonal antibody (mAb) production.

Monoclonal Antibody Production. The starting antigen for mAb production was a highly purified fraction of the 175HARE from rat LEC membranes. After testing a battery of nine lectin resins for their ability to bind HARE, RCA-1 lectin was chosen because HARE binding was quantitative, easily displaced with lactose and a significant purification from other membrane proteins was obtained. A further advantage of lectin chromatography as a purification step is the ability to elute the LEC HARE in a relatively small volume. The eluted HARE was then subjected to nonreducing continuous elution SDS-PAGE using a Bio-Rad Model 491 Prep Cell at 22° C. and a flow rate of 0.8 ml/minute to separate individual proteins (FIG. 1). The running and elution buffers were 0.1% SDS, 25 mM Tris-190 mM Glycine, pH 6.8. The fractions were screened using the $^{125}$I-HA ligand blot assay and the nitrocellulose membrane was stained with copper phthalocyanine tetrasulfonic acid tetrasodium salt after the ligand blot assay to compare protein content and concentration in various fractions.

The eluted 175 kDa fractions were pooled, concentrated and used to immunize four mice. Two mice were each immunized with 20 µg of purified nonreduced protein and the other two mice were each immunized with 20 µg of purified protein that was first reduced with 10 mM DTT and then alkylated with 50 mM iodoacetamide. The mice were boosted twice at two-week intervals and blood was drawn from tail veins 6 weeks after the first immunization. The sera was tested for specific Ab by ELISA. Standard procedures (Harlow and Lane, 1988) were followed for cell fusion and limited dilution cloning. Briefly, 10$^8$ immunized mouse spleen cells were mixed with 2×10$^7$ SP 2/0-Ag 14 myeloma cells and fused in the presence of 50% polyethylene glycol (MW=1500). The hybrid cells were seeded in 96-well flat bottom plates in HAT selection medium. The hybridoma supernatants were screened using an ELISA assay with the 175 kDa antigen. Consistently positive hybridoma clones were used to produce ascites fluid as described by Harlow and Lane (1988). Antibody isotypes (ido) were determined using the ISO Strip kit from Boehringer Mannheim.

ELISA for Quantitation of Anti-HARE Activity. The 96-well ELISA plates were coated using 100 µl of 10 µg/ml purified 175 kDa protein at 4° C. overnight and then blocked with 1% BSA-TBS for one hour at room temperature. Preimmune or immune serum or hybridoma supernatant (100 µl)

was added to each well. The plate was incubated for two hours at room temperature, washed 6 times with 0.05% TWEEN™-20-TBS, and the secondary reagent, a mixture of goat anti-mouse IgG, IgM and IgA alkaline phosphatase conjugates (about 2 μg/ml each in about 100 μl) was added. The plate was incubated for two hours at room temperature and washed five times for five minutes each with 0.05% TWEEN™-20-TBS and 100 μl of freshly prepared p-nitrophenylphosphate substrate solution (as prepared using the Phosphatase Substrate System kit from Kirkegaard & Perry Laboratories) was added to each well. After incubation for 30-60 minutes at 37° C., 100 μl of 5% EDTA solution was added to the wells to stop the reaction. The plate was then read at 405 nm using a Spectra Max 340 (Molecular Devices).

Immunofluorescence. For analysis of rat tissues liver, spleen, brain, heart, kidney, muscle, lung, intestine, bone marrow and lymph node were minced on ice and fixed in 4% formaldehyde overnight at room temperature. Tissue sections (5 μm) were prepared by the Department of Pathology, University of Oklahoma Health Sciences Center. Sections were then dewaxed 5 times for 5 minutes each with xylene, followed by 5 washes for 5 minutes each with alcohol at room temperature. The tissue was treated with 0.05% trypsin, 0.53 mM EDTA for 30 minutes at room temperature, washed with TBS and then blocked with 10% goat serum in TBS at 4° C. overnight. A 1:250 dilution of individual ascites fluid or mixtures of ascites (100 μl) was added and the tissue slide was incubated for two hours at room temperature. The slide was washed five times for five minutes each with TBS at room temperature. Goat anti-mouse IgG-Rhodamine Red conjugate (10 μg/ml) was then added and the incubation continued for one hour at room temperature. The tissue slide was washed five times for five minutes each with TBS and a solution of SLOWFADE™ from Molecular Probes was added. A cover slip was overlaid, the edge sealed with finger nail polish, and the slides were viewed by fluorescence microscopy using a Nikon Diaphot 300 or by confocal microscopy using a LEICA TCS NT. For analysis of cultured LECs, the cells were cultured overnight on glass coverslips, fixed in 4% formaldehyde in PBS for 20 minutes at 23° C. and then permeabilized with 0.1% Triton X-100. Nonspecific binding was minimized by incubating the cells for 1-2 hours in TBS containing 10% goat serum and 1% bovine serum albumin. The cells were then washed, incubated for one hour at 23° C. with 5 μg/ml ascites from mAb-235 or normal mouse serum, washed, stained and processed as above with goat anti-mouse IgG conjugated to rhodamine red.

Immunocytochemistry. Rat tissues were dissected within 15 min after sacrifice and fixed in 10% neutral buffered formaldehyde at room temperature for 2 h, processed and paraffin embedded overnight on a Tissue Tek V.I.P processor. Tissue sections (5 μm) were collected on charged slides, and dried at 60° C. overnight. The slides were dewaxed 3 times for 3 min each with xylene, followed by 4 washes for 3 min each with alcohol (100%, 95%, 90%, 70%), followed by a single 2 min wash in water at room temperature. The endogenous peroxidase activity was quenched with 3% hydrogen peroxide for 6 min, followed by two 2 min water washes. The slides were digested for 15 min at 37° C. in pre-warmed 0.1N HCl containing 0.32 mg/ml pepsin, followed by a 2 min water wash and a 2 min PBS wash. The slides were washed with PBS and incubated with the appropriate primary antibody (1:500) at room temperature for 60 min. After a 1 min PBS wash, the slides were treated with secondary antiserum (biotinylated horse anti-mouse, 1:200) for 30 min at room temperature.

After another PBS rinse, the slides were incubated with streptavidin-horseradish peroxidase (1:1000 from Jackson Labs) for 30 min, washed once with PBS and once with distilled water. Color development was for 5 min with 2.0% (v/v) aminoethylcarbazine and hydrogen peroxide according to the manufacturer's instructions (ScyTek, Utah), followed by counterstaining with hematoxylin. Slides were viewed with an Olympus BX-40 light microscope equipped with an Olympus DP10 digital camera for photography.

Purification of the HARE. LEC membranes from 18 rats were suspended in 3.6 ml of TBS, 2% NONIDET™ P-40 and mixed by rotation at 4° C. for two hours. The solubilized membranes were diluted with TBS to 0.5% NONIDET™ P-40, centrifuged for 30 minutes at 100,00×g, and the supernatant was loaded at room temperature onto a RCA-I gel column (10 ml). The column was washed with 10 volumes of TBS, 0.05% TWEEN™-20. Bound proteins were eluted with 100 mM lactose in distilled water, dialyzed against multiple changes of TBS at 4° C. overnight, concentrated 10-fold using a CENTRICON™-30 (from Amicon), and then passed over an immuno-affinity column (about 8 ml) containing monoclonal antibody 175HAR-30 coupled to CNBr-activated Sepharose (about 2 mg/ml resin). The affinity-column was washed with 10 volumes of 0.05% TWEEN™-20 in TBS and then eluted with 100 mM sodium citrate, pH 3.0. Eluted fractions were neutralized by collection into 1 M Tris. Fractions containing protein were pooled, dialyzed against TBS at 4° C. overnight, and then concentrated using a CENTRICON™-30 (Amicon).

Deglycosylation of HAREs with N-Glycopeptidase F. Purified HARE (1.17 μg) was heated with 0.05% SDS at 90° C. for three minutes. Samples (22 μl) were chilled on ice for four minutes and then 0.5 M Tris-HCl, pH 7.2, was added to a final concentration of 10 mM. One-half unit of N-Glycopeptidase F and distilled water were added to give a final volume of 25 μl. The samples were incubated at 37° C. overnight, 9 μl of 4-fold concentrated SDS sample buffer was added, and they were heated for three minutes at 90° C. The samples were subjected to SDS-PAGE, and protein was detected by silver staining, or receptor activity was determined by the $^{125}$I-HA ligand blot assay.

Two-Dimensional Electrophoresis. Affinity-purified HARE (about 1.5 μg) was subjected to SDS-PAGE without reduction, and the gel was stained with Coomassie Blue. The 175- and 300 kDa proteins, in the case of the rat HARE, or the 190 kDa and about 315 kDa proteins, in the case of the human HARE, were excised from the gel, cut into smaller pieces, divided into two portions, and incubated at 90° C. for four minutes in SDS sample buffer, with or without reduction using 10 mM dithiothreitol followed by 50 mM iodoacetamide (identical results were also obtained with or without reduction using 1.25% β-mercaptoethanol). The samples were then subjected to a second dimension of SDS-PAGE in the absence of reducing agent, and parallel portions were processed in-gel to identify the proteins by silver staining or after transfer to nitrocellulose in order to assess HARE activity by the $^{125}$I-HA ligand-blot assay described herein above.

Sequencing of HARE. Rat LEC HARE was purified from membrane extracts by successive immunoaffinity chromatography with RCA-I agarose and then mAb-30 Sepharose as described herein above. The purified proteins were subjected to SDS-PAGE and stained with Coomassie Blue. The 175 kDa HARE protein band was excised and sent to Dr. William Lane at the Harvard Microchemistry Facility for internal peptide sequence analysis after trypsin digestion. Additionally, some 175 kDa HARE was partially purified by two-dimensional electrophoresis (isoelectric focusing followed by SDS-PAGE) as described herein above, and the appropriate protein zones were sent to the Rockefeller University Microchemistry Facility for internal sequence analysis of tryptic peptides. N-terminal sequence analysis of immunoaffinity-purified 175 kDa HARE was also performed by Dr. Ken W. Jackson in the Molecular Biology Resource Facility of the William K. Warren Medical Research Institute, University of Oklahoma Health Sciences Center.

The resulting amino acid sequences of peptides (Table II) obtained by the Harvard facility (GT-68 (SEQ ID NO:8), GT-81 (SEQ ID NO:9), GT-123 (SEQ ID NO:10), GT-139 (SEQ ID NO:11), and GT-208 (SEQ ID NO:12)) and the Rockefeller University Facility (peptide 1 (SEQ ID NO:13), peptide 3 (SEQ ID NO:14) and peptide 5 (SEQ ID NO:15)) were used to design degenerate oligonucleotide primers for RT-PCR analysis and to confirm isolation of the correct cDNA.

RT-PCR. Total RNA from isolated rat LECs was prepared using TRIzol reagent, and the mRNA was isolated from total RNA using a polyAtract mRNA Isolation Kit following the manufacturer's recommended protocols. First-strand cDNA was synthesized using the thermoscript RT-PCR system from Life Technologies with random hexameric oligonucleotides or oligo(dT)$_{20}$. The PCR reactions were carried out with incubation at 94° C. for 2 minutes; 30 cycles of 45° C. for 30 seconds, 72° C. for 6 minutes and 94° C. for 30 seconds; one cycle of 45° C. for 30 seconds and 72° C. for 15 minutes using degenerate oligonucleotide primers (Table II) based on a particular unique peptide sequence. The PCR products were cloned into pCR™2.1 or pTrcHis2 expression vector using TA CLONING™ kits from Invitrogen.

cDNA library screening. An endothelial cell cDNA expression library was prepared from LEC mRNA in λZAP EXPRESS™ by Stratagene. Approximately $2.4 \times 10^5$ pfu were screened with two 7-digoxigenin-labeled cloned RT-PCR products produced with primer pair 208F-123R (SEQ ID NO:3 and SEQ ID NO:16, respectively) (370 bp) and 123F-81R (SEQ ID NO:17 and SEQ ID NO:18, respectively) (1,500 bp). All screening was performed on duplicate nitrocellulose filters. The nitrocellulose membranes were denatured in 1.5 M NaCl, 0.5 M NaOH for 2 minutes, neutralized in 1.5 M NaCl, 0.5 M Tris, pH 8.0 for 5 minutes, rinsed with 0.2 M Tris, pH 7.5 in 2×SSC for 30 seconds, and then baked at 80° C. for 1 hour. After pre-hybridization at 45° C. for 30 minutes in QuikHyb Hybridization Solution, the membranes were allowed to hybridize overnight at 45° C. with a mixture of two digoxygenin-labeled probes, which were PCR products derived

TABLE II

Summary of Oligonucleotides and Amino acid Sequences Derived From Peptides of the Rat 175 kDa HARE Protein

| HARE Peptide Designation | SEQ ID NO: | Amino acid Sequence | Start-end residue number |
|---|---|---|---|
| GT-68 | 8 | PLGQYK | 1070-1075 |
| GT-81 | 9 | AYPTTYASQK | 1120-1129 |
| GT-123 | 10 | VLQDLTTVAANHGYTK | 604-619 |
| GT-139 | 11 | QLYVNEAPIDYTNVATDK | 103-120 |
| GT-208 | 12 | LAGPGPFTVFAPLSSSFNHEPR | 488-509 |
| Peptide 1 | 13 | DILRYHVVLGEK | 62-73 |
| Peptide 3 | 14 | VLEIQK | 129-134 |
| Peptide 5 | 15 | LEALPEQQDFLFNQDNK | 651-668 |
| N-terminal | 27 | SLPSLLTRLEQMPDYSIF (major) | 1-18 |
| N-terminal | 28 | XXVIHGLEKVXXIQKNR (minor) | 122-136 |

| Designation | SEQ ID NO: | Oligonucleotides Sequence |
|---|---|---|
| 81R | 18 | 5'-GCRTAIGTNGTNGGRTANGC |
| 123R | 16 | 5'-TAICCRTGRTTNGCNGCNAC |
| 123F | 17 | 5'-GTNGCNGCNAAYCAYGGITA |
| 208F | 3 | 5'-CCNTTYACNGTNTTYGCICC |
| GSP-1R | 19 | 5'-CTCCAAACACGGGTTGATTTC |
| GSP-1R (AsnI) | 22 | 5'-CTCCAAACACGGATTAATTTC |
| GSP-1F (AsnI) | 23 | 5'-GAAATTAATCCGTGTTTGGAG |
| GSP-2R | 20 | 5'-TGGGGTGGTTCTTTTACAGTC |

TABLE II-continued

Summary of Oligonucleotides and Amino acid Sequences Derived
From Peptides of the Rat 175 kDa HARE Protein

```
GSP-5F (EcoRI)    21    5'-TGGTGGAATTCTTTACCAAGTCTACTCACC

GSP-GT81R          4    5'-GGCATACGTAGTCGGGTAGGC
```

The two rat HARE proteins were purified from isolated LECs
after extraction and immunoaffinity chromatography using
anti-rat 175 kDa HARE mAbs. The immunoaffinity-purified proteins were subjected to SDS-PAGE and the gels were either
stained with Coomassie Blue to identify the proteins to be
excised for determination of internal peptide sequences or
the proteins in the gel were electro-transferred to a PVDF
membrane for determination of N-terminal sequence. As
described in Experimental Procedures, the purified 175 kDa
HARE protein band was excised and sent to the Harvard Microchemistry Facility (GT peptides) and a partially purified
preparation was sent to the Rockefeller University Microchemistry Facility (Peptides 1, 3 and 5) for determination of
internal protein sequences after trypsin digestion. The location of each peptide sequence found in the deduced protein
sequence of the 175 kDa HARE protein (based on its cDNA) is
indicated by the amino acid position number for the starting
and ending residues in 175 kDa HARE protein sequence. The
one- letter code for amino acids is used; X indicates unknown
residues. One-letter abbreviations conform to the IUB group
codes for oligonucleotides. Amino acid sequences used to
design forward (F) and reverse (R) oligonucleotide primers
are shown in boldface. Restriction sites introduced in the
indicated oligonucleotides are shown in italics and boldface.

from the primer pairs 208F-123R (SEQ ID NO:3 and SEQ ID NO:16, respectively) and 123F-81R (SEQ ID NO:17 and SEQ ID NO:18, respectively). The membranes were then washed twice in SSC containing 0.05% SDS at room temperature, followed by two washes in 0.1×SSC containing 0.1% SDS at 45° C. The positive λZAP-EXPRESS™ bacteriophage were identified and purified, and the cloned DNA inserts were excised in vivo into PBK-CMV phagemid using ExAssist helper phage and XLOLR bacterial cells as recommended in the manufacturer's manual. The phagemid DNAs were purified and the inserts were sequenced.

Figure 19:
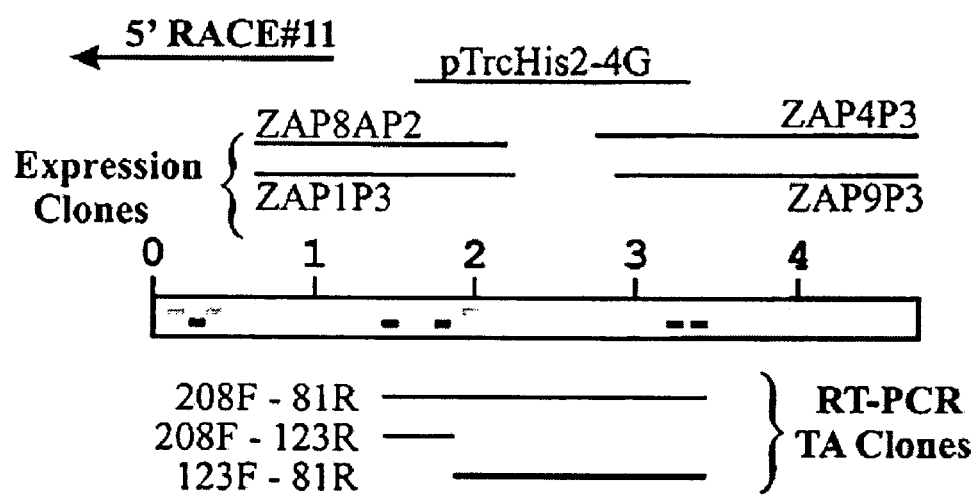
FIG. 19. Assembly of the 4.7-kb cDNA encoding the rat 175 kDa HARE. Peptide sequences obtained from the purified HARE by the Harvard Microchemistry (dark gray) or the Rockefeller Facilities (light gray) are indicated by rectangles at the corresponding nucleotide positions. The scale units indicated are in kilobases. The ZAP1P3, ZAP8AP2, ZAP4P3, and ZAP9P3 clones were isolated by screening the λ-ZAP EXPRESS™ cDNA library with specific PCR-generated probes. The clone 5'RACE #11 was obtained from 5'-rapid amplification of cDNA ends (5'-RACE) using a MARATHON™ cDNA Amplification Kit (Clontech). All other clones were obtained by RT-PCR using degenerate oligonucleotide primers based on peptide sequences (Table II) and cloned into the pCR™ 2.1 vector or pTrcHis2 expression vector.

Northern blot analysis. Total RNA and mRNA were isolated from rat LECs as described above. RNA (20 µg/lane) or mRNA (1 µg/lane) samples in 20 mM morpholinopropanesulfonic acid, 5 mM sodium acetate, pH 7.0, 1 mM EDTA, containing 6% (v/v) formaldehyde and 50% (v/v) formamide were heated to 65° C. for 5 minutes, placed immediately on ice and then electrophoresed on a 0.8% agarose gel in 20 mM morpholinopropanesulfonic acid, 5 mM sodium acetate, pH 7.0, 1 mM EDTA and 2% (v/v) formaldehyde. The RNA was transferred overnight to nylon membranes by the capillary method using 5×SSC, were heated for one hour at 90° C. in an oven and washed with distilled water to remove salts. The membranes were pretreated in QUIKHYB™ solution (Stratagene) for 30 minutes at 45° C. in a hybridization oven. The membranes were then hybridized at 45° C. with three $^{32}$P-labeled DNA probes, prepared by the random primer extension method (Taylor et al, *Biochim. Biophys. Acta.* 442:324 (1976)). The three probes were made from the inserts of clones 5'RACE #11 (1108 bp), ZAP1P3 (1216 bp) and ZAP9P3 (1979 bp) and were located at the 5'-end, the middle, and the 3'-end of the 175 kDa HARE nucleotide sequence, respectively (FIG. 19).

After the above pre-hybridization step, the $^{32}$P-labeled DNA probes (1.25×10$^7$ total counts per 10 ml of hybridization solution; specific activity of the probe 10$^8$ cpm/µg) were added to the hybridization tube together with 100 µl of 10 mg/ml sonicated salmon sperm DNA (Stratagene). The membranes were allowed to hybridize at 45° C. overnight in a hybridization oven and were then washed twice for 15 minutes each at room temperature with 2×SSC containing 0.1% (w/v) SDS followed by three washes for 30 minutes each at 50° C. with 0.1×SSC and 0.1% (w/v) SDS (a high-stringency wash). The membranes were allowed to air dry on filter paper at room temperature and the hybridization results were assessed by autoradiography using Kodak BioMax film.

5'-RACE. The 5'-end of the 175 kDa HARE cDNA was obtained using a MARATHON™ cDNA amplification kit from Clontech for 5'RACE analysis. Oligonucleotide GSP-1R (SEQ ID NO:19) was used for first strand cDNA synthesis. After second strand cDNA synthesis by the method of Gubler and Hoffmann (*Gene* 25:263 (1983)), a library of adaptors (Clontech) was ligated to the double-stranded cDNA. DNAs were amplified by PCR using adaptor-ligated ds-cDNA as the template with primer GSP-2R (SEQ ID NO:20) and the adaptor primer from the MARATHON™ kit as the primer pair. PCR conditions were as follows: 94° C. for 2 minutes; 30 cycles of 45° C. for 30 seconds, 72° C. for 6 minutes and 94° C. for 30 seconds; 1 cycle of 45° C. for 30 seconds and 72° C. for 15 minutes. The PCR products were then cloned into pCR™2.1 using the TA CLONING™ kit from Invitrogen and colonies were screened by PCR using GSP-2R (SEQ ID NO:20) and the adaptor primer. Plasmid DNA from positive clones were purified with QIAprep™ spin plasmid kits and the inserts were sequenced.

Construction of a 4.7 kb 175 kDa HARE cDNA with an N-terminal Ig k-chain leader sequence. An 1152 bp 5' fragment of the 175 kDa HARE cDNA was amplified by RT-PCR using pfu TURBO™ polymerase with GSP-5F(EcoRI) (SEQ ID NO:21), which contains an EcoRI restriction site and encodes the N-terminal seven amino acids of the 175 kDa protein, and GSP-1R(AsnI) (SEQ ID NO:22), which contains two silent G→A mutations that create a AsnI restriction site. The PCR products were separated on a 1% agarose gel, and the 1.15 kb DNA band was excised and purified using a QIAquick™ Kit. The DNA was cloned into the pSecTag2 B vector, which contains a murine Ig kappa chain leader sequence for protein secretion. The ligated DNA was electro-transformed into TOP10F' electro-competent cells (Invitrogen), and the DNA insert was amplified by bacterial growth and purified with a QIAprep™ spin miniprep kit. An interior 2226 bp fragment of the 175 kDa HARE cDNA sequence was amplified by RT-PCR using pfuTurbo DNA polymerase with GSP-1F(AsnI) (SEQ ID NO:23), which contains two silent C→T mutations to create a AsnI restriction site, and primer GSP-GT81R (SEQ ID NO:4). The PCR products were separated on a 1.0% agarose gel, and the 2.2 kb DNA band was excised, purified using a QIAquick™ Gel Extraction kit and digested with AsnI and Eco52I. There is a Eco52I site within the 3' ~one-third of the HARE sequence (starting at nucleotide position 3329). The 1.5 kb insert from the ZAP9P3 clone, which contains the 3' end of the 175 kDa HARE cDNA including the poly A site, was amplified, purified and cut with Eco52I and XhoI to give the third fragment, which contains 1378 bp. The three purified fragments of HARE cDNA were then simultaneously ligated with pcDNA3.1, which had been digested with Nhe I and XhoI, at a molecular ratio of 2:1 (insert:vector). The ligated DNA was electroporated into TOP10F' electro-competent cells, and colonies were screened by PCR and restriction enzyme digestion to identify full-length inserts. Plasmid DNA from positive clones was amplified in TOP10F' bacteria, purified using endofree plasmid maxi kits and the complete inserts were sequenced. The resulting plasmid containing the 4708 bp cDNA (SEQ ID NO:1) encoding the 175 kDa HARE is designated p175HARE-k.

Transient expression of the 175 kDa HARE in COS 7 cells. COS 7 cells were grown to ~80% confluence in 35 mm culture dishes, using DMEM with 10% fetal calf serum, and then transfected with the purified p175HARE-k DNA (2 µg) using 6 ml of FuGENE 6. At 40 h post-transfection, the cells were detached by treatment with 0.05% trypsin and 0.53 mM EDTA, collected and washed two times with PBS. The cells were extracted with TBS containing 1% NONIDET™ P-40 and analyzed by SDS-PAGE. As described previously the expression of HARE protein was tested by Western analysis using anti-HARE mAbs as described herein before, and expression of active HARE was assessed by the ligand blot assay using $^{125}$I-HA as described herein before.

Selection of stable tranfectants expressing the 175 kDa HARE. SK-Hep1 cells (from ATCC) were transfected with the purified p175HARE-k DNA using FuGENE 6 in 35 mm culture dishes. Twenty-four hours after transfection, the cells were transferred to 100 mm dishes and grown in DMEM containing 10% fetal calf serum and 0.4 mg/ml of G418 for selection. After 15-20 days, individual colonies of antibiotic-resistant transfected cells were isolated using cloning rings and detached by treatment with 0.05% trypsin and 0.53 mM EDTA for 5 minutes at room temperature. Collected cells were expanded in 12-well plates to assess HARE protein expression and function by ELISA, Western blot and $^{125}$I-HA binding assays. Cultures that were positive in these assays were further purified by limiting dilution cloning.

Endocytosis of $^{125}$I-HA by SK-Hep1 stable cell lines. Stably transfected cell lines were grown to confluence in DMEM with 10% fetal calf serum containing 0.4 mg/ml G418. The cells were incubated at 37° C. in medium without serum for 1 hour, and the plates were then placed on ice and the cells washed 2 times with 1 ml Hanks. Medium containing 2 µg/ml $^{125}$I-HA with or without 200 µg/ml unlabeled HA was added to each well, and the cells were incubated either on ice for 60 minutes to assess surface binding or at 37° C. to allow internalization of ligand. At the noted times, the medium was aspirated, and the cells were washed 3 times with Hanks, lysed in 0.3N NaOH, and radioactivity and protein were determined.

Immunofluorescence analysis of 175 kDa HARE expression. Transiently transfected COS 7 cells or stably transfected SK-HARE cells were collected 24 hours after transfection or culture, respectively, by treatment with 0.05% trypsin and 0.53 mM EDTA, washed, transferred onto a tissue culture chamber/slide and grown for 12-18 hours. The cells were then fixed with 4% (v/v) formaldehyde in PBS for 20 minutes at room temperature and then incubated with or without 0.1% Triton X-100 to permeabilize the cells. The slide was incubated with 10% goat serum in PBS containing 1% BSA for 1 hour at room temperature and then incubated with a mixture of eight anti-175 kDa HARE mAbs (1:2000 dilutions of each ascites fluid in 10% goat serum, 1% BSA) for 15 minutes at room temperature. The slide was then washed 5 times for 5 minutes each with TBS and goat anti-mouse IgG (H+L)-Rhodamine Red conjugate (10 µg/ml) was added. The slide was incubated for 30 minutes at room temperature, washed 5 times for 5 minutes each with TBS and then a solution of SLOWFADE™ (Molecular Probes) was added. A cover slip was overlaid, the edge sealed with finger nail polish, and the slides were viewed by confocal fluorescence microscopy using a LEICA TCS NT.

Purification and sequence analysis of the HARE from human spleen. Human spleen tissue was obtained from a 14 year old female patient undergoing spleenectomy for hereditary spherocytosis, following approval from the University of Rochester Research Subjects Review Board. The tissue was cut into small pieces on ice, added to 2% NONIDET™ P-40 in TBS containing a mixture of proteinase inhibitors (2 mM diisopropyl fluorophosphate, 1 mM phenylmethylsulfonyl fluoride and 1 mM N-ethylmaleimide), then homogenized using a Tissumizer power homogenizer (Tekmar Co) and incubated at 4° C. for 1 h. The extract was diluted four-fold with TBS and centrifuged at 12,000×g for 30 min at 4° C. The supernatant was loaded onto a column containing anti-rat HARE mAb-30 for affinity chromatography (~2 mg/ml IgG coupled to CNBr-activated Sepharose). The column was washed with 10 volumes of TBST and then eluted with 100 mM sodium citrate, pH 2.5. Eluted fractions were neutralized with 1 M Tris, pooled, dialyzed against TBS at 4° C., and concentrated using a CENTRICON™-30 device (Amicon). The concentrated sample was subjected to SDS-PAGE and in some cases then transferred to nitrocellulose. The HA-binding activity of HARE was determined by a $^{125}$I-HA ligand-blot assay, and HARE protein was localized by Western blot analysis as described below. Immunoaffinity-purified human HARE preparations were subjected to SDS-PAGE and gels were stained with Coomassie Blue to identify the proteins. The 190 kDa human HARE protein band was excised and sent to the Protein Chemistry Lab at the University of Texas Medical Branch at Galveston for trypsin digestion and amino acid sequence analysis of internal peptides. Samples of the tryptic digests were also sent to the Mass Spectroscopy Facility at Louisiana State University.

Purification of human spleen mRNA and RT-PCR. Human spleen tissue was cut into small pieces and homogenized on ice using TRIzol reagent to isolate the total RNA. The mRNA was isolated from total RNA using a PolyATtract mRNA Isolation Kit following the manufacturer's recommended protocols. First-strand cDNA was synthesized using the Thermoscript II RT-PCR system from Life Technologies with random hexameric oligonucleotides or oligo(dT)$_{20}$. The PCR reactions using ADVANTAGE 2™ Polymerase Mix from CLONTECH were carried out with incubation at 94° C. for 2.5 min; 35 cycles of 50° C. for 1 min, 68° C. for 3 min, and 94° C. for 1 min; one cycle of 50° C. for 1 min and 68° C. for 15 min. PCR products were obtained using the following pairs of oligonucleotides (Table III), based on either the human 190 kDa HARE peptide sequences (HSP, HARE-specific primer) or the nucleic acid sequence (BAB primer) under GenBank accession number AK024503 (mRNA for FLJ00112 protein, which is under accession #BAB15793): BAB1F-HSP2R (SEQ ID NO:5 and SEQ ID NO:7, respectively), HSP3F-BAB4R (SEQ ID NO:26 and SEQ ID NO:29, respectively), BAB6F-BAB7R (SEQ ID NO:30 and SEQ ID NO:31, respectively), BAB1F-BAB10R (SEQ ID NO:5 and SEQ ID NO:32, respectively), HSP2F-BAB10R (SEQ ID NO:33 and SEQ ID NO:32, respectively), BAB10F-HSP3R (SEQ ID NO:34 and SEQ ID NO:35, respectively), and BAB9F-HSP3R (SEQ ID NO:36 and SEQ ID NO:37, respectively). The PCR products were subjected to electrophoresis using a 1% (w/v) agarose gel and the DNA bands were excised and purified using a Gel Extraction Kit. The purified PCR DNA products were cloned into pCR ™4-TOPO vector using the TOPO-TA CLONING™ Kit (Invitrogen). The colonies were screened by PCR and the DNA insert size was verified by restriction enzyme digestion using EcoRI. The plasmid DNAs from positive clones were purified using QIAprep™ Spin plasmid Kits and the complete inserts were sequenced by the DNA Sequencing Facility of the Oklahoma Medical Research Foundation, Oklahoma City, Okla.

Western blot analysis of human HARE. Nitrocellulose membranes were blocked with 1% BSA in TBS at 4° C. overnight either after the ligand blot assay or directly after SDS-PAGE and electotransfer as described by Burnette (*Anal. Biochem.* 112:195 (1981)) and as above using purified HARE or human spleen extract. The membrane was then incubated with anti-rat HARE mAbs (e.g. 1:5000 dilution of ascites) at room temperature for 2 h, washed 5 times for 5 min each with TBST, and incubated with goat anti-mouse IgG conjugated to alkaline phosphatase for 1 h at room temperature. The nitrocellulose was washed 5 times for 5 min each with TBST and incubated with the substrates p-nitro blue tetrazolium and 5-bromo-4-chloro-3-indolyl phosphate p-toluidine salt for color development, which was stopped by washing the membrane with distilled water.

Results

Development of mAbs to the 175 HARE. Because we previously identified an HA-binding protein of 85 kDa in hepatocytes (Frost et al, *Biochemistry* 29:10425 (1990)) and because histones avidly bind HA as well (Yannariello-Brown et al, *Biochem. and Biophys. Res. Commun.* 218:314 (1996)), our purification scheme for the 175HARE began with LECs prepared by collagenase perfusion of rat liver, rather than with whole liver. The final partial purification step for preparing the 175HARE antigen for mAb production was preparative 1-D SDS-PAGE, which separated the 175HARE and 300HARE and gave fractions of discrete masses that still retained HA-binding activity (FIG. 1). The eluted 175 kDa fractions were pooled, concentrated, and used to immunize mice as the nonreduced protein or after being reduced and alkylated. We isolated multiple clones of 11 different hybridomas that were consistently positive in ELISA screens with the nonreduced or reduced 175 kDa antigen.

Figure 2:
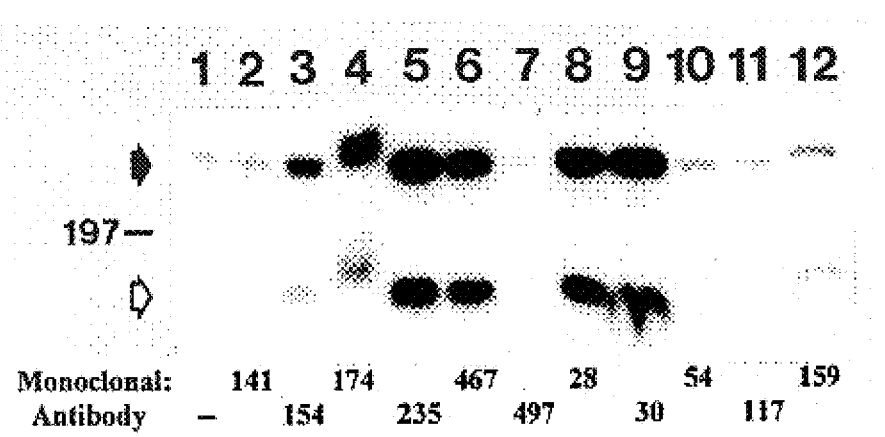
FIG. 2. Immunoprecipitation of the 175HARE and 300HARE from LEC extracts by a panel of 175HARE-mAbs. Abs from ascites produced from each hybridoma were bound to Protein G-Sepharose, except for #159 which was bound to rabbit anti-mouse-IgM-Sepharose. After washing 5 times with TBS containing 0.1% TWEEN™-20 for 5 min each, the resin was incubated with NP-40 extracts of LEC membranes at 4° C. for 2 h. The resin was then washed as above, eluted with 1× Laemmli sample buffer and the eluate was subject to SDS-PAGE and ligand blotting. The solid and open arrows indicate the positions of the 300HARE and 175HARE, respectively. Resin with no mAb (lane 1) or with the negative control mAbs (141, 117 and 497) did not immunoprecipitate HARE. Of the Western-positive mAbs (see FIGS. 3 and 4), four showed roughly equal ability to purify both HAREs; numbers 235, 467, 28 and 30.
Figure 3:
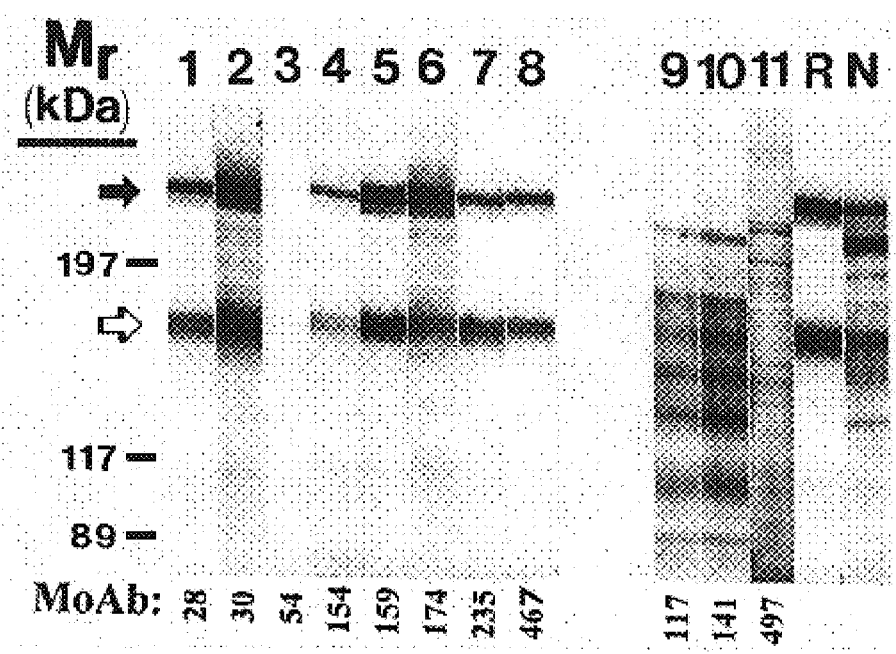
FIG. 3. Reactivity of a panel of 175HARE-mAbs in Western analysis after nonreducing SDS-PAGE of LEC extracts. Ascites from 11 hybridoma clones, that were positive in ELISA screens with the 175HARE antigen, were screened (at a 1:1,000 dilution) for reactivity with lysates of rat LECs. Seven of these clones showed strong reactivity with proteins at both 175 and 300 kDa (lanes 1-8 except lane 3). Clone 54 only recognizes the reduced protein (FIG. 4). Three clones gave very different patterns (lanes 9-11) and do not recognize the 175HARE antigen. R and N show mouse antisera raised against reduced (R) or nonreduced (N) 175HARE antigen. The solid and open arrows indicate the positions of the 300HARE and 175HARE, respectively.
Figure 4:
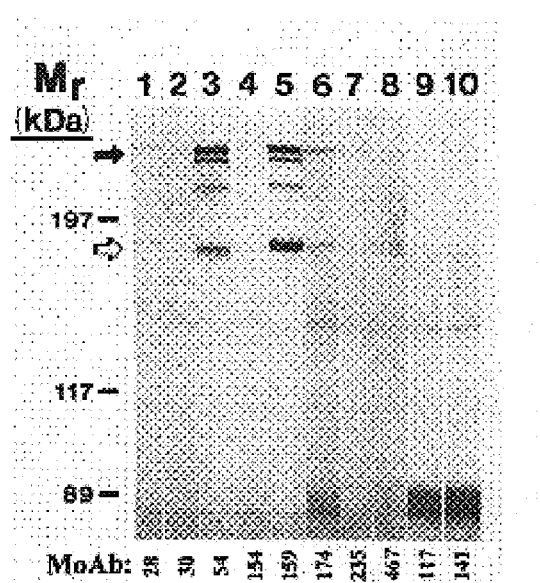
FIG. 4. Reactivity of a panel of anti-175HARE mAbs in Western analysis after reducing SDS-PAGE of LEC extracts. Only mAbs 54 (lane 3) and 159 (lane 5) show strong reactivity, which is identical, with the reduced 175HARE and 300HARE proteins. The solid and open arrows indicate the positions of the nonreduced 300HARE and 175HARE, respectively. MAb-174, which also blocks HA binding (FIGS. 9 and 10), shows weaker reactivity with the reduced 175HARE and the 260 kDa subunit of the 300HARE (lane 6). The other mAbs, including those positive for the nonreduced proteins, are not reactive.

Interaction of mAbs with the 175HARE after detergent solubilization or SDS-PAGE. MAbs were prepared from ascites fluid produced by the hybridomas and tested for their ability to immunoprecipitate the active 175HARE (FIG. 2) and for their reactivity with a 175 kDa species in Western blots (FIGS. 3 and 4). The former ability shows that a mAb recognizes the correct protein, the bone fide 175HARE. Three of the original 11 mAbs isolated (numbers 117, 141 and 497) were not against the 175HARE, since they have a different Western pattern (FIG. 3, lanes 9-11) and do not immunoprecipitate HARE (FIG. 2, lanes 2, 7 and 11). This result was expected, since the starting antigen was not pure. These negative clones were useful as negative controls.

Eight mAbs were obtained that recognize both the rat LEC 175HARE and 300HARE in Western blots after either non-reducing (FIG. 3) or reducing (FIG. 4) SDS-PAGE. The eight mAbs include mAb-28 (ATCC number PTA-5354), mAb-30 (ATCC number PTA-5355), mAb-54 (ATCC number PTA-5356), mAb-154 (not viable for biological deposit), mAb-159 (ATCC number PTA-5358), mAb-174 (ATCC number PTA-5359), mAb-235 (ATCC number PTA-5359), and mAb-467 (ATCC number PTA-5361), and the mAbs were deposited with the American Type Culture Collection Patent Depository on Jul. 30, 2003. Three mAbs (numbers 54, 159 and 174) recognize both reduced HAREs in Western blots. Most of the mAbs raised against the nonreduced 175HARE no longer react with either HARE species after reduction (FIGS. 3 and 4). The exceptions are mAb-159 and mAb-174, which recognize both the 175HARE and 300HARE proteins in Western blots, whether they are reduced (FIG. 4) or nonreduced (FIG. 3). MAb-54 recognizes only the reduced HAREs (FIGS. 3 and 4, lanes 3).

Four of the mAbs also immunoprecipitate both proteins from LEC extracts (FIG. 2). Surprisingly, all mAbs that bind to the 175HARE species, the original antigen, also recognize the 300HARE species. However, as described below, the 300 kDa species is not a dimer of the 175 kDa protein and does not contain a 175 kDa subunit. That eight of eight mAbs raised against the 175HARE cross-react with the 300HARE suggests that the two proteins share one or more common epitopes that may be very antigenic. Except for mAb-159 (IgM) and mAb-30 ($IgG_{2b}$), all of the HARE-specific mAbs are $IgG_1$.

Listed in Table VI are the characteristics of the eight mAbs raised against the rat 175HARE, as described herein before and as will be described in more detail herein after.

Figure 5:
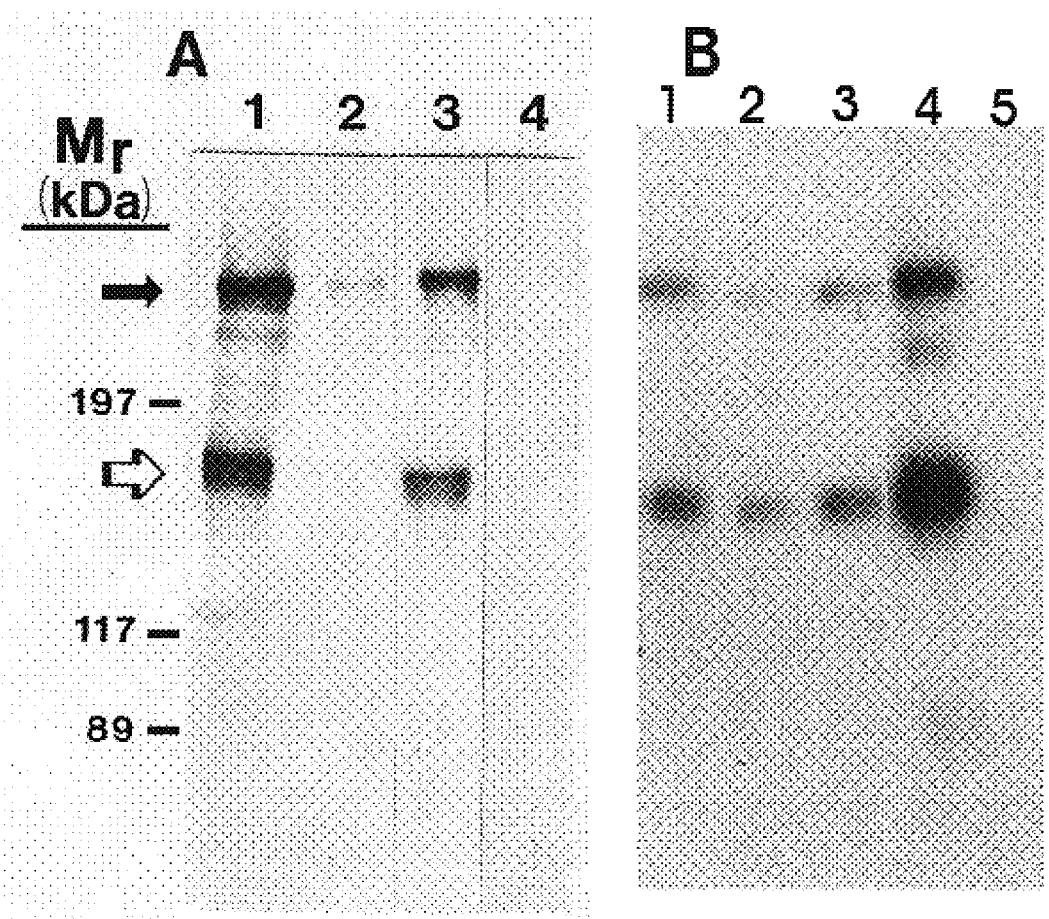
FIG. 5. MAb-30 recognizes the LEC HARE isoreceptors. A, Western blot of LEC membrane extract before (lane 1) and after (lane 2) incubation with the mAb-30 column, the protein eluted from the column (lane 3), and the residual membrane pellet after extraction. The primary antibody was a mixture of five monoclonal antibodies, all of which react with the same two proteins at 175 and 300 kDa. B, in a separate experiment LEC membrane extract was incubated with protein G-Sepharose containing mAb-30 IgG (from ascites) or normal mouse IgG (from serum). HA binding activity was then determined, using SDS-PAGE followed by the ligand blot assay, in untreated extract (lane 1), extract treated with mAb-30 (lane 2) or control IgG (lane 3), or in protein eluted from the mAb-30 IgG (lane 4) or normal mouse IgG (lane 5) resins. The solid and open arrows in this and in FIGS. 6 and 7 indicate the positions of the nonreduced ~300- and 175 kDa HARE proteins respectively, in A and B.
Figure 6:
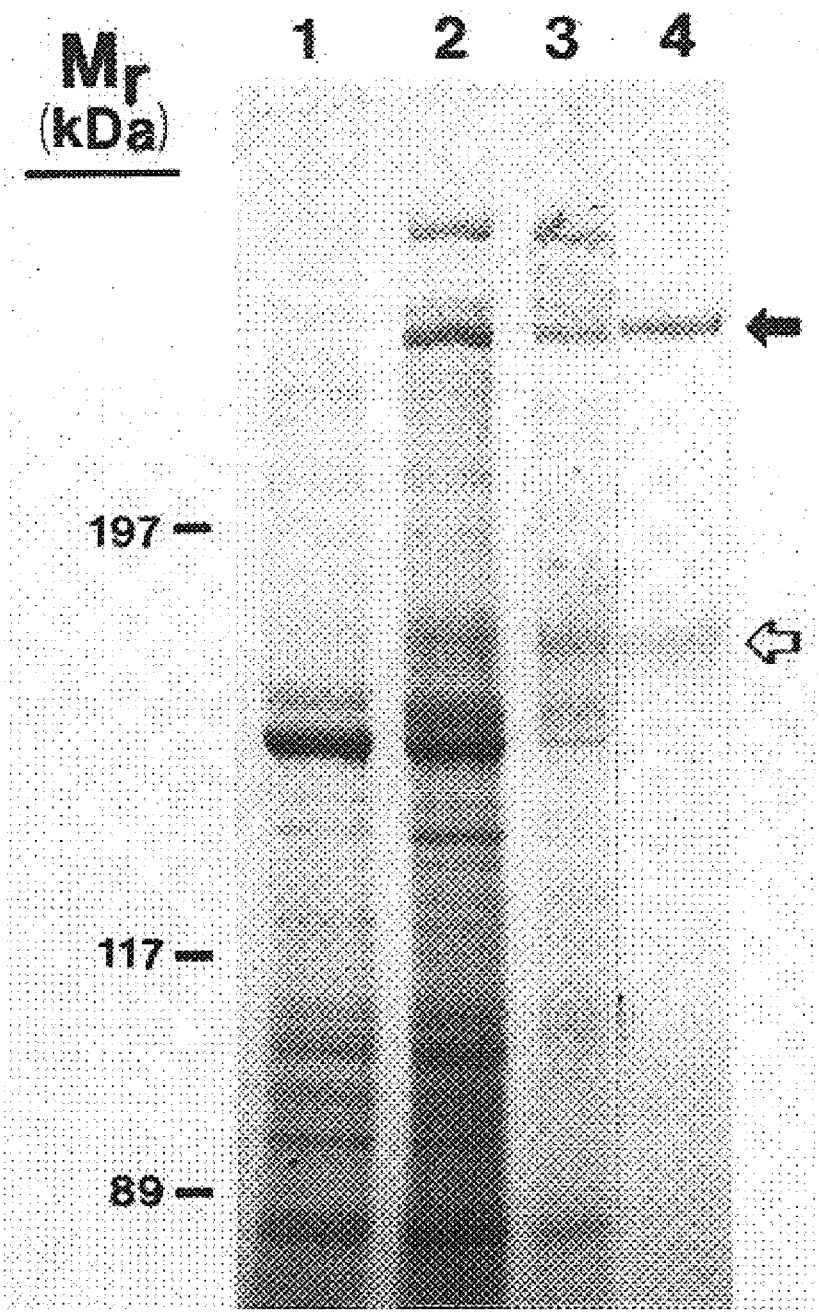
FIG. 6. Immuno-affinity purification of the LEC HARE isoreceptors. HAREs were purified from NONIDET™ P-40 extracts of LEC membranes as described in Materials and Methods. Protein profiles were analyzed by SDS-PAGE and silver staining. Lane 1, run-through from the RCA-I column; lane 2, the starting NONIDET™ P-40 extract of LEC membranes; lane 3, proteins purified from the RCA-I column; lane 4, the purified HAREs eluted from the mAb-30 column.
Figure 7:
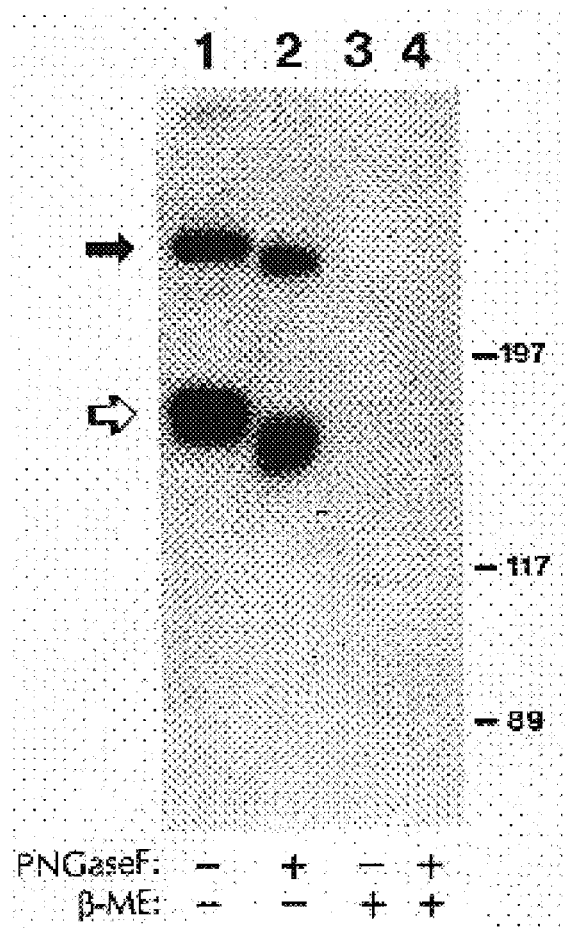
FIG. 7. Effects of reduction and N-Glycosidase F treatment on HA binding activity of the purified 175 kDa HARE and 300 kDa HARE. Purified LEC HARE was reduced and/or N-Glycosidase F-treated and assayed after SDS-PAGE by ligand blotting with $^{125}$I-HA. Both the 175 kDa (open arrow) and the 300 kDa (solid arrow) HARE species are smaller after deglycosylation by 25-30 kDa, but both species are still active (lanes 1 and 2). After reduction neither HARE is able to bind HA (lanes 3 and 4).

Sequential Lectin and Immuno-affinity Chromatography Purifies the Two LEC HARE Species to Homogeneity. Using lectin and mAb-30 affinity chromatography, the two LEC HAREs have been purified to homogeneity and partially characterized (FIGS. 5 and 6). Nonreducing SDS-PAGE analysis indicates that these two proteins comprise more than about 99% of the final purified HARE. The two LEC HAREs remained active, as assessed by the ligand blot assay (FIG. 7, lane 1).

In addition, the 175HARE and 300HARE that are affinity purified by mAb-30 are recognized by the other 7 mAbs. The liver 175HARE and 300HARE are purified in an apparent mole ratio of 2:1. The fraction of total staining in the 175 kDa band was 0.47±0.07 (n=5) and 0.55±0.09 (n=3), respectively, for Coomassie- and silver-stained gels.

Figure 8:
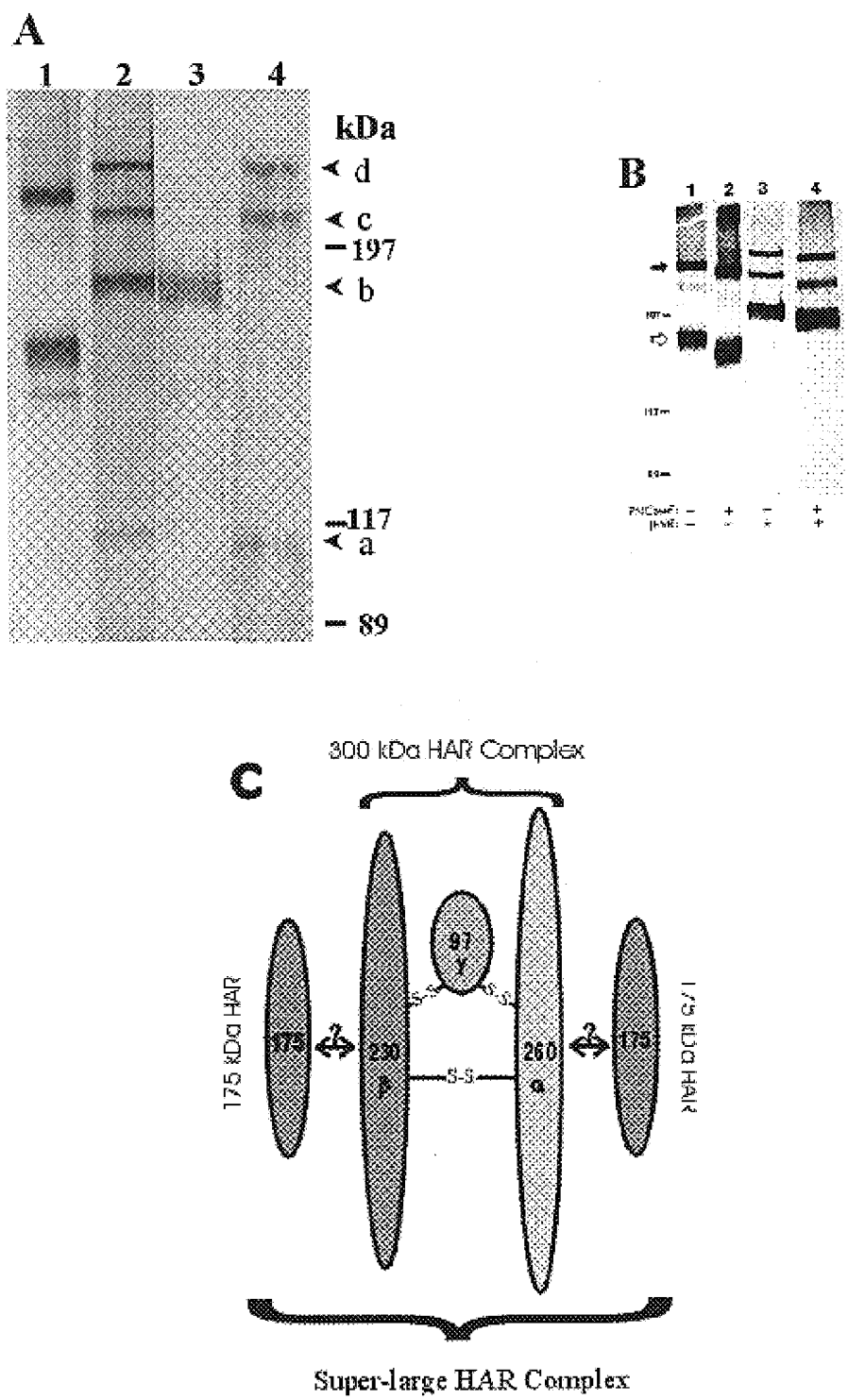
FIGS. 8A and 8B. Effect of reduction or deglycosylation on the reactivity of 175HARE-mAbs with affinity purified HARE. A. The 175HARE and 300HARE proteins were immunoaffinity-purified using mAb-30 as described above and analyzed by SDS-PAGE, without (lane 1) and with (lanes 2, 3 and 4) reduction using β-mercaptoethanol, followed by silver staining. The nonreduced 175HARE and 300HARE bands, separated as in lane 1, were excised, reduced and reanalyzed by SDS-PAGE (lanes 3 and 4). The 175HARE gives a single ~185 kDa species (solid arrowhead b) after reduction (lane 3), whereas the 300HARE gives rise to three subunits, designated α, β, and γ at about 260, 230 and 97 kDa, respectively (lane 4). The 185 kDa protein is not seen in the 300HARE complex. The solid and open arrows indicate the positions of the nonreduced 300HARE and 175HARE, respectively. Panel B shows the reactivity of the HARE proteins, either reduced or treated with N-Glycosidase F as indicated, with a mixture of all eight mAbs (5 µg/ml each) against the 175HARE. After reduction, only the 97 kDa γ subunit of the 300 HARE is not recognized. Nonreduced 300HARE or 175 HARE are indicated by the solid or open arrows, respectively.
FIG. 8C. Model for the organization of the two rat liver HARE isoreceptors. HARE preparations may contain two independent HARE isoreceptors or may be a super-large complex composed of two (or three) copies of the 175HARE protein and one copy of the 300 kDa HARE complex. The 300 kDa HARE is a heterotrimeric complex of three subunits (α, β and γ) that are disulfide bonded.

Subunit Composition of the Two HARE Proteins. To determine if either protein contains disulfide-bonded subunits that are recognized by the mAbs, the 175HARE and 300HARE were analyzed by SDS-PAGE and immunoblotting with or without reduction with β-mercaptoethanol (FIG. 8). The reduced 175HARE yields no other protein species, but the apparent size of the protein increases to about 185 kDa (FIG. 8A, lane 3). This shift to higher $M_r$ is typical of membrane receptors with extracellular domains whose compact or tightly folded structures require intraprotein disulfide bridges.

After reduction, the 300HARE gives rise to three protein species with $M_r$s of 97, 230 and 260 kDa (FIG. 8A, lane 4). None of these three reduced proteins were able to bind $^{125}$I-HA (FIG. 7, lane 3). Based on Coomassie and silver staining and apparent size, the molar ratio of the three protein components of the 300HARE is 1:1:1. The reduced 175HARE protein (at about 185 kDa) and the two large subunits of the 300HARE complex at 260 kDa and 230 kDa are all recognized by the three mAbs that bind the reduced proteins (FIG. 8B, lanes 3 and 4). Interestingly, the 97 kDa subunit of the 300HARE is the only HARE protein not recognized by any of the mAbs raised against the reduced or nonreduced 175HARE.

FIG. 8C illustrates a model for the organization of the two rat liver HARE isoreceptors.

After Deglycosylation With Endo-F, Both HARE Species Still React With The mAbs. During digestion with endo-F, the 175HARE is converted to a single about 150 kDa species, suggesting that up to 10 typical N-linked oligosaccharides may be present. The 300HARE was also reduced in apparent size after enzyme treatment. De-N-glycosylated 175HARE and 300HARE are still able to react with the individual mAbs (not shown) or a mixture of all of the mAbs (FIG. 8B, lanes 2 and 4). Both de-N-glycosylated HAREs are still capable of specific $^{125}$I-HA binding (FIG. 7, lane 2). Therefore, N-linked oligosaccharides do not appear necessary for the HA binding activity of these receptors and do not comprise a part of the epitopes recognized by the mAbs developed here.

Figure 9:
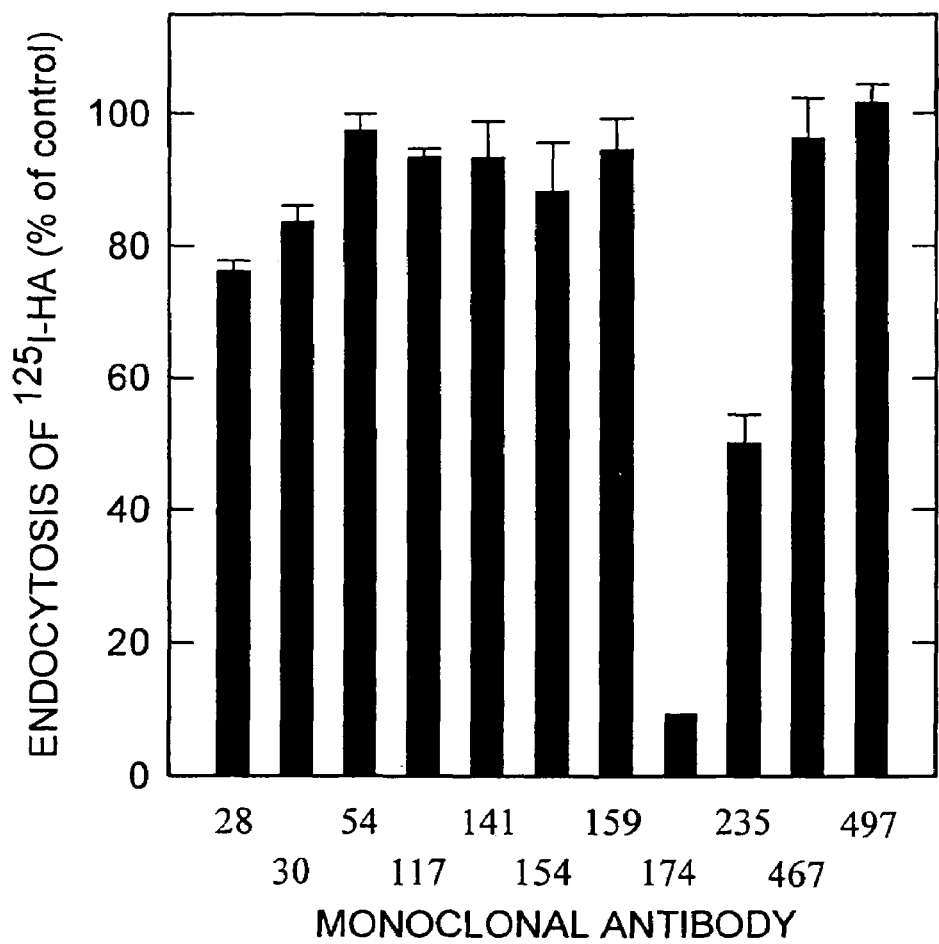
FIG. 9. Endocytosis of HA by LECs at 37° C. is inhibited completely by mAb-174. Cultured primary rat LECs were washed and incubated for 60 min at 37° C. with 2 µg/ml $^{125}$I-HA in MEM medium containing 5 µg/ml of IgG (affinity purified from ascites fluid using Protein G-Sepharose, or rabbit anti-mouse IgM-Sepharose in the case of #159) from each of five different hybridomas against the 175HARE. The plates were then chilled on ice, the media was aspirated, the wells were washed 3 times and the cells were solubilized in 0.3 N NaOH. Radioactivity and protein content were determined for each of the samples. The mean of triplicates ±SD are expressed as percent of control (dpm/mg protein).
Figure 10:
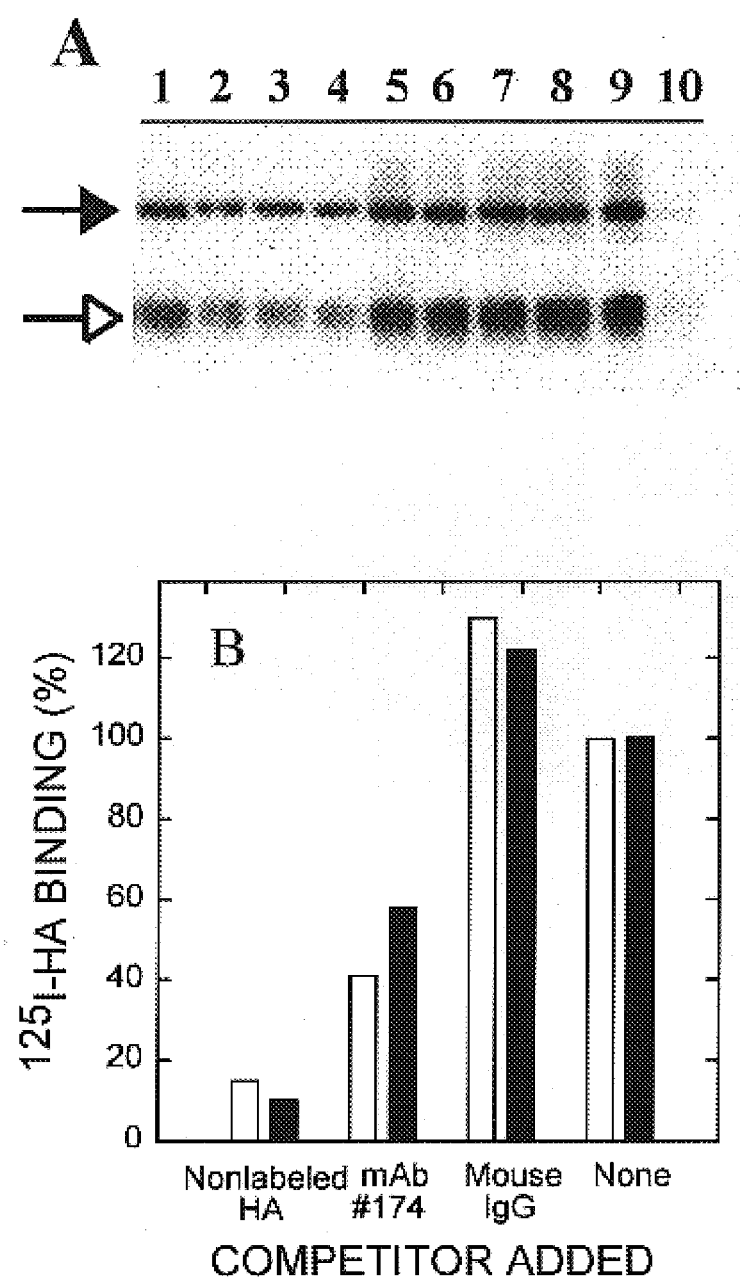
FIG. 10. MAb-174 inhibits $^{125}$I-HA binding to both the 175HARE and 300HARE in the ligand blot assay. A. Affinity purified HARE samples were subjected to SDS-PAGE, electrotransferred to nitrocellulose and blocked as described in Materials and Methods. Nitrocellulose strips were then incubated with TBST containing nothing (lane 9), 50 µg/ml non-labeled HA (lane 10), or 0.5, 1, 5 or 10 µg/ml mAb-174 (in lanes 1-4, respectively) or nonimmune mouse IgG (lanes 5-8 respectively) at room temperature for 90 min. $^{125}$I-HA was then added to a concentration of 0.06 µg/ml and the samples were processed for ligand blot activity and autoradiography. The level of specific binding in the ligand blot assay is >90% (Yannariello-Brown et al., *Biochem. and Biophys. Res. Commun.* 218:314 (1996)). B. The autoradiograph was scanned to quantitate the band densities for $^{125}$I-HA binding with and without excess HA and the values with 5 µg/ml control and mAb-174 IgG.
Figure 11:
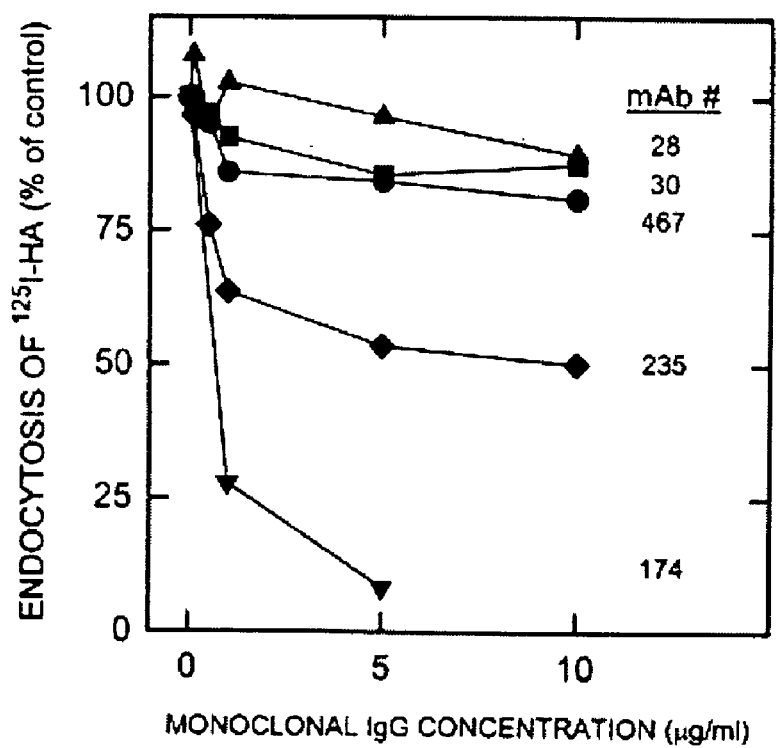
FIG. 11. Antibody inhibition of HA endocytosis by HARE in LECs. Cultured primary rat LECs were washed and incubated for 60 min at 37° C. with 2 µg/ml $^{125}$I-HA in MEM medium containing 0-9 µg/ml of IgG (affinity purified from ascites fluid using Protein G-Sepharose, or rabbit anti-mouse IgM-Sepharose in the case of #159) from each of five different hybridomas against the 175HARE. The plates were then chilled on ice, the media was aspirated, the wells were washed 3 times and the cells were solubilized in 0.3 N NaOH. Radioactivity and protein content were determined for each of the samples. The mean of triplicates ±SD are expressed as percent of control (dpm/mg protein).
Figure 12:
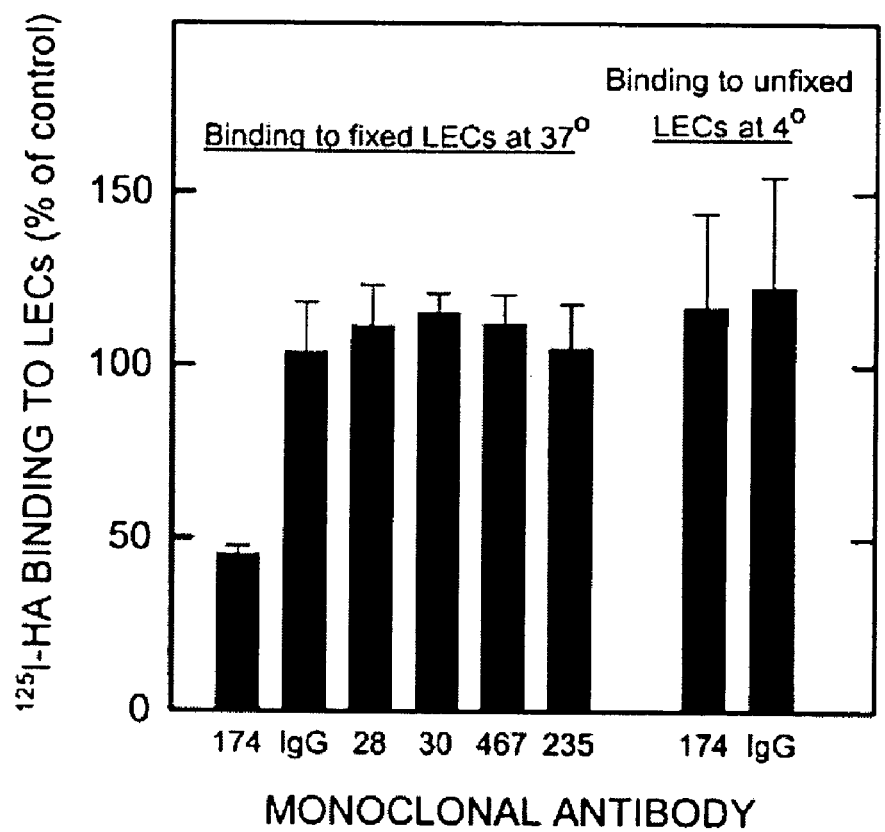
FIG. 12. Antibody inhibition of HA binding to HARE on LECs is temperature dependent. Cultured primary rat LECs were washed and incubated for 60 min at 37° C. or 4° C. with 2 µg/ml $^{125}$I-HA in MEM medium containing 5 µg/ml of IgG (affinity purified from ascites fluid using Protein-G-Sepharose, or rabbit anti-mouse IgM-Sepharose in the case of #159) from each of five different hybridomas against the 175HARE. The plates were then chilled on ice, the media was aspirated, the wells were washed 3 times and the cells were solubilized in 0.3 N NaOH. Radioactivity and protein content were determined for each of the samples. The mean of triplicates ±SD are expressed as percent of control (dpm/mg protein).

MAb-174 Specifically Blocks HA Binding in the Ligand Blot Assay and Blocks the Endocytosis of $^{125}$I-HA by LECs in Culture. Endocytosis and accumulation of $^{125}$I-HA at 37° C. by cultured LECs was completely inhibited by MAb-174 (FIG. 9). Only one other MAb (#235) had any appreciable affect on HA endocytosis, consistently causing partial (about 50%) inhibition of $^{125}$I-HA endocytosis. None of the other anti-175HARE mAbs, nor the three negative control mAbs affected HA uptake (Table VI). These results confirm unequivocally that our eight anti-175HARE mAbs are specific for the bone fide HARE present in LECs. Interestingly, MAb-174 also blocked HA binding to both the 175HARE and 300HARE in the ligand blot assay (FIG. 10A). At 5 μg/ml, MAb-174 blocked about 70% and about 50% of the specific $^{125}$I-HA binding to the 175HARE and 300HARE bands, respectively (FIG. 10B). The same concentration of mouse IgG or the other mAbs showed no inhibition (FIG. 11). Since MAb-174 completely blocks HA uptake by LECs and also recognizes both proteins in Western blots, then both the 175 kDa and 300 kDa proteins could be independent HAREs capable of mediating HA binding and endocytosis. It is important to note that although MAb-174 inhibits $^{125}$I-HA binding and endocytosis by LECs at 37° C., it was unable to block HA binding to live LECs at 4° C. (FIG. 12).

Figure 13:
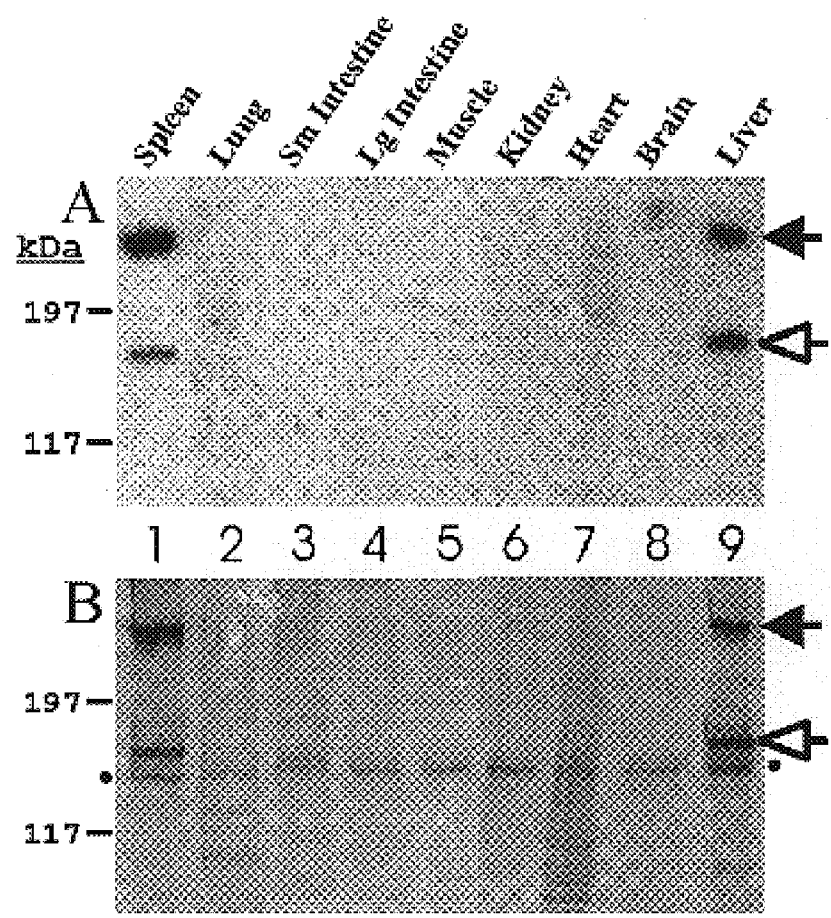
FIG. 13. Western blot analysis of HARE tissue distribution. Crude NP-40 extracts were prepared from homogenates of the indicated rat tissues, and HARE proteins were immunopurified using mAb-235 conjugated to Sepharose. Samples (~100 µg protein) were analyzed by nonreducing SDS-PAGE on a 5% gel, transferred to nitrocellulose membrane, and incubated with $^{125}$I-HA for the ligand blot assay. Autoradiographic analysis (panel A) showed bands at 300 and 175 kDa (solid and open arrows, respectively) in spleen and liver, indicating the presence of both HARE species. After the ligand blot, Western blot analysis was performed on the same membrane (panel B) using a mixture of mAbs 159, 467, 174 and 235 (25 µg/ml ascites). Both HARE bands were present at 300 and 175 kDa in spleen and liver. The nonspecific band (indicated by the solid circles), present in all lanes at ~150 kDa, was due to mouse antibodies coeluted with the HARE during immunopurification.

Tissue Distribution and Immunolocalization of HARE. Western blot analysis of various rat tissues indicated that the 175HARE and 300HARE proteins are highly expressed in spleen as well as liver (FIG. 13B). The other tissues tested (brain, lung, heart, muscle, kidney and intestine) showed no significant reactivity with a mixture of all eight anti-HARE mAbs. As with the liver, each MAb showed the same pattern of reactivity, recognizing both HARE species in the spleen (not shown). Both HARE species isolated from spleen were also active in the $^{125}$I-HA ligand blot assay (FIG. 13A), verifying that these receptors specifically bind HA.

Figure 14:
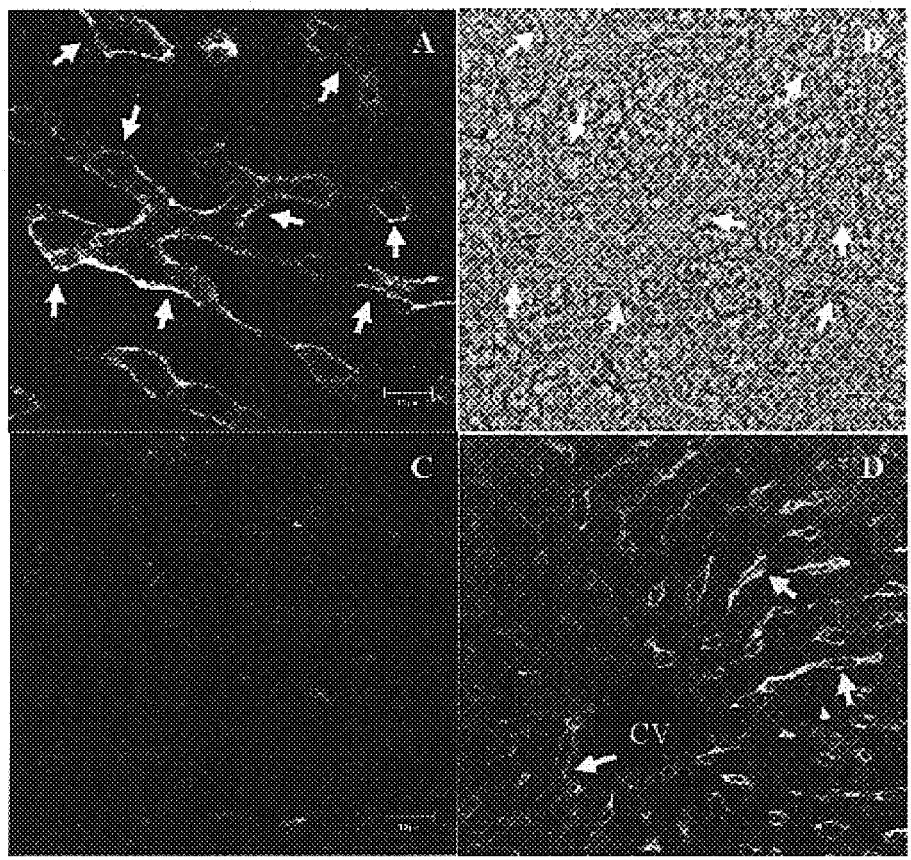
FIG. 14. Confocal immunofluorescent localization of HARE in liver. Rat liver sections were incubated with a mixture of the eight anti-175HARE mAbs (A, B and D) or normal mouse serum (C) and stained with anti-mouse IgG conjugated to Rhodamine Red as described in Materials and Methods. The sections were analyzed by confocal microscopy using Kr lasers (A and C). The phase contrast image in panel B is the same field as shown in panel A (arrows highlight sinusoidal borders). The bars in Panels A-C are 10 µm. Panel D is a nonconfocal fluorescence micrograph at a lower magnification (400×). CV indicates a central vein. Arrowheads indicate sinusoids among columns of hepatocytes.
Figure 15:
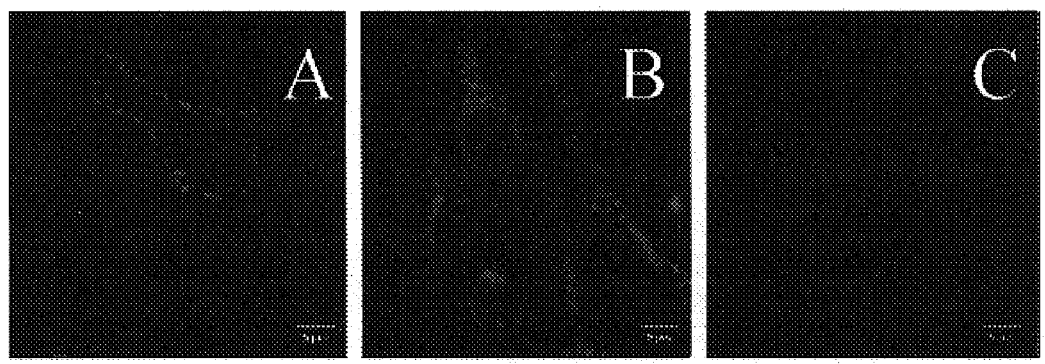
FIG. 15. Immunofluorescent localization of HARE in cultured LECs. LECs cultured overnight on glass coverslips were fixed and treated, as described in Materials and Methods, with (B and C) or without (A) detergent to permeabilize the cells and with ascites from mAb #235 (A and B) or normal mouse serum (C) and stained with goat anti-mouse IgG conjugated to rhodamine red. The bar represents 5 µm.
Figure 16:
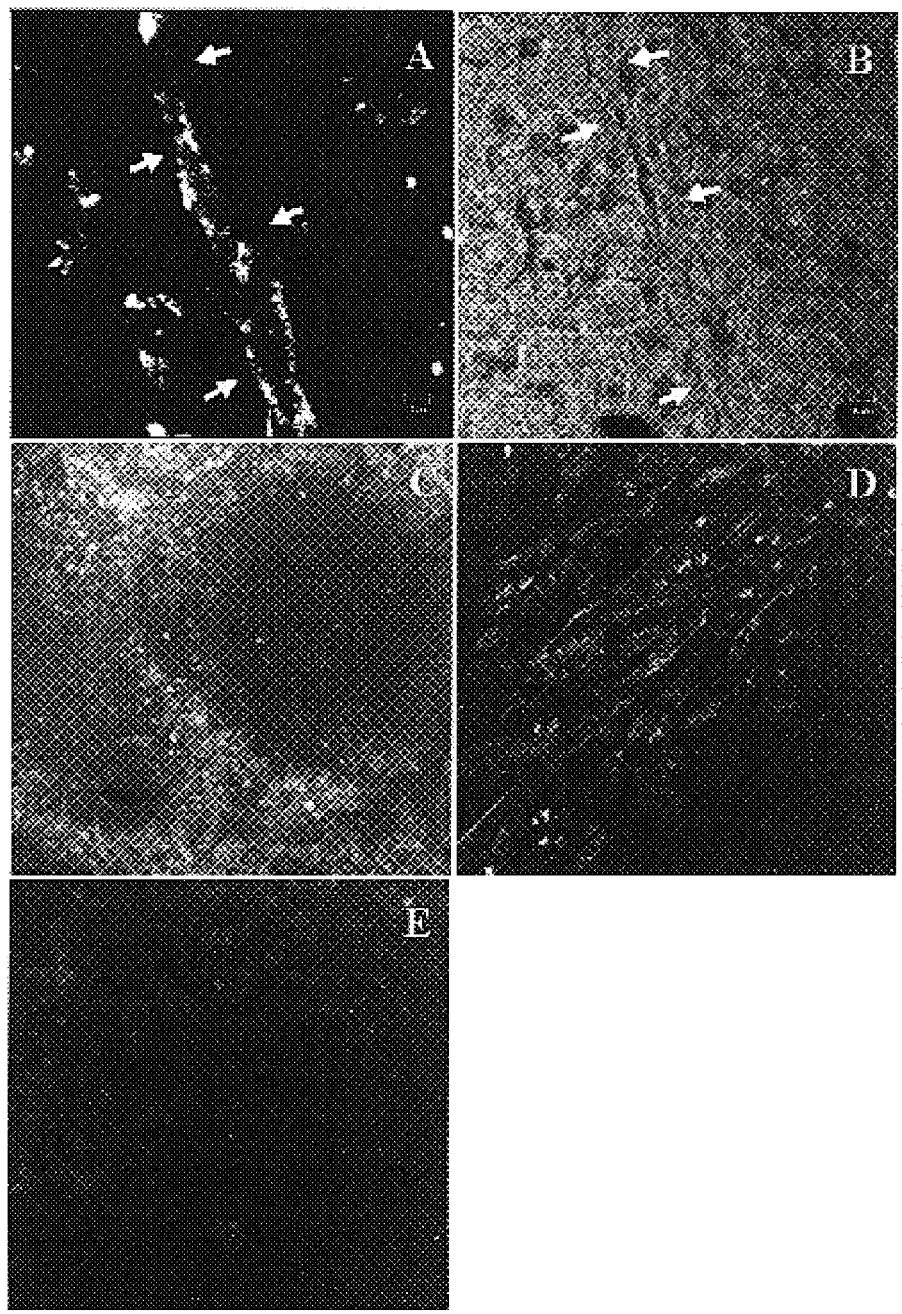
FIG. 16. Immunofluorescent localization of HARE in spleen. Sections of rat spleen were incubated with a mixture of eight anti-175HARE mAbs (A, B, C and D) or normal mouse serum (E), washed and stained with goat anti-mouse IgG conjugated to Rhodamine Red. The confocal fluorescent and phase contrast images, respectively in A and B, show the same field. The bars in Panels A and B are 10 µm. The arrows indicate sinuses lined with positive cells. Panels C, D and E were viewed by normal fluorescence microscopy at magnifications of 200×, 400× and 400×, respectively. The splenic nodules (dark circular zones in C) were unstained.
Figure 17:
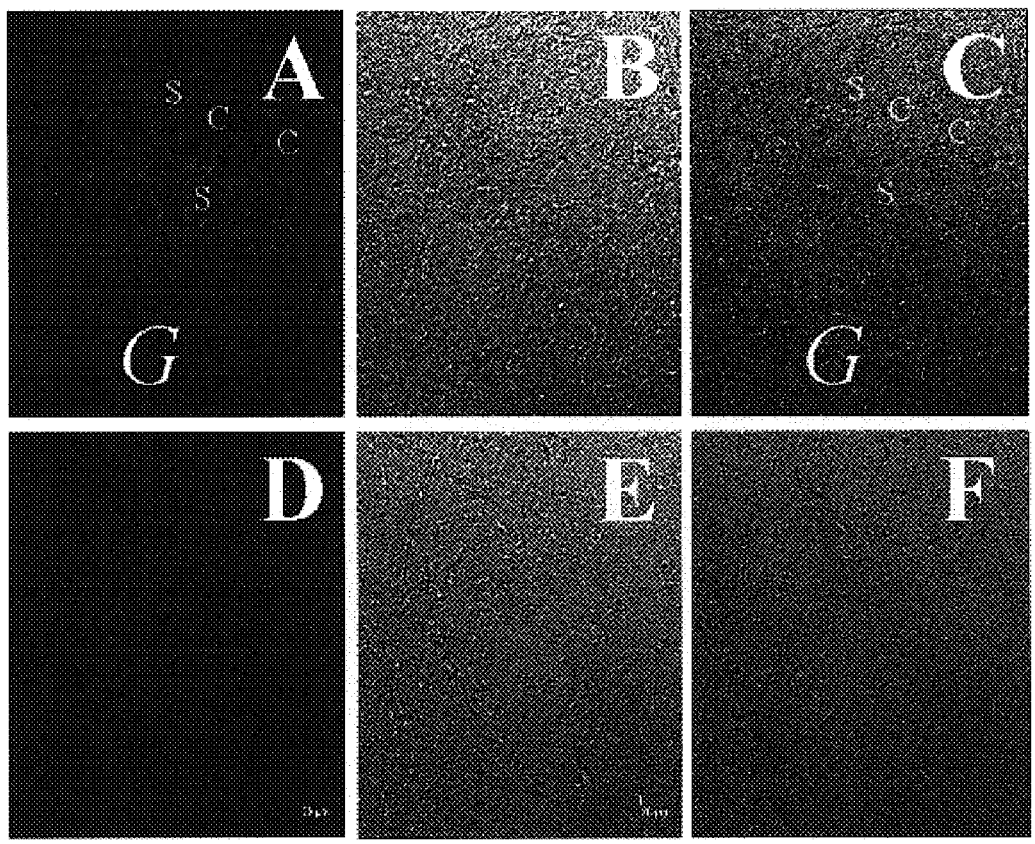
FIG. 17. Immunofluorescent localization of HARE in lymph node. Sections of rat mesenteric lymph node were incubated with a mixture of eight anti-175HARE mAbs (A, B and C) or normal mouse serum (D, E and F), washed and stained with goat anti-mouse IgG conjugated to Rhodamine Red. The sections were analyzed by confocal fluorescence microscopy (A and D) or phase contrast microscopy (B and E), and the two images were overlaid (C and F). The bar is 20 µm.
Figure 18:
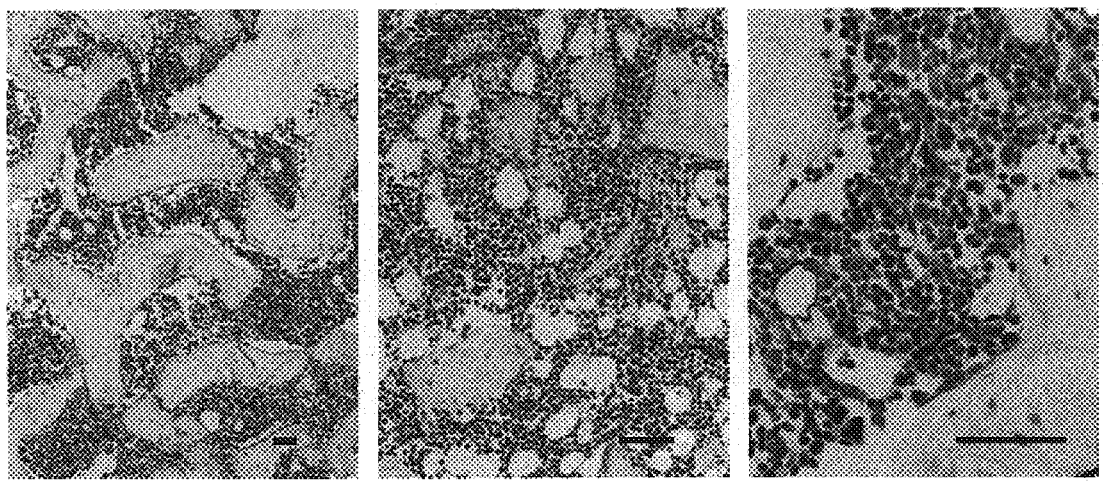
FIG. 18. Immunofluorescent localization of HARE in bone marrow. Rat bone marrow tissue was processed and sections were stained with a mixture of mAbs against the rat 175 kDa HARE (left and right panels) or mouse serum as a control (middle panel) as described in Materials and Methods. Two different magnifications of the mAb-treated samples are shown to illustrate the positive staining of cells lining the sinusoidal regions of the marrow.

Confocal indirect immunofluorescence demonstrated that the HARE proteins are localized to the sinusoids in the liver (FIG. 14) as expected. No staining was observed in the parenchymal cells. Confirming this cellular distribution, the protein is not expressed in isolated hepatocytes in culture (not shown), but is strongly expressed in purified, cultured LECs (FIG. 15). HARE is present in LECs in a pattern typical for an endocytic, recycling receptor (Mellman, *Annu. Rev. Cell Biol.* 12:575 (1996)); it is at the cell surface, in pericellular vesicles (presumably endosomes) and ER and Golgi. In rat spleen, the HARE proteins are present in the venous sinuses of the red pulp (FIG. 16A-D). No significant staining was observed in the germinal centers or white pulp of the splenic nodules. In rat lymph nodes, HARE is localized to the medullary sinuses (FIG. 17A-C). It is not present in the spheroid nodules or their germinal centers. Vascular endothelial cells were not stained in any of the tissues examined.

Figure 20:
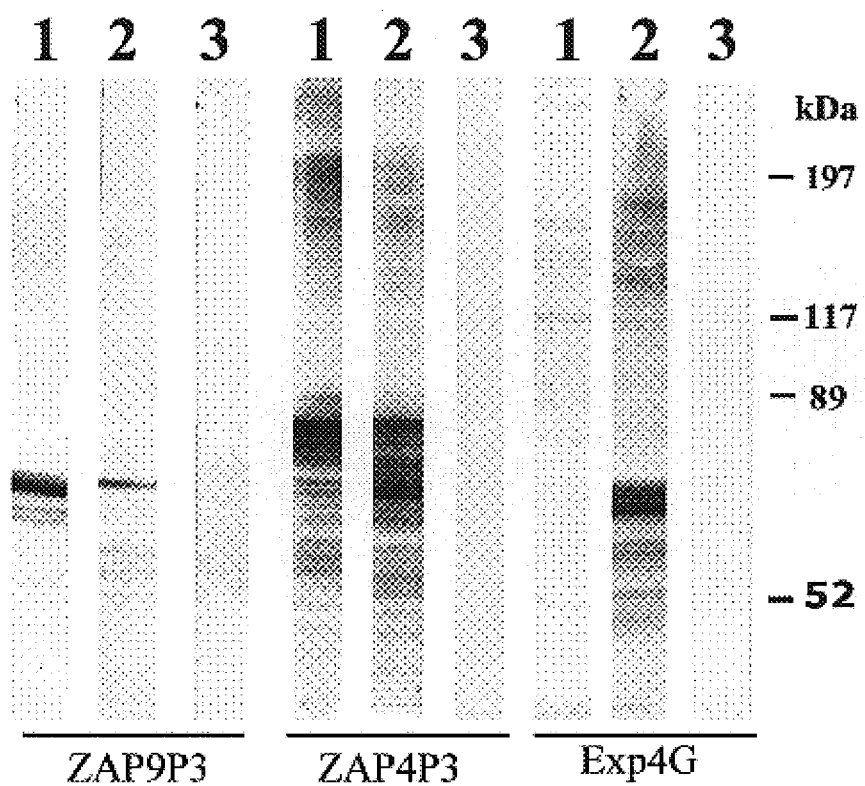
FIG. 20. Recognition of partial HARE cDNA clones by anti-HARE mAbs. RT-PCR products cloned into the TA™ vector were amplified and used to screen the LEC cDNA library in λ-ZAP EXPRESS™. The positive bacteriophages (ZAP9P3 and ZAP4P3) were excised in vivo into PBK-CMV phagemid. The Exp4G clone was isolated by RT-PCR using primer pair 208F (SEQ ID NO:3) and GSP-GT81R (SEQ ID NO:4) (Table II), based on sequenced peptides, and cloned into the pTrcHis2 expression vector using the TA CLONING™ kit. The three vectors were transformed into TOP10F' or XLOLR cells, grown to an $A_{600}$ of ~0.8, and the fusion proteins were induced with 1 mM IPTG. After 2 h, the cells were collected, solubilized in 1×SDS-PAGE sample buffer, and then subjected to SDS-PAGE, electrotransfer to nitrocellulose and Western blot analysis using anti-175 kDa HARE mAb-159 (lanes 1), mAb-174 (lanes 2) or normal mouse serum (lanes 3), as a control, as described in Materials and Methods. The predicted sizes of the, protein fragments encoded by the partial cDNAs of ZAP9P3, ZAP4P3 and Exp4G are, respectively, 57 kDa, 60 kDa and 66 kDa.
Figure 21:
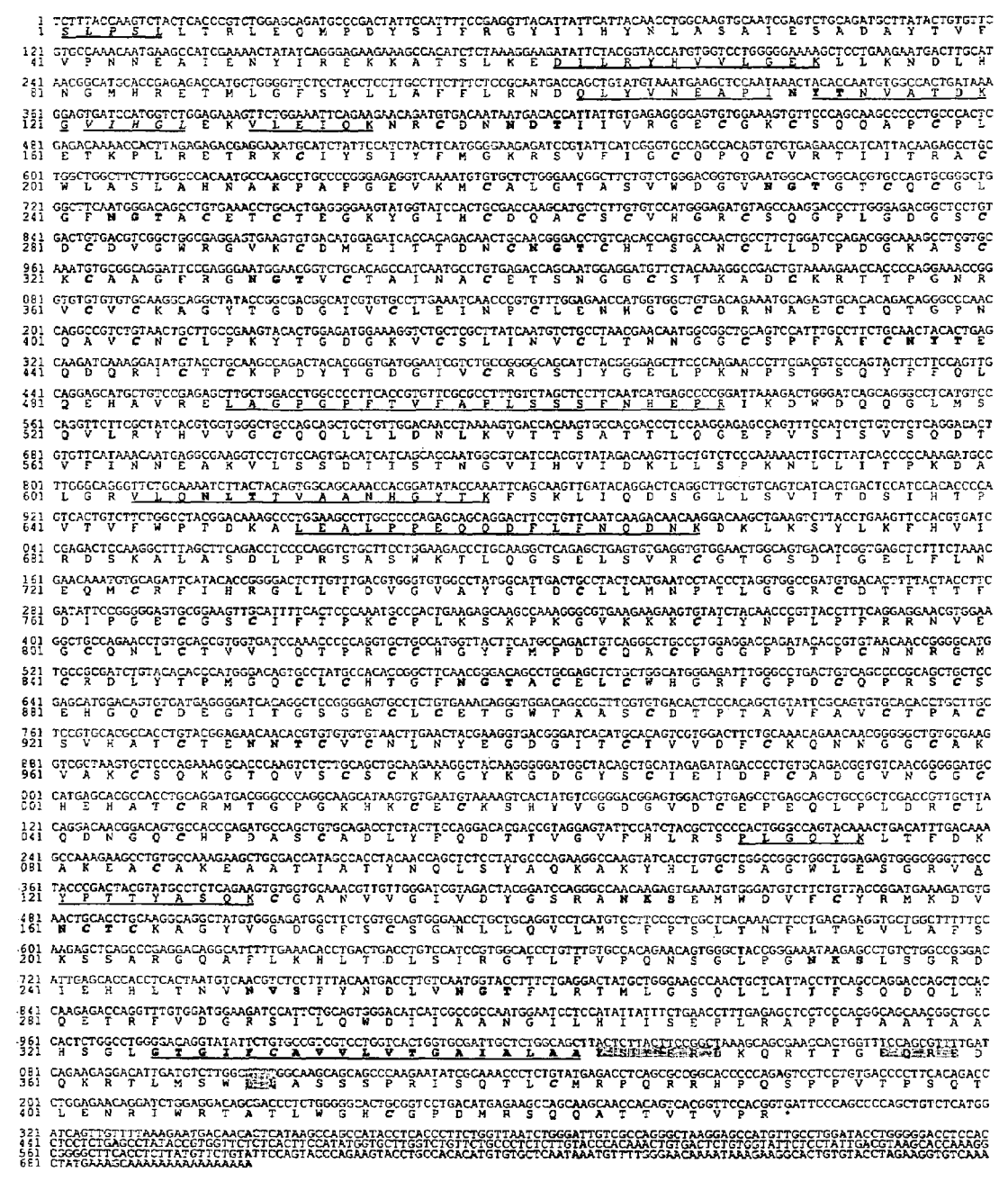

Assembly of the rat 175 kDa HARE cDNA. The immuno-affinity purified 175 kDa HARE was reduced, resolved by SDS-PAGE, excised and subjected to internal tryptic peptide analysis (Table II). Based on amino acid sequence of the resulting peptides and subsequent RT-PCR analysis, PCR fragments were cloned and used as probes to screen a custom-made λZAP EXPRESS™ rat LEC cDNA library. Overlapping clones of various types were then used to assemble a partial cDNA (FIG. 19) that encoded the peptides identified from the purified 175 kDa HARE (Table II). To verify the fidelity of key partial cDNA clones isolated from the library or by RT-PCR, we verified that these clones resulted in the expression, in transformed bacteria, of protein fragments that were recognized in Western analysis by one or more of the eight mAbs raised against the 175 kDa HARE (FIG. 20). For example, clones ZAP9P3 and ZAP4P3 showed reactive bands at 68 kDa and 72 kDa, respectively, with MAb-159 and MAb-174. The major proteins expressed in these three cases migrated in SDS-PAGE as though they were ~20% larger, which is also a characteristic of full length HARE. The cDNA assembled from the various positive clones, however, lacked 5' upstream noncoding sequences, an initiating codon and a leader sequence for appropriate membrane insertion. When this partial cDNA was extended further by 5'RACE analysis, the resulting coding region was longer than anticipated for encoding a glycoprotein of 185 kDa, which is the size of the 175 kDa HARE when reduced. The purified 175 kDa HARE is a broad, rather than well focused, band in SDS-PAGE, suggesting that it contains species of heterogeneous size. Although some size heterogeneity is expected because each, HARE isoreceptor is a glycoprotein with about 25 kDa of N-linked oligosaccharides, another reason could be that the purified protein was either randomly or specifically cleaved by proteases. To test this latter hypothesis NH$_2$-terminal sequence analysis on the affinity purified 175 kDa HARE was performed, and two termini corresponding to regions of the encoded deduced protein that were 122 amino acids apart (Table II and FIG. 21) were discovered. Previous similar NH$_2$-terminal sequencing attempts, before having the partial cDNA sequence, had not yielded interpretable data because the yields were relatively low and a unique sequence was not obtained. Knowing the deduced protein sequence, however, enabled us to identify a major and a minor NH$_2$-terminal sequence beginning at amino acid 1 (SLPSL . . . ) and 122 (VIHGL . . . ), respectively.

Figure 22:
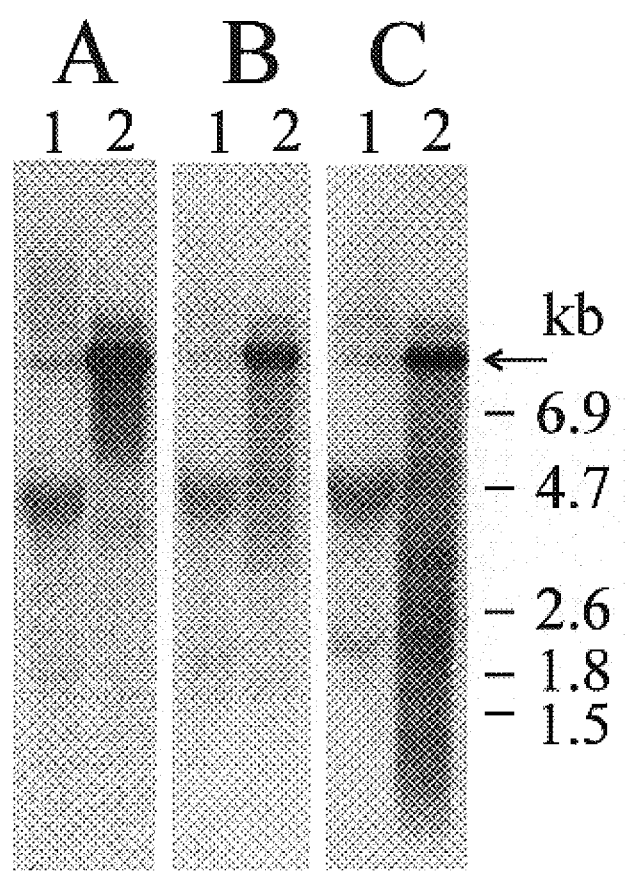
FIG. 22. Northern blot analysis of rat LEC RNA with 175 kDa HARE cDNA probes. Total RNA (lanes 1) or mRNA (lanes 2) samples prepared from isolated rat LECs were subjected to formamide-gel electrophoresis, transfer to nylon membranes and processing as described in Materials and Methods. The membranes were allowed to hybridize with each of three different $^{32}$P-labeled DNA probes (see FIG. 19), 5'RACE #11 (A), ZAP1P3 (B) or ZAP9P3 (C), which are located at the 5'-end, the middle, and the 3'-end of the 175 kDa HARE cDNA sequence, respectively.

The above results on the origin of the 175 kDa HARE protein and the structure of the isolated cDNA led us to consider that there was no mRNA species directly encoding the protein, but rather that it was encoded by a much larger mRNA for the 300 kDa HARE, whose protein product was then proteolytically processed to the 175 kDa HARE. Consistent with this interpretation, Northern analysis, using mRNA from rat LECs and probes from either the 5' end, the middle or the 3' end of the cDNA, revealed a major ~10 kb band (FIG. 22). We did not observe a separate mRNA species in the range of ~6 kb to 7 kb, which might be the expected size if the 175 kDa HARE were encoded directly.

Figure 23:
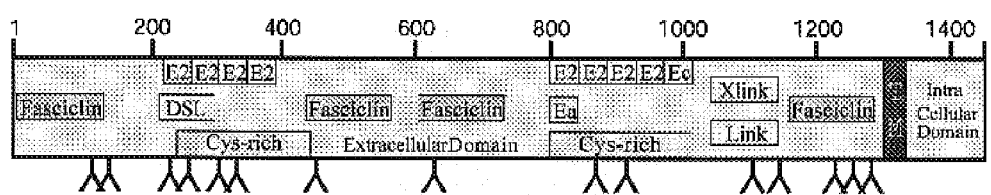
FIG. 23. Domain structure of the 175 kDa rat HARE protein. The scheme depicts the organization of multiple protein domains, within the 1431 amino acid HARE protein, that are identified by numerous predictive search programs such as SMART (71), CD-Search, and other sites linked to ExPASy or NCBI. TM indicates the transmembrane domain; E2, Ea and Ec represent, respectively EGF-2, lamin-like EGF and EGF-Ca$^{+2}$ domains; potential N-linked glycosylation sites are indicated by the Y symbols.

Domain structure and characteristics of the deduced 175 kDa HARE. The cDNA sequence (SEQ ID NO:1) presented in FIG. 21 encodes a 1431 amino acid protein (SEQ ID NO:2) that starts with the serine residue identified as the major $NH_2$-terminus. The deduced protein contains all five internal peptides found in an affinity purified 175 kDa HARE protein preparation as well as three additional internal peptides found in a partially purified HARE preparation (Table II). The protein is predicted to be a type I membrane protein (FIG. 23), with a large $NH_2$-terminal extracellular domain (1322-1324 residues depending on the particular prediction program used), a single transmembrane domain ($\sim L^{1323}$-$A^{1343}$), and a small COOH-terminal cytoplasmic domain (~88 amino acids). As is the case for many proteins, the exact boundaries predicted for the transmembrane domain of HARE are somewhat uncertain; they vary by 2-3 amino acids on both sides of the predicted domain depending on the particular algorithm used. For example, the programs TMPred, TMHMM and PSORTII, respectively, predict a transmembrane domain between residues 1327-1347, 1325-1347 and 1327-1343. The predicted mass of the protein is 156,002 Da, and the predicted isoelectric point is pH 7.49. The ectodomain contains 15 putative N-glycosylation sites (excluding one NPS sequon), and two cysteine-rich regions. The extracellular domain has multiple motifs and subdomains with homology to similar regions identified in other receptors and matrix molecules. Multiple EGF-like, βIgH3, and Fasciclin domains, as well as one DSL domain, are also organized throughout the extracellular domain of the 175 kDa HARE. In addition, a 93 amino acid region near the membrane junction ($Gly^{1063}$-$Arg^{1156}$) is homologous to the mammalian proteoglycan extracellular Xlink domain and the HA-binding domain of the link protein.

Figure 24:
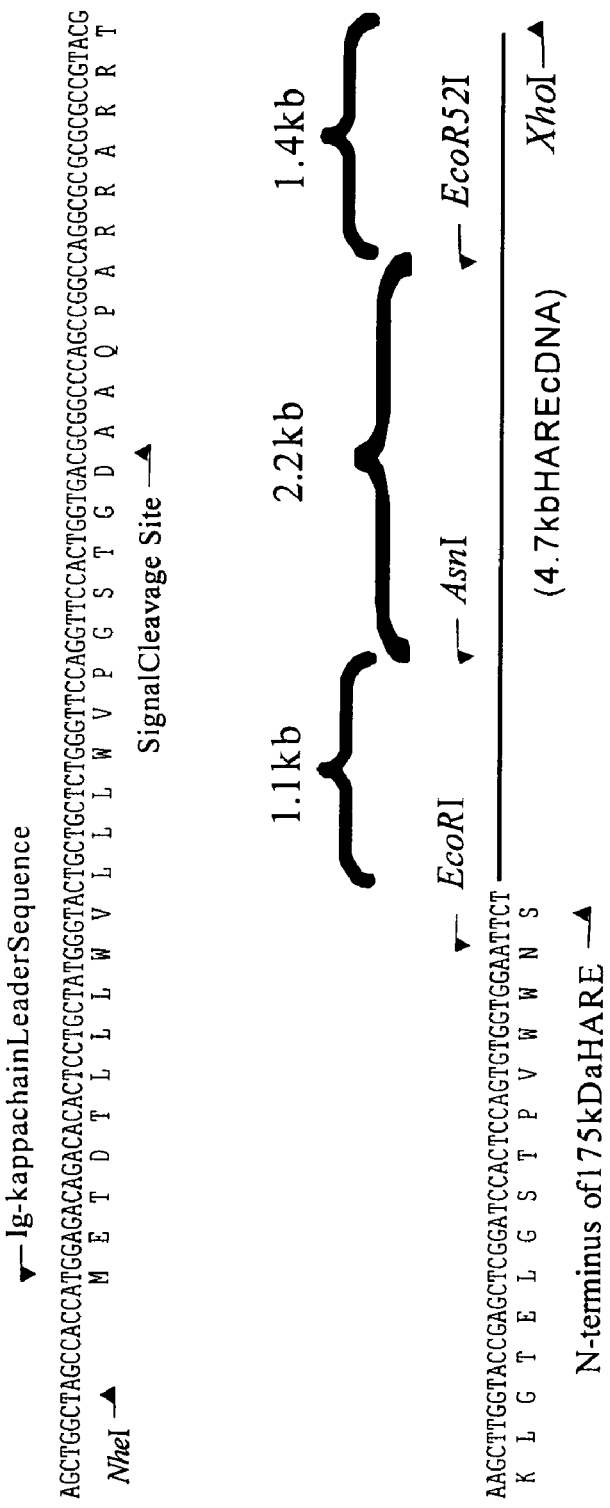
FIG. 24. Schematic map of the recombinant 175 kDa rat HARE construct. A 5'-end fragment (1.1 kb) of the 175 kDa HARE open reading frame was amplified by RT-PCR using primers containing EcoRI sites, and cloned into pSecTag2 vector, which contains an Ig k-chain leader sequence. The DNA insert was cut with NheI and AsnI, and then cloned into pcDNA3.1 together with two other 175 kDa HARE cDNA fragments of 2.2 kb and 1.4 kb, which were derived from the RT-PCR and cDNA library screenings, respectively, and which encode the remainder of the 175 kDa HARE protein. The fragments were digested with different restriction enzymes as indicated and assembled as described in Materials and Methods.
Figure 26:
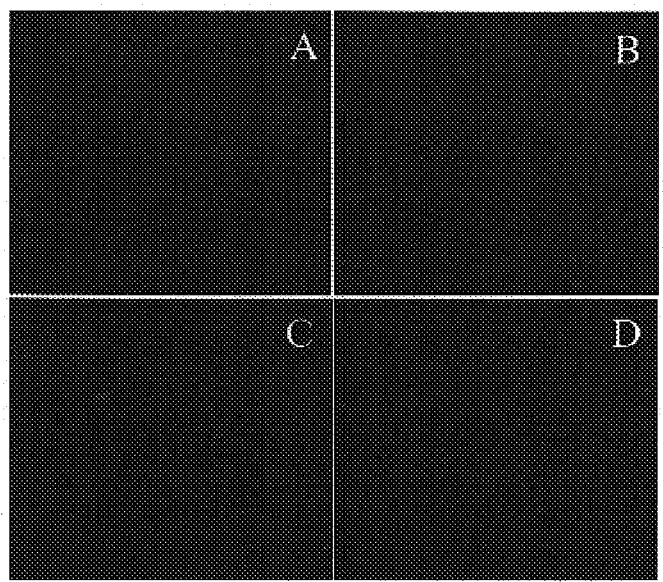
FIG. 26. Indirect confocal immunofluorescence staining of the 175 kDa HARE in stably transfected SK-Hep-1 cells. The stably transfected SK-Hep-1 cell line SK-175HARE-36 was cultured overnight in a tissue culture chamber/slide, and then fixed and incubated with (C and D) or without (A and B) 0.1% Triton X-100 to permeabilize the cells. The cells were stained with normal mouse serum (B and D) or a mixture of eight mAbs raised against the rat 175 kDa HARE (A and C).
Figure 27A:
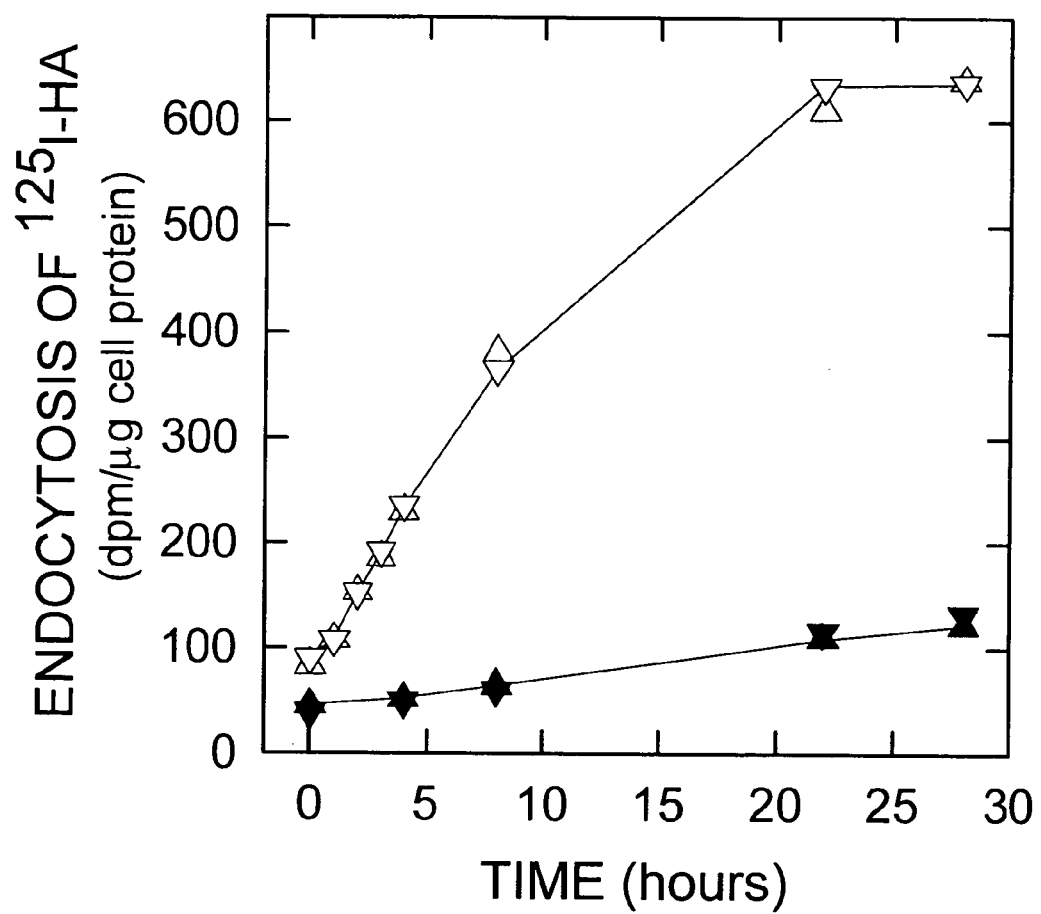
FIG. 27A. Endocytosis of $^{125}$I-HA by SK-Hep-1 cells expressing the 175 kDa HARE. Two independent stably transfected clones expressing the 175 kDa HARE, SK-175HARE #27 (▲,Δ) and SK-175HARE #36 (▼,∇) were cultured in 4-well tissue culture plates. The cells were washed and incubated at 37° C. in fresh culture media without fetal calf serum for 1 hr. The plates were then placed on ice and the cells washed 2 times with 1 ml of HANKS. Medium containing 2 µg/ml $^{125}$I-HA with (▲,▼) or without (Δ,∇) 200 µg/ml unlabelled HA was added to each well. Cells were allowed to bind ligand on ice for 60 min for the surface binding values or they were allowed to internalize ligand at 37° C. At the noted times, the medium was aspirated, and the cells were washed 3 times with 1 ml HANKS. The cells were lysed in 0.3N NaOH, and radioactivity and protein were determined.
Figure 27B:
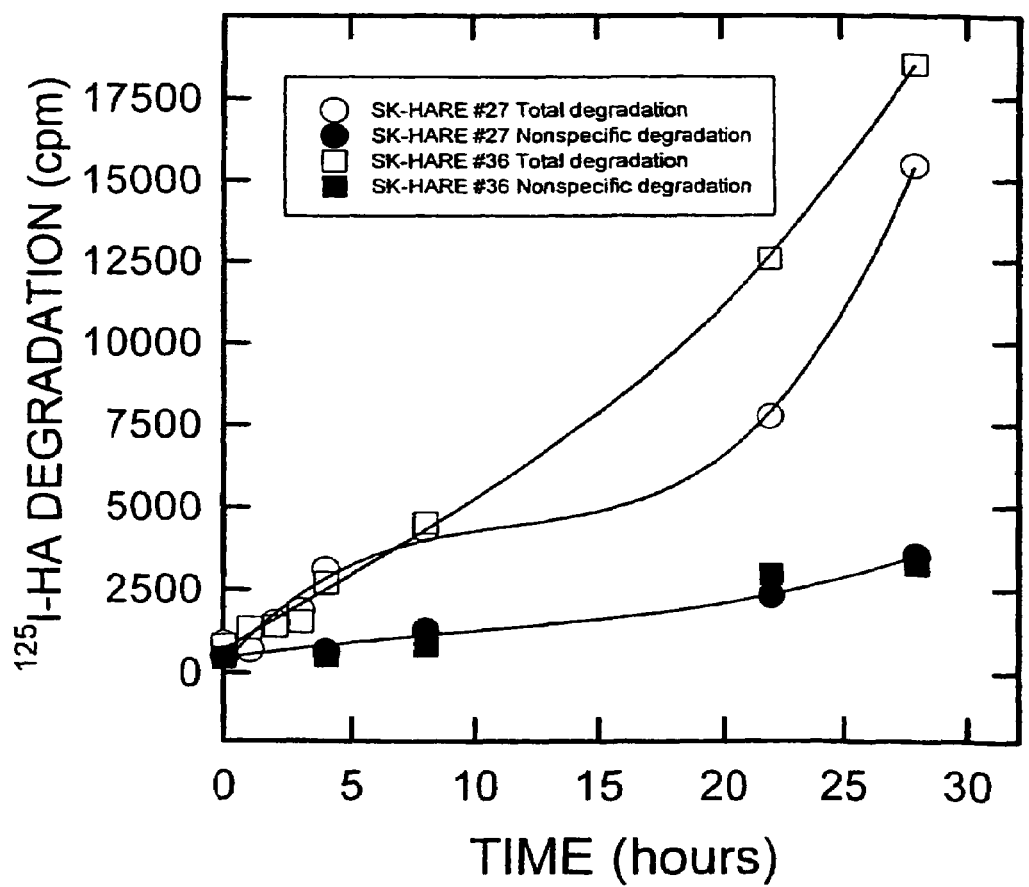
FIG. 27B. Degradation of internalized HA by transfected SK-Hep1 cell lines expressing the 175 kDa HARE. The indicated clones were incubated with $^{125}$I-HA as described above in the presence (closed symbols) or absence (open symbols) of a large excess of nonlabeled HA to assess nonspecificity. Degradation was assessed using a CPC precipitation assay.
Figure 27C:
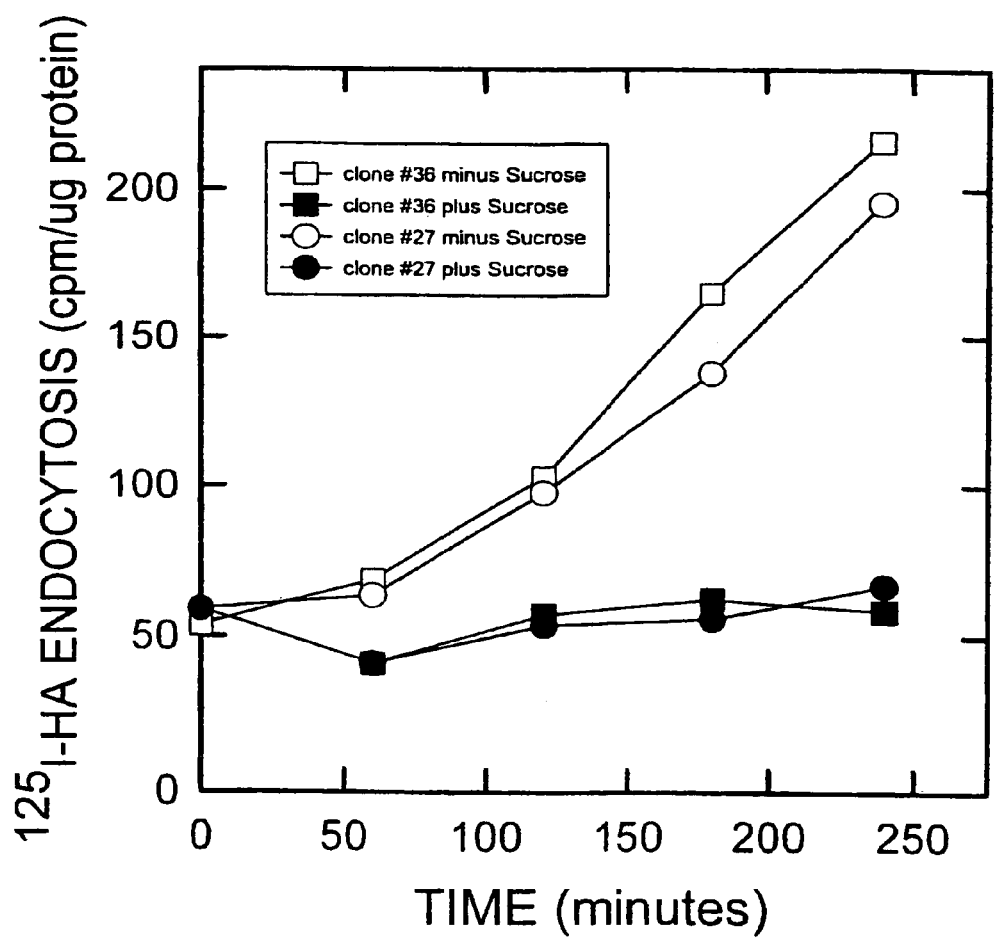
FIG. 27C. Hyperosmolarity inhibits $^{125}$I-HA endocytosis mediated by HARE in transfected SK-Hep1 cells. Cells grown up from two independent SK-Hep1 transfected clones (#27 and #36) were allowed to internalize $^{125}$I-HA as described above either in the presence (closed symbols) or absence (open symbols) of 0.4 M sucrose added to the medium. These hyperosmolar conditions disrupt clathrin assembly and the coated pit pathway, thus inhibiting endocytosis of HA by LECs. The inhibition of HA uptake in the stable SK-Hep1 cell lines expressing HARE demonstrates that this recombinant receptor mediates HA uptake via a coated pit endocytic pathway as expected.
Figure 27D:
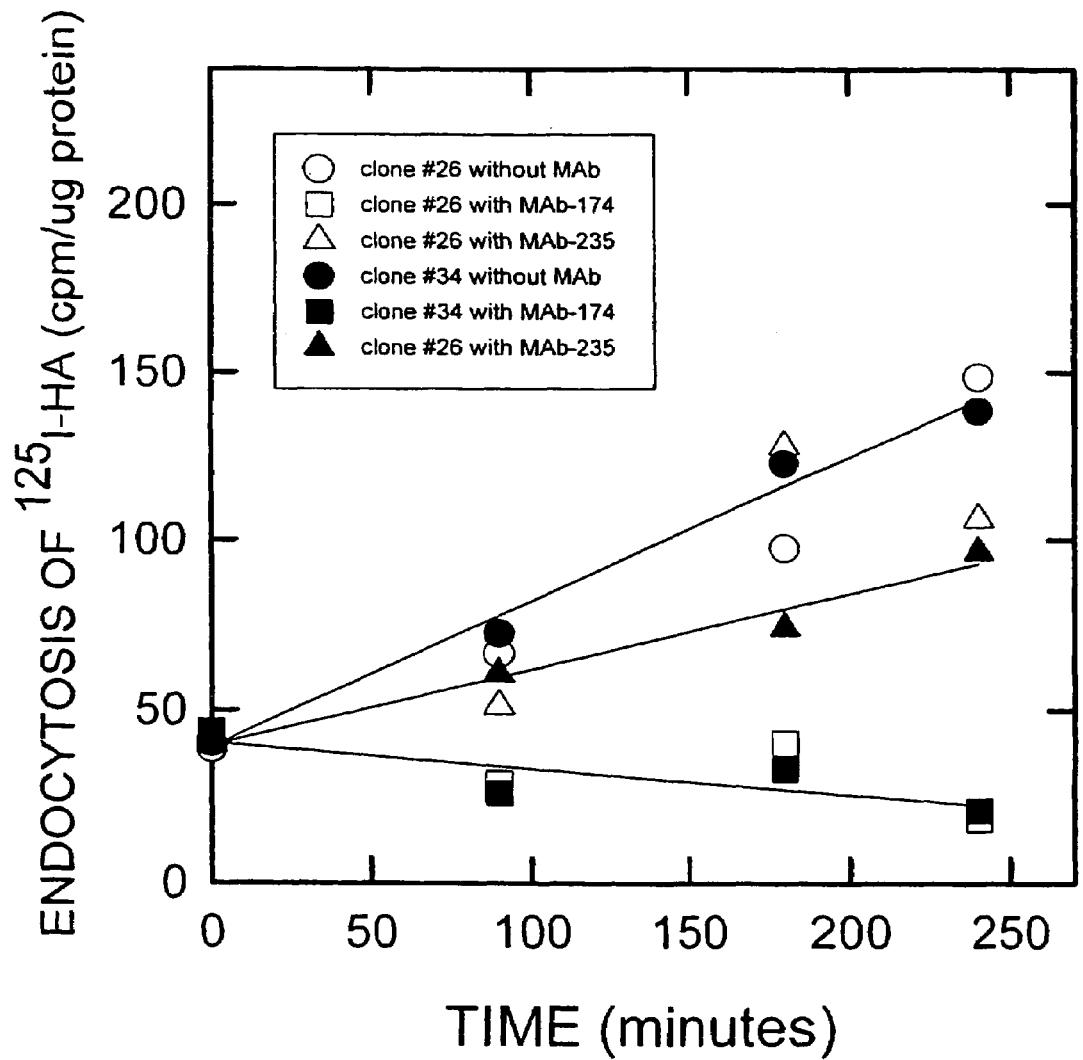
FIG. 27D. Specific monoclonal antibodies against HARE inhibit HA endocytosis in SK-Hep1 transfectants expressing the 175 kDa HARE. The indicated SK-Hep1 clones expressing the 175 kDa HARE were allowed to internalize $^{125}$I-HA as described above with no addition or in the presence of either mAb-174 or mAb-235 as indicated.

Expression of a functional HA Receptor for Endocytosis from the 175 kDa HARE cDNA. To verify that we have cloned a bone fide cDNA for the 175 kDa HARE, we performed binding and internalization studies using COS-7 or SK-Hep-1 cells transfected with HARE to show they express an endocytic receptor for HA. Since there is no natural mRNA for the protein, we constructed an artificial cDNA that encodes the ORF for the 175 kDa HARE fused at the 5' end to a short region of the Ig k-light chain sequence encoding a start codon and a membrane insertion signal or leader sequence (FIG. 24). When transiently transfected into COS 7 cells, this cDNA gave expression of a protein of the expected size that was recognized in Western blots by all the specific anti-HARE mAbs and that bound $^{125}$I-HA specifically in a ligand blot assay (FIG. 25). We then used the same vector to generate stable cell lines expressing HARE after antibiotic selection of transfected SK-Hep1 cells. This cell line was chosen because it does not express any detectable endogenous HA receptors capable of specific $^{125}$I-HA binding or endocytosis, does not show reactivity with the anti-HARE mAbs and has been used by us and others for similar studies. Six independent clones were selected, all of which had essentially identical characteristics with respect to 175 kDa HARE expression and function. Indirect immunofluorescence (FIG. 26) showed that the protein was localized to the cell surface as well as in intracellular compartments typical for an endocytic, recycling receptor (Mellman, *Annu. Rev. Cell Biol.* 12:575 (1996)). For example, it appears in the pericellular region, presumably in endosomes and in the pericellular region, in the ER and Golgi. Finally, the stable cell lines expressing HARE were able to mediate the specific and continuous endocytosis of $^{125}$I-HA for many hours at 37° C. (FIG. 27). Specific HA uptake, assessed by competition with non-labeled HA, was ~90% and these cells internalized at least four-times their number of surface HA receptors. There was no indication of HARE protein degradation during this period, indicating that the recombinant 175 kDa HARE is a recycling endocytic receptor, as expected. SK-Hep1 cells, transfected with the same vector containing an unrelated cDNA insert or untransfected cells, displayed the same level of nonspecific $^{125}$I-HA uptake at 37° C. as in FIG. 27A. Results from other studies demonstrate that HA endocytosis mediated by HARE in these stable cell lines leads to degradation of the internalized HA (FIG. 27B), uptake is completely sensitive to hyperosmolarity (FIG. 27C), which disrupts clathrin recycling and coated pit formation (Oka and Weigel, *J. Cell Biochem.* 36:169 (1988); Oka et al, *J. Biol. Chem.* 264:12016 (1989)), and uptake is completely blocked by mAb-174 (FIG. 27D), which inhibits $^{125}$I-HA uptake in LECs as described herein before.

The 175 kDa HARE is related to a protein family of unknown function. The domain organization of HARE is very different from that of all the other known HA-binding proteins or HA receptors including ICAM-1, RHAMM (also recently designated CD168), CD44, TSG-6, Link protein and LYVE-1. We and others have noted the presence, in various genomic and EST databases, of protein sequences with significant homology to several known HA-binding proteins. For example, a group of three ORFs were reported to encode HA-binding proteins based on the fact that the deduced protein sequences contained a Link-like domain with homology to the Link protein (Tsifrina et al, *Am. J. Pathol.* 155:1625 (1999)). HARE is highly related to these putative HA binding proteins (FIG. 28), which constitute a family of membrane-bound HA receptors, with the 175 kDa HARE as the prototype and first functionally identified member.

Figure 29:
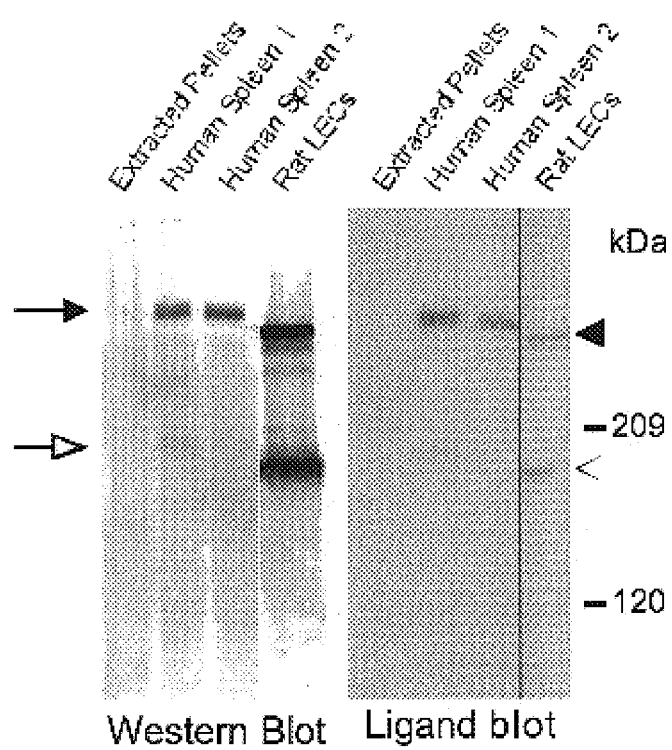
FIG. 29. Two HARE proteins in human spleen are recognized by anti-rat HARE monoclonal antibodies and specifically bind $^{125}$I-HA. Samples of human spleen and purified rat liver sinusoidal endothelial cells (LECs) were homogenized and treated with NONIDET™ P-40 in TBS, as described in Materials and Methods, using the human samples at two different protein concentrations (100 mg/ml for the Human Spleen 1 and 37.5 mg/ml for the Human Spleen 2 samples). After centrifugation, the supernatants and residual spleen extract pellets (pooled) were analyzed by non-reducing SDS-PAGE, transferred to nitrocellulose, and incubated with $^{125}$I-HA to assess their ability to bind HA (i.e. the ligand blot assay shown in the autoradiogram; right panel). After the ligand blot assay, the membrane was subjected to Western blot analysis (left panel) to detect the HARE protein using a mixture of mAbs to the rat 175 kDa HARE. The open and closed arrows indicate the positions of the two human HARE species, which are slightly larger (by about 10-15 kDa) at ~190 kDa and ~315 kDa than the corresponding rat HARE 175 kDa and 300 kDa species, indicated by the open and solid arrowheads, respectively.

Identification and purification of the human HARE. The ability of the mAbs raised against the rat 175 kDa HARE to recognize a human HARE homologue was tested, and it was found that three of the eight mAbs (i.e. numbers 30, 54, and 159) showed specific reactivity in Western blots or immunocytochemistry. In particular, the level of expression of putative HARE proteins in human spleen was great enough to detect specific $^{125}$I-HA binding activity and Western reactivity in crude extracts (FIG. 29). As observed with the rat HARE, two high molecular weight protein species, at ~190 kDa and ~315 kDa, were reactive with the mAbs and able to bind HA. A 50-fold excess of nonlabeled HA inhibited $^{125}$I-HA binding to either of the two human HAREs by >90% (not shown). The two human HARE species at ~190 kDa and ~315 kDa are larger by about ~15 kDa than the corresponding rat HARE species. Both assays showed a much greater amount of the larger than the smaller HARE in spleen.

Figure 30:
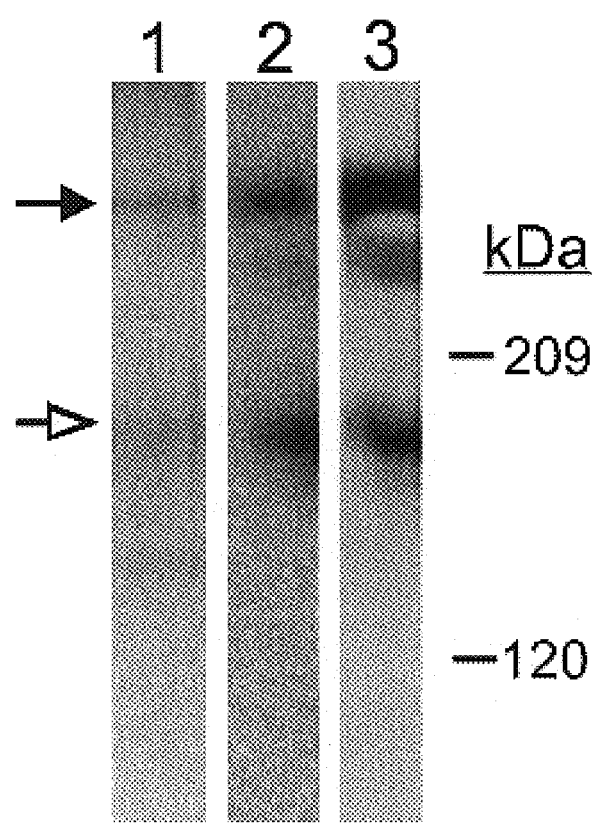
FIG. 30. Immuno-affinity purification of the human HARE proteins. Human HAREs were purified from NONIDET™ P-40 extracts of human spleen tissue by affinity chromatography using the anti-rat 175 kDa HARE mAb-30. The HARE proteins were eluted at low pH, concentrated using CENTRICON™ 30 devices, subjected to SDS-PAGE and transferred to nitrocellulose. The membrane was stained with 0.05% copper phthalocyanine tetrasulfonic acid, tetrasodium salt (lane 1) and then destained with distilled water. The destained nitrocellulose membrane was treated with TBST to block nonspecific binding sites and assessed for $^{125}$I-HA-binding activity (lane 2). After the ligand blot assay, the nitrocellulose membrane was subjected to Western blot analysis using a mixture of eight mAbs raised against the rat 175 kDa HARE protein (lane 3). The open and closed arrows indicate the positions of the human HARE proteins at ~190 kDa and ~315 kDa, respectively. These two human HARE species correspond to the previously characterized rat HARE 175 kDa and 300 kDa proteins.

The specific reactivity of the human HARE proteins with MAb-30, which had been used to purify the rat liver HARE, enabled the purification of the HARE directly from detergent extracts of human spleen by immunoaffinity chromatography (FIG. 30). Elution of proteins bound to MAb-30, using a low pH buffer, yielded the same two species identified in FIG. 29 as candidate HAREs. HA-binding activity and reactivity with anti-rat HARE mAbs comigrated with these two major proteins in the preparation. The anti-rat 175 kDa HARE mAbs that cross-react with the 190 kDa human HARE also recognize the ~315 kDa HARE. Based on densitometric analysis of protein detected in Western blots and ligand blots of the affinity purified proteins, the ~315 kDa HARE is consistently more abundant that the 190 kDa HARE in human spleen. The apparent molar ratio of the ~315 kDa HARE: 190 kDa HARE in spleen is ~2-3:1. Interestingly, essentially the reverse ratio is observed for the two HARE isoreceptors in rat liver, as described above.

Figure 31:
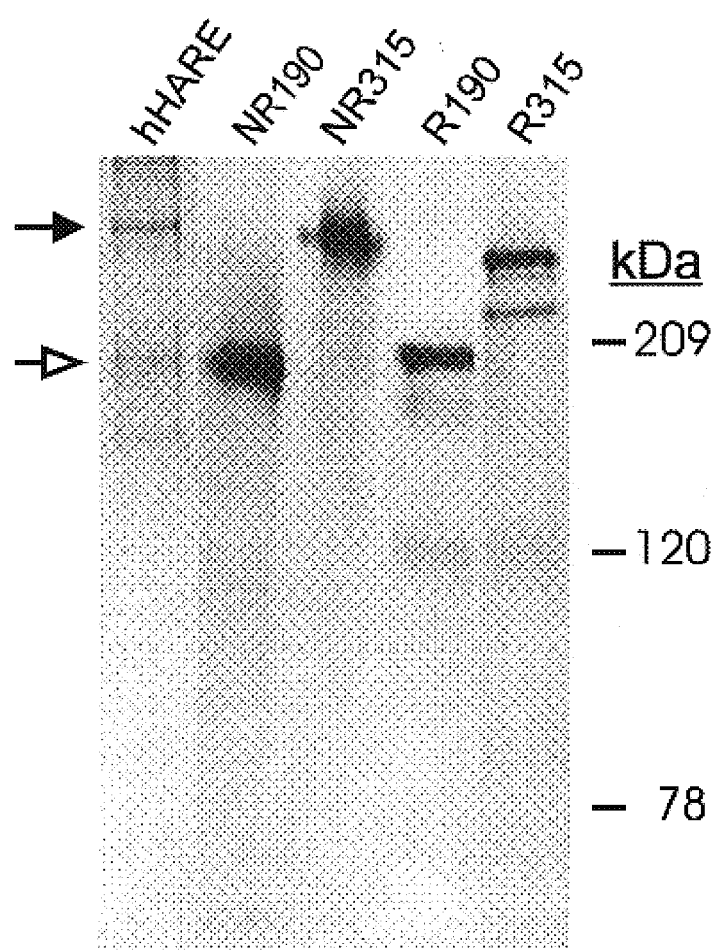
FIG. 31. Subunit analysis of the purified human 190 kDa and ~315 kDa HARE proteins. The two human HARE proteins were immunoaffinity-purified from human spleen using anti-rat 175HARE mAb-30, subjected to nonreducing SDS-PAGE and the gels were stained with Coomassie Blue (lane 1, hHARE). The 190 kDa HARE and ~315 kDa HARE protein bands were excised, minced and divided into two portions for analysis by SDS-PAGE, without reduction (lane 2, NR190 and lane 3, NR315) or with reduction (lane 4, R190 and lane 5, R315) using β-mercaptoethanol, followed by silver staining. The 190 kDa HARE protein gives a single ~196 kDa species after reduction, showing that the human 190 kDa HARE contains only one subunit. The 315 kDa HARE gives two major species after reduction, one at ~250 kDa and another at ~220 kDa, showing that this HARE contains at least two types of subunits. The apparent molar ratio of the 250 kDa and 220 kDa subunits in the ~315 kDa HARE is about 2-3:1.

Subunit characterization of the two human HARE isoreceptors. The affinity purified 190 kDa HARE and ~315 kDa HARE proteins were subjected to two-dimensional SDS-PAGE analysis to determine their subunit compositions. After electrophoresis under nonreducing conditions, as in FIG. 30, the two protein bands were excised, minced and then electrophoresed again with or without reduction (FIG. 31). After reduction, the 190 kDa HARE yielded a single protein that migrated at ~196 kDa, indicating that the smaller HARE contains only one polypeptide. As with the rat 175 kDa HARE, when the protein is reduced it unfolds and migrates more slowly in SDS-PAGE. This behavior is typical for receptors with extracellular domains containing disulfide bonds and the HARE proteins are Cys-rich. The ~315 kDa HARE yielded two major proteins of ~220 kDa and ~250 kDa after reduction, indicating that the larger HARE contains at least two types of disulfide-bonded subunits. These two subunits have been consistently observed in multiple independent preparations of purified human spleen HARE. The apparent molar ratio of the 250 kDa: 220 kDa subunits is about 2-3:1. In contrast, the rat 300 kDa HARE contains three subunits of 97, 230 and 260 kDa in apparent molar ratios of 1:1:1, respectively.

Figure 32:
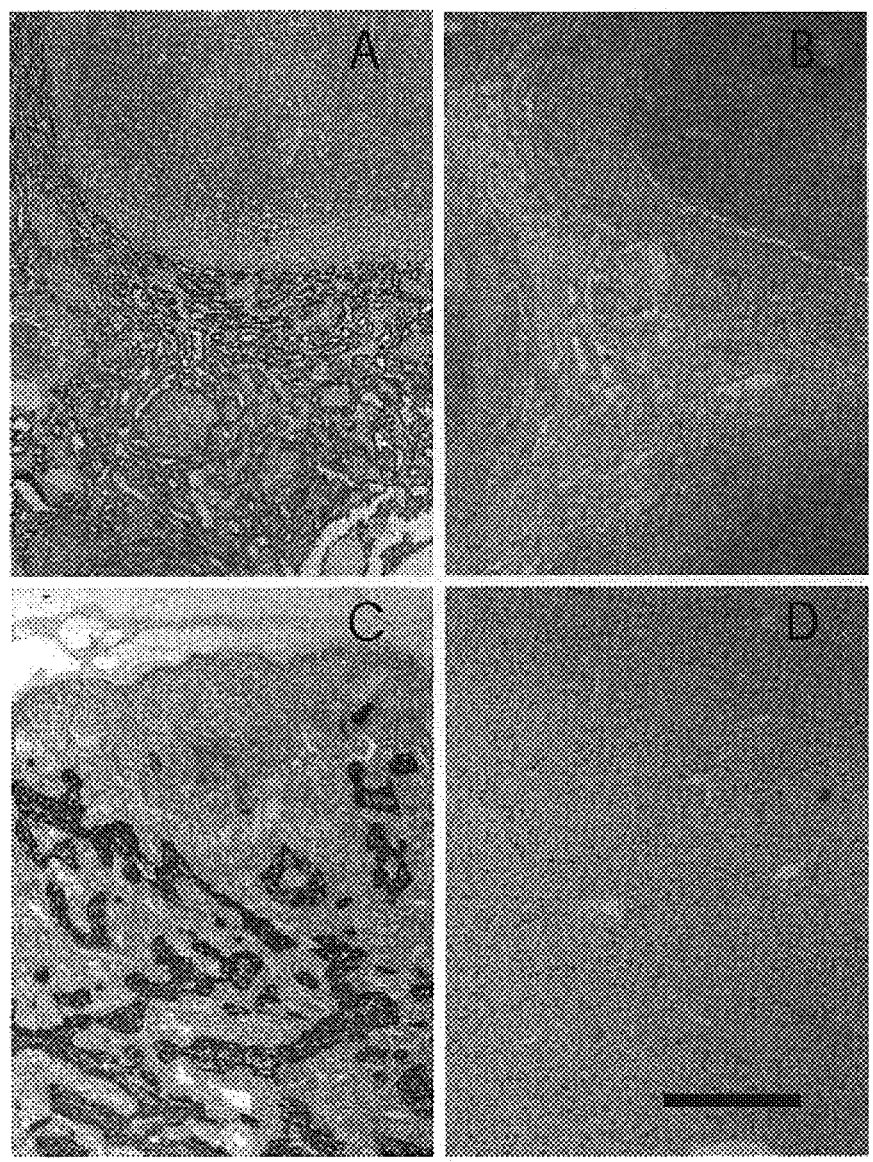
FIG. 32. Immunocytochemical localization of HARE in human liver, spleen and lymph node. Sections of human spleen (A and B), lymph node (C) and liver (D) were treated with either anti-HARE mAb-30 (A, C and D) or mouse serum (B) and then stained as described in Materials and Methods. A relatively low magnification is shown (the bar represents ~500 μm) to emphasize the localization of the human HARE protein in the sinusoidal regions of each tissue.

Localization of HARE in human tissues. Using mAB-30, which works well in immunocytochemical applications, abundant HARE protein expression was found in human liver, spleen and lymph node (FIG. 32) and bone marrow (not shown). Staining intensity and, therefore, protein expression levels were much greater in lymph node than spleen than liver. In each tissue only cells in the sinusoidal regions were stained. In spleen the germinal centers and white pulp areas of spleenic nodules were unstained, whereas the venous sinusoids of the red pulp stained strongly (FIG. 32A). Controls using mouse serum showed very low background staining in spleen (FIG. 32B) or the other tissues (not shown). A more thorough examination of other human tissues is still in progress.

Analysis of internal peptide sequences and determination of the human 190 kDa HARE sequence. The affinity purified HARE proteins were reduced, separated by SDS-PAGE and the band corresponding to the reduced 190 kDa HARE was excised and subjected to internal peptide analysis following trypsin digestion. When the protein databases were searched using the amino acid sequences derived from the purified protein, an identical match was found for a subset of seven peptides (Table IV) predicted to be within a hypothetical human protein of unknown function under accession number BAB15793. An additional seven tryptic peptides derived from the 190 kDa HARE were matched by mass spectroscopic analysis (within<0.2 Da) to the same deduced sequence in the database (Table V). This sequence had also been independently identified (see FIG. 28) as the most likely human homologue of HARE based on an overall homology of ~85% (78% identity) between the 1431 amino acid rat 175 kDa HARE and a putative 1193 amino acid protein encoded by BAB15793.

The identical match of 14 tryptic peptides, including a 23 residue peptide (Table IV), that contain a total of 120 amino acids (~10% of the protein) should be enough to conclude that the partial sequence encoded by BAB15793 is part of, and identical to, the human HARE. To support this conclusion further, however, RT-PCR with human spleen mRNA and a combination of human HARE-specific and BAB15793-specific primers was utilized to identify, clone and sequence PCR products that span portions of a ~4 kb region of the HARE-coding sequence

TABLE III

Oligonucleotide Primers Used for RT-PCR Analysis and DNA Sequencing

| Primer | SEQ ID NO: | Sequence | Position | PCR Product (bp) | Peptide Sequences confirmed |
|---|---|---|---|---|---|
| BAB1F | 5 | TCAATATAATCTGGCGAATGCAAT | 3-26 | | |
| HSP2R | 7 | AGTTCCGAATGGGCAGGTCAGCTC | 397-420 | 418 | 3 |
| BAB3F | 26 | ATGAGGAAGCTCGGGTTAAAG | 1452-1472 | | |
| BAB4R | 29 | GATGTAGCCATTGTTTGTTGCCAA | 1769-1792 | 341 | 2 |
| HSP2F | 33 | GAGCTGACCTGCCCATTCGGAACT | 397-420 | | |
| HSP3R | 35 | CTTTAACCCGAGCTTCCTCAT | 1452-1472 | 1076 | 4 |
| BAB6F | 30 | AGACGCCAAATGTGTCGACCTCCA | 3078-3101 | | |
| BAB7R | 31 | GAATAGGCCAGCACTTCCGTCAGG | 3510-3533 | 456 | 2 |
| BAB1F | 5 | TCAATATAATCTGGCGAATGCAAT | 3-26 | | |
| BAB10R | 32 | GGTGAGGCAGTTGGCGCTGGTATG | 851-874 | 872 | 3 |
| HSP2F | 33 | GAGCTGACCTGCCCATTCGGAACT | 397-420 | | |
| BAB10R | 32 | GGTGAGGCAGTTGGCGCTGGTATG | 851-874 | 478 | 3 |
| BAB10F | 34 | CATACCAGCGCCAACTGCCTCACC | 851-874 | | |
| HSP3R | 35 | CTTTAACCCGAGCTTCCTCAT | 1452-1472 | 622 | 3 |

TABLE III-continued

Oligonucleotide Primers Used for RT-PCR Analysis and DNA Sequencing

```
BAB9F   36  CAAGTACGGCATCCACTGTGACCA  697-720
HSP3R   35  CTTTAACCCGAGCTTCCTCAT     1452-1472   776        3
```

Other Primers used for RT-PCR and sequencing.

| Name | SEQ ID NO: | Sequence | Position |
|---|---|---|---|
| 5F | 37 | GGCTACTTCGGGCGAGACTGTCAG | 2386-2409 |
| 5R | 38 | CTGACAGTCTCGCCCGAAGTAGCC | 2386-2409 |
| 8F | 39 | TTGTACTCTTCAGCTGGCACC | 4406-4426 |
| 8R | 6 | GGTGCCAGCTGAAGAGTACAA | 4406-4426 |

TABLE IV

Summary of Amino Acid Sequences Derived From Peptides of the Purified Human 190 kDa HARE Protein

| Peptide Designation | Amino Acid Sequences | Start-End Residue | SEQ ID NO: |
|---|---|---|---|
| PR 1822 | XSKPK | 758-761 | 40 |
| PR 1823 | LTFDK | 1054-1058 | 41 |
| PR 1825-1$^{st}$ | GSIYQELPK | 440-448 | 42 |
| PR 1825-2$^{nd}$ | GTLFVPQNSGLGE | 1198-1210 | 43 |
| PR 1826 | DLVGPGPFTVFAPLSAAFDEEAR | 466-488 | 44 |
| PR 1869-1$^{st}$ | ELTSPFGTK | 133-141 | 45 |
| PR 1869-2$^{nd}$ | MPQVLR | 498-503 | 46 |
| PR 1870 | SPLGQYK | 1047-1053 | 47 |
| PR 1871-1$^{st}$ | VLEIQK | 107-112 | 48 |
| PR 1872 | VIHGLGK | 100-106 | 49 |

The human HARE proteins were immuno-affinity-purified from human spleen, subjected to SDS-PAGE and the 190 kDa protein band was excised and analyzed for internal peptide sequence following trypsin digestion. The amino acid sequences of these ten tryptic peptides were highly homologous or identical to the sequences of the rat 175 kDa HARE, reported herein above, and seven of these (not in bold face) were identical to regions within a human hypothetical protein of unknown expression and unknown function under GenBank accession number BAB15793. HARE peptides in boldface were not in the ORF for BAB15793.

TABLE V

Molecular Mass Mapping of Peptides Derived From the Human 190 kDa HARE Protein

| Measured Mass (Da) | Calculated Mass (Da) | Mass Difference (Da) | Start-End Residues | Sequence in Deduced Human | SEQ ID NO: |
|---|---|---|---|---|---|
| 599.273 | 599.294 | -0.021 | 796-800 | (K)GYFGR | 50 |
| 671.384 | 671.399 | -0.015 | 656-660 | (K)FHVIR | 51 |
| 792.621 | 792.426 | 0.195 | 1047-1053 | (R)SPLGQYK | 52 |
| 1034.621 | 1034.552 | 0.068 | 440-448 | (R)GSIYQELPK | 53 |
| 1061.781 | 1061.584 | 0.196 | 677-686 | (K)TLQGSELSVK | 54 |

TABLE V-continued

Molecular Mass Mapping of Peptides Derived From the Human 190 kDa HARE Protein

| Measured Mass (Da) | Calculated Mass (Da) | Mass Difference (Da) | Start-End Residues | Sequence in Deduced Human | SEQ ID NO: |
|---|---|---|---|---|---|
| 1624.051 | 1623.886 | 0.165 | 1047-1060 | (R)SPLGQYKLTFDKAR | 55 |
| 1092.771 | 1092.588 | 0.183 | 495-503 | (K)YGLMPQVLR | 56 |

The molecular masses of seven peptides derived from tryptic digestion of the purified human 190 kDa HARE protein were determined by MALDI-TOF mass spectrometry at the Louisiana State University Protein Chemistry Facility corresponded with perfect identity to deduced sequences within a predicted human protein of unknown function (accession number BAB15793). The monoisotopic peptide masses were searched against entries in the database, using PeptideSearch software from the EMBL Protein and Peptide Group. Identical masses are assigned in this search if the difference between the observed and predicted (calculated) masses for a peptide is <0.2 Da. The corresponding starting and ending residues for each peptide within the deduced protein sequence is shown. The N-terminal R or K residues in parentheses indicate the deduced residue in the protein and confirm that trypsin digestion occurred on the C-terminal side of those amino acids as expected.

TABLE VI

Characteristics of mAbs against the rat and human HARE isoreceptors
The 8 mAbs raised against the rat liver 175 kDa HARE were tested for their usefulness (+, yes; −, no) as reagents: for immunoprecipitation or Western blot (WB) analysis of either the rat or human small (175-190 kDa) or large (300-315 kDa) HARE proteins; for inhibition of HA binding to LECs or to either HARE in a ligand blot assay; and for immunocytochemical analysis of HARE expression in rat or human tissues.

| Property | Mouse Monoclonal Antibody Number | | | | | | | |
|---|---|---|---|---|---|---|---|---|
| | 28 | 30 | 54 | 154 | 159 | 174 | 235 | 467 |
| Immunoprecipitation of the rat 175 kDa HARE | + | + | − | − | + | + | + | + |
| Immunoprecipitation of the rat 300 kDa HARE | + | + | − | − | + | + | + | + |
| Recognizes nonreduced rat 175 kDa HARE in WB | + | + | − | + | + | + | + | + |
| Recognizes nonreduced rat 300 kDa HARE in WB | + | + | − | + | + | + | + | + |
| Recognizes reduced rat 175 kDa HARE in WB | − | − | + | − | + | ~+ | − | − |
| Recognizes 260 kDa subunit of rat 300 kDa HARE in WB | − | − | + | − | + | ~+ | − | − |
| Recognizes 230 kDa subunit of rat 300 kDa HARE in WB | − | − | + | − | + | ~+ | − | − |
| Recognizes 97 kDa subunit of rat 300 kDa HARE in WB | − | − | − | − | − | − | − | − |
| Blocks HA uptake in rat LECs at 37-degrees | − | − | − | − | − | + | + | − |
| Blocks HA binding to 175 kDa HARE in blots | − | − | − | − | − | + | − | − |
| Blocks HA binding to 300 kDa HARE in blots | − | − | − | − | − | + | − | − |
| Immunocytochemistry of rat tissues | + | + | + | + | + | + | + | + |
| Immunoprecipitation of the human 190 kDa HARE | − | + | − | − | − | − | − | − |
| Immunoprecipitation of the human 315 kDa HARE | − | + | − | − | − | − | − | − |
| Recognizes nonreduced human 190 kDa HARE in WB | − | + | − | + | − | − | − | − |
| Recognizes nonreduced human 315 kDa HARE in WB | − | + | − | + | − | − | − | − |
| Recognizes reduced human 190 kDa HARE in WB | − | − | − | − | + | − | − | − |
| Recognizes 250 kDa subunit of human 315 kDa HARE in WB | − | − | − | − | + | − | − | − |

TABLE VI-continued

Characteristics of mAbs against the rat and human HARE isoreceptors
The 8 mAbs raised against the rat liver 175 kDa HARE were tested for their
usefulness (+, yes; −, no) as reagents: for immunoprecipitation or Western
blot (WB) analysis of either the rat or human small (175-190 kDa) or large
(300-315 kDa) HARE proteins; for inhibition of HA binding to LECs or to
either HARE in a ligand blot assay; and for immunocytochemical analysis of
HARE expression in rat or human tissues.

| Property | Mouse Monoclonal Antibody Number | | | | | | | |
|---|---|---|---|---|---|---|---|---|
| | 28 | 30 | 54 | 154 | 159 | 174 | 235 | 467 |
| Recognizes 220 kDa subunit of human 315 kDa HARE in WB | − | − | − | − | + | − | − | − |
| Immunocytochemistry of human tissues | − | + | − | + | + | − | − | − |

TABLE VII

Human Gene Organization

| Exon Number | hHARE cDNA 1-4575 | Chromosome 12 Match (Exon) | Percent Identical | Nucleotides (number) | INTRON (nt) |
|---|---|---|---|---|---|
| 1 | 4-112 | 414,188-414,080 | 100 | 109 | 3,251 |
| 2 | 112-243 | 410,829-410,698 | 99 | 132 | 70,255 |
| 3 | 241-373 | 340,443-340,311 | 96 | 133 | 2,232 |
| 3 | 241-373 | 338,079-337,947 | 100 | 133 | 2,473 |
| 3 | 241-373 | 335,474-335,342 | 100 | 133 | 1,281 |
| 4 | 373-430 | 334061-334004 | 100 | 58 | 1,017 |
| 5 | 430-525 | 332,987-332,892 | 100 | 96 | 1,065 |
| 6 | 526-720 | 331,827-331,632 | 98 | 194/196 | 1,452 |
| 7 | 719-816 | 330,180-330,083 | 100 | 98 | 2,934 |
| 8 | 816-862 | 327149-327103 | 100 | 47 | 851 |
| 9 | 863-939 | 326,252-326,176 | 100 | 77 | 1,198 |
| 10 | 938-1065 | 324,978-324,851 | 100 | 128 | 2,046 |
| 11 | 1065-1140 | 322,805-322,730 | 100 | 76 | 1,878 |
| 12 | 1137-1211 | 320,852-320,778 | 100 | 75 | 7,322 |
| 13 | 1212-1332 | 313,456-313,336 | 100 | 121 | 1,018 |
| 14 | 1329-1380 | 312,318-312,267 | 100 | 52 | 1,100 |
| 15 | 1377-1465 | 311,167-311,079 | 98 | 88/89 | 1,500 |
| 16 | 1463-1610 | 309,579-309,432 | 100 | 148 | 1,117 |
| 17 | 1607-1751 | 308,315-308,171 | 100 | 145 | 1,319 |
| 18 | 1751-1812 | 306,852-306,791 | 100 | 62 | 1,367 |
| 19 | 1809-1990 | 305,424-305,243 | 100 | 182 | 2,425 |
| 17 | 1607-1751 | 302,818-302,674 | 100 | 145 | 5,618 |
| 20 | 1987-2079 | 297,056-296,964 | 100 | 93 | 2,053 |
| 21 | 2079-2226 | 294,911-294,764 | 100 | 148 | 17,238 |
| 18 | 1751-1812 | 277,526-277,465 | 100 | 62 | 1,367 |
| 19 | 1809-1990 | 276,098-275,917 | 100 | 182 | 2,304 |
| 20 | 1987-2079 | 273,613-273,521 | 100 | 93 | 2,052 |
| 21 | 2079-2226 | 271,469-271,324 | 98 | 146/148 | 1,630 |
| 22 | 2225-2283 | 269,694-269,636 | 100 | 59 | 1,158 |
| 23 | 2281-2409 | 268,478-268,350 | 100 | 129 | 1,648 |
| 24 | 2409-2559 | 266,702-266,552 | 99 | 150/151 | 2,619 |
| 25 | 2560-2664 | 263,933-263,829 | 100 | 105 | 1,316 |
| 26 | 2661-2772 | 262,513-262,402 | 100 | 112 | 2,256 |
| 27 | 2770-2967 | 260,146-259,949 | 100 | 198 | 1,421 |
| 28 | 2966-3108 | 258,528-258,386 | 100 | 143 | 2,499 |
| 29 | 3108-3243 | 255,887-255,752 | 100 | 136 | 1,946 |
| 30 | 3241-3408 | 253,806-253,639 | 100 | 168 | 143 |
| 31 | 3407-3516 | 253,496-253,387 | 100 | 110 | 2,450 |
| 32 | 3515-3635 | 250,937-250,817 | 100 | 121 | 842 |
| 33 | 3634-3776 | 249,975-249,833 | 100 | 143 | 2,026 |
| 34 | 3776-3887 | 247,807-247,696 | 100 | 112 | 863 |
| 35 | 3887-4134 | 246,833-246,505 | 100 | 130 | 881 |
| 36 | 4015-4075 | 245,624-245,564 | 100 | 120 | 2,735 |
| 37 | 4076-4132 | | | | |
| 38 | 4133-4575 | 242,829-242,387 | 100 | 443 | | hHARE ORF encoding 1394 amino acids is nucleotides 1-4182

Table III). Eight of the PCR products (Table III) each encoded two-three tryptic peptides predicted to be in the BAB15793 protein and confirm the relationship between the purified human spleen HARE and the partial protein sequence deduced from BAB15793.

Figure 33:
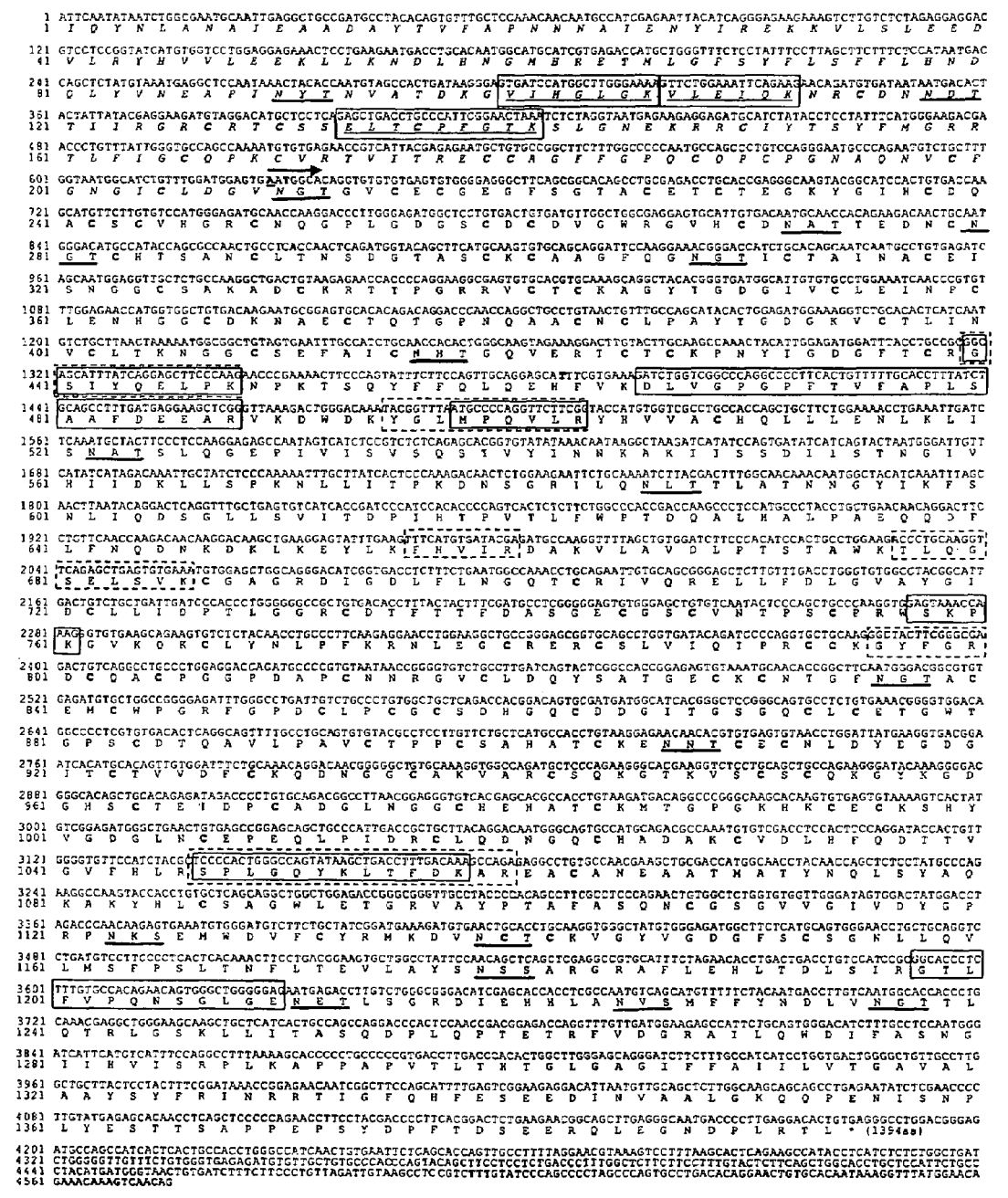

The nucleic acid sequence (SEQ ID NO:24) and deduced protein sequence (SEQ ID NO:25) for the 190 kDa HARE is shown in FIG. 33. The BAB15793 nucleotide sequence contains a partial ORF of 1193 amino acids that starts at nucleotide position 606. The RT-PCR products generated from spleen mRNA confirmed almost all of the 4575 bp BAB15793 sequence with several important exceptions. Most significantly, key results characterizing new human HARE sequences were obtained from the most 5' PCR product generated from primer pair BAB1F (SEQ ID NO:5) (derived from an upstream region of BAB15793 that had been incorrectly concluded to be untranslated) and HSP-2R (SEQ ID NO:26). The majority of this 418 bp PCR product is upstream of the putative Trp residue (see FIG. 28) that begins the BAB15793 hypothetical protein sequence (FIG. 33). In fact, the first seven residues of this hypothetical sequence were incorrect due to a frameshift error. The 139 amino acid sequence derived from the 1F-2R (SEQ ID NOS:5 and 7, respectively) PCR product is in-frame with, and extends the size of, the human HARE ORF to at least 4182 bp, ending at a stop codon and encoding a protein of 1394 residues. This additional deduced protein sequence contains another three tryptic peptides identified from the purified HARE protein (Table IV) and is 83% identical to the same 139 residue region in the rat 175 kDa HARE.

Figure 37:
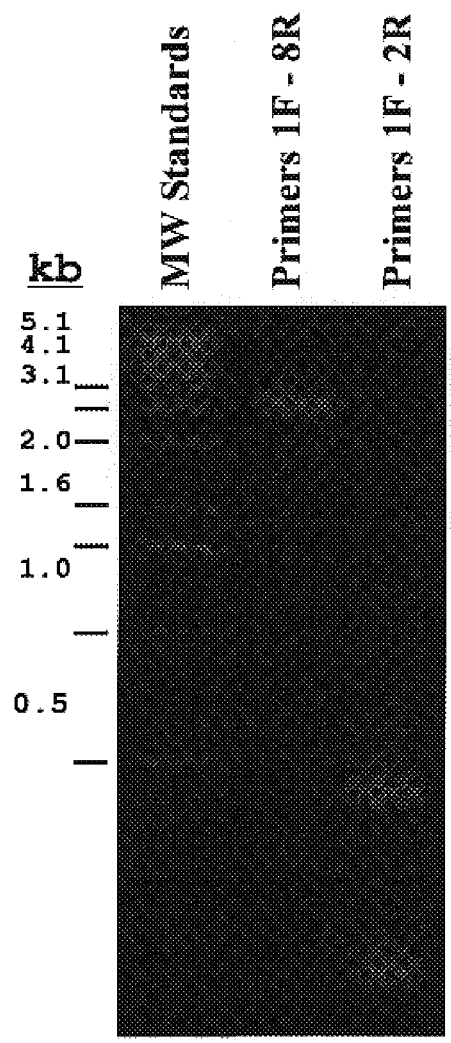
FIG. 37. Amplification of a 1394 amino acid Open Reading Frame for the human 190 kDa HARE. Using the primer pair 1F-8R (SEQ ID NO:5 and SEQ ID NO:6)(Table III), the entire 1394 amino acid reading frame (4182 nucleotides) shown in FIG. 33 was successfully amplified by PCR (lane 2). The primer pair 1F-2R (SEQ ID NO:5 and SEQ ID NO:7) (Table III) gave the expected smaller 418 bp product (lane 3). The template used was a human lymph node MARATHON™-Ready cDNA library (from Clontech). A similar 4182 bp PCR product was also seen with a comparable cDNA library prepared from spleen. The PCR reactions using ADVANTAGE™ 2 Polymerase Mix (from Clontech) were carried out as follows: 94° C. for 2 min—1 cycle; 94° C. for 30 sec, 70° C. for 10 min—5 cycles; 94° C. for 30 sec, 65° C.

As shown in FIG. 37, the entire 1394 amino acid open reading frame of the human 190 kDa HARE (SEQ ID NO: 25) has been successfully amplified from a human lymph node cDNA library. The primer pair BAB1F-8R (SEQ ID NO:5 and SEQ ID NO:6, respectively) (Table III) was utilized for the PCR amplification of the entire 1394 amino acid reading frame (SEQ ID NO:25) (4182 nucleotides) shown in FIG. 33. A similar 4182 bp PCR product was also seen with a comparable cDNA library prepared from human spleen (not shown).

Based on all of these above results, we conclude that we have identified and assembled the human cDNA sequence encoding the 190 kDa HARE, except for the amino terminal end. Assuming that the human core protein is larger than the 1431 amino acid rat protein by about 15 kDa, we estimate that a ~170 amino acid region remains to be identified. 5' RACE analyses are ongoing with multiple approaches to extend the 5' sequence of the human HARE ORF to the equivalent NH$_2$-terminus found for the recombinant rat 175 kDa HARE. Since we have recently identified a human cDNA library from which we can amplify the complete 4182 bp PCR product expected from the primer pair BAB1F-8R (SEQ ID NO:5 and SEQ ID NO:6, respectively), we can also clone the appropriate complete cDNAs. Therefore, the present invention is not limited to the cDNAs disclosed herein, but further encompasses the complete cDNA for human HARE which can be obtained using standard procedures known to a person of ordinary skill in the art.

Figure 34:
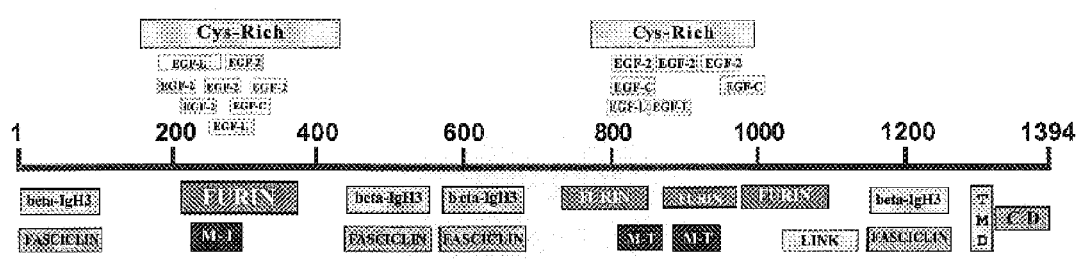
FIG. 34. Domain organization of the human 190 kDa HARE. The scheme depicts the organization of protein domains identified by the programs Pfam-HMM, CD-Search, ScanProsite or SMART (Schultz et al, *Proc. Natl. Acad. Sci. USA*, 95:5857 (1998)). Abbreviations used for some of the domains include CD (cytoplasmic domain), TMD (transmembrane domain), M-T (metallothionein), and EGF-C, EGF-L or EGF-2 for epidermal growth factor calcium, laminin or type 2 domains, respectively.
Figure 35:
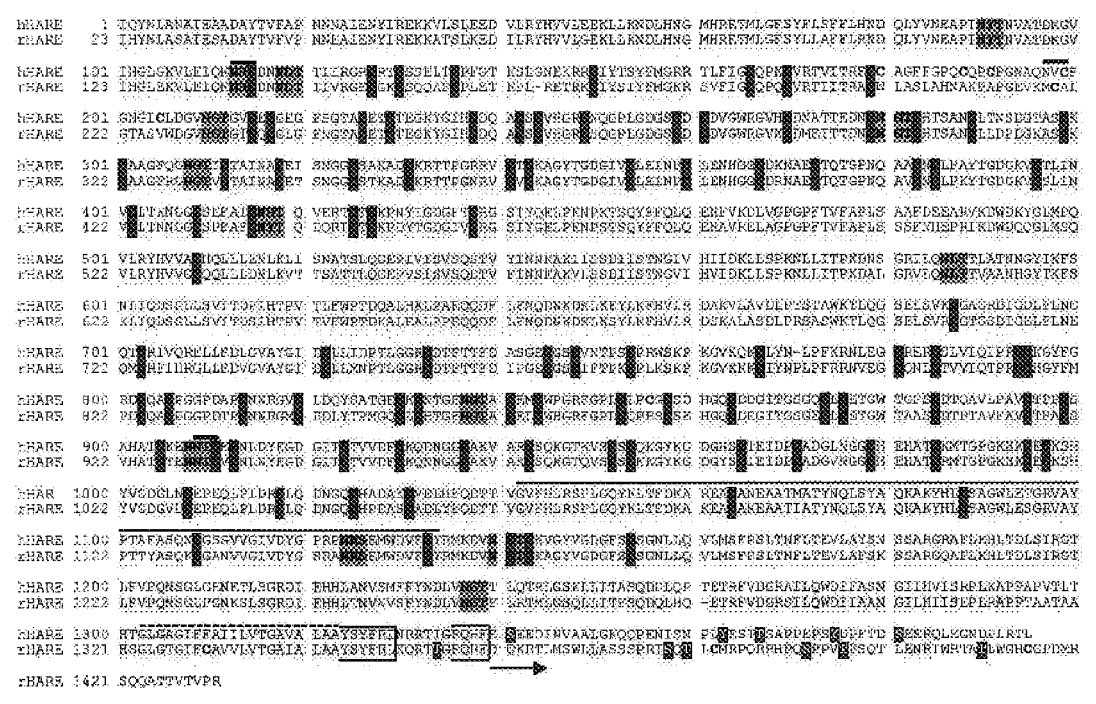

Domain organization and characteristics of the 190 kDa HARE. The overall organization of the human 190 kDa HARE protein is very similar to that of the rat 175 kDa HARE. The human HARE is predicted to be a type I membrane protein (FIG. 34), with a large NH$_2$-terminal extracellular domain (>1300 amino acids), a single transmembrane domain (~21 amino acids), and a small COOH-terminal cytoplasmic domain (~72 amino acids). The predicted mass of the 1394 residue partial core protein determined here is 151,402 Da and the pI is pH 5.9. The protein contains 17 potential N-glycosylation sites (—N—X-T/S-) in the extracellular domain. Twelve of these sites are identical with sites in the rat 175 kDa HARE (FIG. 35). An additional three nonclassical glycosylation sequons (—N—X-C-) are present in the human HARE, two of which are conserved with the rat HARE. An interesting feature of these Cys-containing sites is that glycosylation and participation of the Cys in a disulfide bond may be mutually exclusive (Miletich and Broze, *J. Biol. Chem.* 265:11397 (1990)). The 190 kDa HARE extracellular domain has two cysteine-rich regions and multiple EGF-like, βIgH3, Furin, Metallothionein and Fasciclin domains, as well as Early Protein and DSL domains and one 93 amino acid Link (or Xlink) domain near the membrane junction (Gly$^{1041}$-Tyr$^{1133}$). Many of the programs such as Pfam-HMM, ScanProsite, SMART (Schultze et al, *Proc. Natl. Acad. Sci. USA* 95:5857 (1998)) or CD-Search identify domains that are only partial or weak matches and overlap with other domains. In particular the EGF-like domains show this characteristic (FIG. 34). Although the overall organization of all these above domains is very similar between the human and rat HARE proteins, the exact arrangement and number of each type of domain is not identical.

The partial human 190 kDa HARE and the rat 175 kDa HARE protein sequences are 76.7% identical, with a gap frequency of only 0.2% (using the SIM Alignment Program), over a region containing 1394 residues (FIG. 35). An additional 6.5% of the amino acid differences between the two proteins are conservative substitutions (e.g. R/K or S/T). Almost all of the cysteine residues within the extracellular domains of the two HARE proteins are absolutely conserved, which suggests that the two proteins have the same overall folding and organization of their polypeptide chains. The other HARE family members noted in FIG. 28 also share this extensive conservation of cysteine residues in their extracellular domains, as well as the same overall domain organization including the Xlink domain and a single predicted transmembrane region. Unlike the rat protein, the human HARE has no cysteine residues in its transmembrane or cytoplasmic domains. The cytoplasmic domains of the two HARE proteins are less conserved (25% identical) than their transmembrane (76% identical) or extracellular domains (80%). Nonetheless, two candidate (φXXB motifs for targeting these receptors to coated pits are highly conserved: the human HARE YSYFRI$^{1328}$ and FQHF$^{1338}$ motifs differ by only one amino acid from the corresponding regions in the rat HARE cytoplasmic domain (FIG. 35).

Organization of the Human Gene for HARE. Table VII and FIG. 38 summarize the organization of exons and introns within a gene on human chromosome 12 that encodes 1357 amino acids of the 190 kDa HARE protein disclosed herein. More than 97% of the 4182 nucleotide sequence representing the ORF for this portion of HARE is present as ~38 exons interrupted by more than 40 introns, which vary in length from 143 to 70,255 nucleotides. All regions of the human HARE ORF disclosed here, with the exception of putative exon 37 (encoding nucleotides 4076-4132) are present in the continuous DNA sequence (>171 kb) deposited under accession number NT_024383.2. The sequence was deposited as a putative gene of unknown expression or function. The disclosure here provides the first identification of a function for the protein encoded by this gene. The complete gene is expected to be >200 kb in size. The coding exons (shown as black or gray boxes with boldface numbers) are small and relatively uniform in length; 12 contain <100 nucleotides, 24 contain 100-200 nucleotides and 1 is >200 nucleotides. The variably shaded box (#38) represents the 3' downstream region of the HARE gene containing polyA sites etc. The arrangement of exons within the 171 kb region reported by the human genome project indicates that several coding exons are duplicated (these are shaded in gray); numbers 3, 17, 18, 19, 20 and 21. The human HARE nucleotide sequence disclosed here is >99.8% identical (4065 out of 4071) to the nucleotide sequence of the exons identified in the NT_024383.2 gene.

Discussion

HA was discovered and named over 67 years ago by Meyer and Palmer (*J. Biol. Chem.* 107:629 (1934)), and then shown by many other investigators to be a common, ubiquitous, component of essentially all ECMs in vertebrates. HA is the only glycosaminoglycan that is not sulfated and not covalently attached to a core protein. It is a linear polymer composed of the repeating disaccharide unit 2-deoxy, 2-acetamido-D-glucopyranosyl-β(1,4)-D-glucuronopyranosyl-β (1,3) (Laurent and Fraser, *Degradation of Bioactive Substances: Physiology and Pathophysiology,* 249, CRC Press, Boca Raton, Fla. (1991); Laurent and Fraser, *FASEB J.* 6:2397 (1992)). The molecular weight of native HA can be as high as $10^7$, which is up to 10,000-times the size of other glycosaminoglycan chains attached to proteoglycans. The physical characteristics of HA solutions, particularly their rheologic properties and viscoelasticity, are ideally suited for the role of HA in specialized ECMs of skin, cartilage, and fluids such as in the vitreous humor of eye and the synovium of joints.

Although its structure is simple, HA influences many cell functions and behaviors, including cell migration, differentiation, and phagocytosis (Evered and Whelan, *The Biology of Hyaluronan,* 143:1 (1989); Laurent and Fraser, *FASEB J.* 6:2397 (1992); Knudson and Knudson, *FASEB J.* 7:1233 (1993); Toole, *J. Intern. Med.* 242:35 (1997); Abatangelo and Weigel, *New Frontiers in Medical Sciences: Redefining Hyaluronan,* Elsevier Science BV., Amsterdam (2000);Turley, *Cancer Metastasis Rev.* 11:21 (1992)). HA is an important molecule in development (Toole, *J. Intern. Med.* 242:35 (1997); Gakunga et al, *Devel.* 124:3987 (1997)), wound healing (Iocona et al, *J. Surg. Res.* 76:111 (1998); Burd et al, *Br. J. Plast. Surg.* 44:579 (1991); Weigel et al, *J. Theoret. Biol.* 119:219 (1986); Chen and Abatangelo, *Wound Repair Regen.* 7:79 (1999)), angiogenesis (West et al, *Science,* 14:1324 (1985); Deed et al, *Int J. Cancer,* 71:251 (1997); Rahmanian et al, *Exp. Cell Res.* 237:223 (1997)), and tumor growth and metastasis (Zhou et al, *J. Biol. Chem.* 276: in press (2000); Csoka et al *Invasion Metastasis,* 17:297 (1997); Delpech et al, *J. Intern. Med.* 242:41 (1997)). For example, the ability of HA to form large aggregates by binding to ECM proteoglycans, such as aggrecan and perlecan, is necessary for normal tissue differentiation (Vertel et al, *Biochem J.* 301:211 (1994); Handler et al, *Dev. Dyn.* 210:130 (1997)).

Previously, most investigators believed that the physiological function of HA in the ECM was only structural or physical. However, HA is now recognized as a pharmacologically active signaling molecule, in addition to an ECM structural component. Numerous cell types respond physiologically to HA of different sizes. In particular, small, but not large, HA stimulates angiogenesis (West et al, *Science,* 14:1324 (1985); Deed et al, *Int J. Cancer,* 71:251 (1997); Rahmanian et al, *Exp. Cell Res.* 237:223 (1997)) and small, not large, HA stimulates activated macrophages to induce the expression of a large number of genes (Horton et al, *J. Biol. Chem.* 273: 35088 (1998); Horton et al, *Am. J. Physiol. Lung Cell Mol. Physiol.* 279:707 (2000)). Similarly, only small HA induces the expression of NO synthase in Kupffer cells and LECs, but not in stellate cells or hepatocytes (Rockey et al. *Hepatol.* 27:86 (1998)). Although most investigators presume that specific cell surface receptors in these sensitive cell types bind these small HA fragments and then mediate the stimulation of intracellular signal cascades, no such receptor has yet been identified.

There are currently about four known types of HA-binding proteins or hyaladherins (Toole. *Curr. Opin. Cell Biol.* 2:839 (1990)): enzymes, components of the ECM, cell surface receptors and soluble plasma or intracellular molecules. Cell surface HA receptors that have been characterized to date include CD44, LYVE-1, CD168 (formerly designated RHAMM), ICAM-1, and HARE. A scavenger receptor able to bind and internalize HA may also be present in liver (McCourt et al. *Hepatol.* 30:1276 (1999)). HARE is distinct from all the other cell surface receptors with specificity for HA because it is an endocytic, recycling receptor that mediates the rapid and efficient endocytosis of HA via the clathrin-coated pit pathway. CD168 is found on the surface of, and inside, many cell types and can mediate a cell migration response to HA (Turley et al. *Blood,* 81:446 (1993); Hofmann et al, *J. Cell Sci.* 111:1673 (1998)). The CD44 family of transmembrane glycoproteins is found in hemopoietic cells, epithelial and endothelial cells, lymphocytes and many cancer cells (Lesley et al. *Adv. Immun.* 54:271 (1993)) and has structural homology to cartilage link protein (Bajorath et al. *J. Biol. Chem.* 273:338 (1998)).

LYVE-1, a member of the CD44 family, is localized to lymphatic vessel endothelial cells in many tissues, but is not present in blood vessels (Banerji et al. *J. Cell Biol.* 144:789 (1999)). Preliminary results indicate that LYVE-1 and HARE have distinct, non-overlapping distributions within various lymphatic tissues. HARE is expressed in the sinusoids of liver and lymphatic tissues (Zhou et al. *J. Biol. Chem.* 275:37733 (2000)), which is a localization well suited to keep a very low level of systemic HA (i.e. HA that is not associated with an ECM). Liver, spleen and lymph node express large amounts of HARE for this purpose. ICAM-1 is an adhesion molecule on the cell surface that binds HA (Hayflick et al, *Immunol. Res.* 17:313 (1998)). Some confusion may still exist regarding ICAM-1 because several studies have appeared (Gustafson et al, *Glycoconj. J.* 12:350 (1995); Fuxe et al, *Brain Res.* 736:329 (1996)) that were based on the incorrect identification of ICAM-1 as the endocytic HA receptor in LECs (McCourt et al, *J. Biol. Chem.* 269:30081 (1994)). This misidentification was later acknowledged to be an artifact (McCourt and Gustafson, *Int J. Biochem. Cell Biol.* 29:1179 (1997)), but the erroneous report was not withdrawn.

Because it is non-immunogenic and has special viscoelastic and Theological properties in solution, HA is used in many clinical applications, and its medical uses are growing rapidly. For example, ophthalmic surgeons worldwide routinely use sterile solutions of pure, pyrogen-free, high molecular weight HA in numerous procedures (Goa and Benfield, *Drugs,* 47:536 (1994); Panay and Lower, *Curr. Opin. Obstet. Gynecol.* 11:379 (1999)). HA is ideally suited for such uses, since it is a natural ocular component, and its physical properties keep the eyeball from collapsing. Many patients with osteoarthritis or rheumatoid arthritis now experience significant improvement after receiving intra-articular injections of HA (Pelletier and Martel-Pelletier. *J. Rheumatol.* 20:19 (1993)). Laurent et al. (*Arch. Otolaryngol. Head Neck Surg.* 114:1435 (1988)) have also used HA to heal perforated tympanic membranes, which then restores hearing. HA has been used topically to reduce postoperative pericardial adhesions and as an aerosol to prevent elastase-mediated injury in pulmonary emphysema (Cantor et al. *Proc. Soc. Exp. Biol. Med.* 217:471 (1998)). HA is also used as a drug delivery vehicle (Ilium et al. *J. Control Release,* 29:133 (1994); Luo et al. *J. Control Release,* 69:169 (2000)). Because of its use in such a wide array of medical applications, it is critical that we understand the biological effects of exogenously administered HA and how its turnover and clearance from the body is regulated.

Clearance of the endogenous circulating HA from lymph and blood is also likely to be very important for normal health, because the viscosity of these fluids would rapidly increase to dangerous levels if the concentration of HA was allowed to accumulate, particularly if it was of high molecular weight as found in lymph fluid (more than about $10^6$). For example, one can readily envision the difficulty of erythrocyte flow through tiny capillaries under conditions of high viscosity. The 175/190 kDa and 300/315 kDa HARE proteins are two HA isoreceptors for endocytosis present in mammalian liver, spleen and lymph node. Such two HA isoreceptors may be necessary to mediate HA uptake and degradation in mammals because of the extremely broad range of HA molecular masses present in tissues throughout the body. The two isoreceptors could have different preferences for the size of the HA with which they interact. Presumably the smaller HARE would interact with smaller HA and the larger HARE with larger HA.

The present results show that the rat 175 kDa HARE is a bone fide endocytic receptor for HA, capable of functioning independently of the 300 kDa HARE. Although it is possible that the 175 kDa HARE and 300 kDa HARE species could function together as a large complex, it is apparently not necessary for these two HAREs to be present in the same cell in order to create a specific functional HA receptor. Therefore, the 175 kDa HARE and 300 kDa HARE are independent isoreceptors. Studies are in progress to determine whether sinusoidal endothelial cells express either one of the HARE species alone or always together, and if the expression pattern of the two HARE species is tissue specific.

The rat 175 kDa HARE protein identified herein is a functional endocytic HA receptor when expressed from a non-naturally occurring synthetic cDNA. The protein is not directly encoded by an mRNA, but rather is apparently derived from the proteolytic processing of a larger protein, which may be the large 260 kDa subunit of the 300 kDa HARE complex. The mRNA encoding the rat 175 kDa HARE is ~10 kb, substantially longer than that required for this size protein. That the characteristics of the rat and human HAREs are similar indicates a similar proteolytic processing may generate the human 190 kDa HARE from one of the large subunits of the 315 kDa HARE. The two human HARE isoreceptors described here have a very similar organization to the two rat HAREs, and the three anti-rat mAbs that recognize the 190 kDa human HARE also cross-react with the two large subunits of the human ~315 kDa HARE (not shown).

Figure 36:
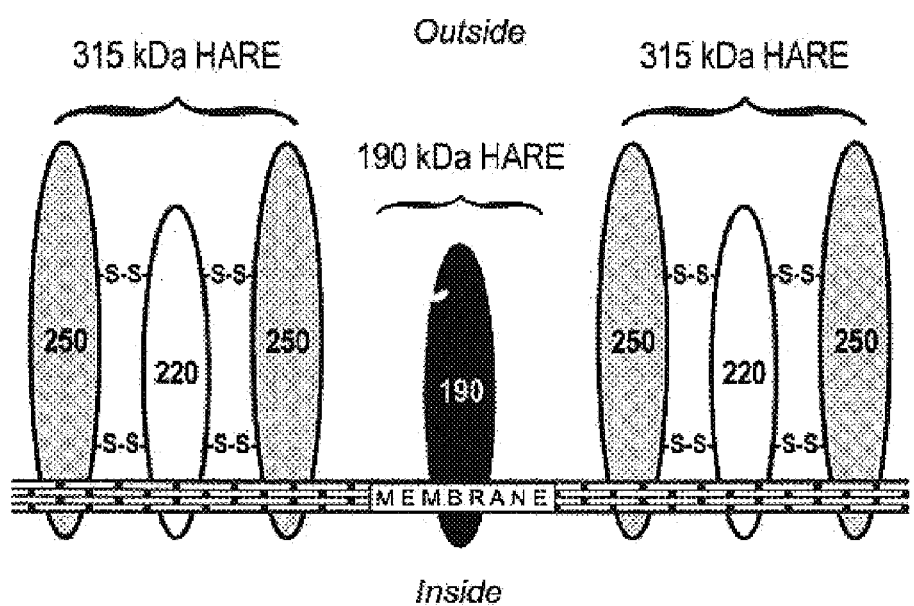
FIG. 36. Model for the organization of the two human spleen HARE isoreceptors. The 190 kDa and ~315 kDa HARE isoreceptors isolated from spleen are depicted as separate species in approximate molar ratios of 1:2, respectively. The 190 kDa HARE contains only one protein. The large HARE complex is composed of two (or perhaps three) disulfide-bonded subunits of about 250 kDa and one subunit of 220 kDa, respectively. Preliminary results indicate that the molar ratios of the affinity purified 190 kDa and ~315 kDa HARE isoreceptors from different tissues may be different. All HARE proteins and subunits are membrane-bound and are predicted to contain small cytoplasmic domains and very large ectodomains. The HARE are elongated, rather than globular, proteins (Yannariello-Brown et al, *Glycobiol.* 7:15 (1997)).

The organization of the two HARE isoreceptors purified from human spleen is depicted in FIG. 36. The 190 kDa and ~315 kDa HAREs are most likely isoreceptors able to function independently as coated pit mediated endocytic receptors for HA. The 190 kDa HARE contains a single protein. The ~315 kDa HARE disulfide-bonded complex contains 2-3 copies of a 250 kDa subunit and 1 copy of a 220 kDa subunit. Spleen has approximately 2-3 times more of the ~315 kDa HARE species compared to the 190 kDa HARE. It is proposed that the large HARE may be more effective in binding and in internalizing larger HA and the smaller HARE may be more effective in recognizing smaller HA. Since the size distribution of HA varies ~100-fold in the body, more than one HARE may be needed physiologically to remove it.

The large extracellular domain of the 190 kDa HARE is predicted (Schultz et al, *Proc. Natl. Acad. Sci. USA* 95:5857 (1998)) to contain a delta serrate ligand (DSL) domain, and up to four β-Ig-H$_3$/fasciclin-like domains, three Metallothionein domains, four Furin-like domains, a Link domain and ~24 EGF-like domains (many of which overlap) arranged in two cysteine-rich clusters separated by a 353 amino acid region that is cysteine-poor. Fasciclins are Ig-like cell adhesion molecules originally found on a subset in insects of axons during neuronal development (Kose et al, *Development,* 124:4143 (1997)). The EGF-like domains include laminin-like, EGF-1, EGF-2 and $Ca^{+2}$-binding domains (Selander-Sunnerhagen et al, *J. Biol. Chem.* 267:19642 (1992)). We showed previously in rat LECs that HARE can function without any divalent cations including $Ca^{+2}$ (Yannariello-Brown et al, *J. Cell Biochem.* 48:73 (1992)). Several of the EGF-like domains in the human HARE have thee characteristic pattern of six cysteines needed for the typical organization and folding of this domain (Selander-Sunnerhagen et al, *J. Biol. Chem.* 267:19642 (1992)).

The cytoplasmic domain of the human HARE ($\sim Y^{1323}$-$L^{1394}$) contains four tyrosine, seven serine and five threonine residues, although only residues $S^{1340}$, $S^{1380}$, $T^{1366}$, $Y^{1362}$ and $Y^{1374}$ are predicted (by NetPhos 2.0) to be phosphorylated. PEST motifs for rapid degradation, or consensus sequences for O-glycosylation by GlcNAc are not present. As expected, the cytoplasmic domain contains several putative, candidate motifs for targeting the protein to clathrin coated pits. The sequence YSYFRI$^{1328}$ at the junction between the transmembrane and cytoplasmic domains, contains an interesting overlapping combination of two φXXB motifs, where φ is either tyrosine or phenylalanine, X can be any amino acid and B is a hydrophobic residue with a bulky side chain. The LDL, mannose and cation-dependent mannose 6-phosphate receptors, which are recycling endocytic receptors, are targeted to coated pits by very similar overlapping φXXB motifs (Mellman, *Annu. Rev. Cell Biol.* 12:575 (1996)). A third candidate φXXB motif is present at FQHF$^{1338}$.

The Link domain is clearly a good candidate for an HA-binding region but it is very likely that other, perhaps multiple, non-Link HA-binding domains are also present in the extracellular domain of HARE. Day, Jackson and colleagues have extensively investigated the structural requirements for HA-binding activity of Link domains from different proteins (Bajorath et al, *J. Biol. Chem.* 273:338 (1998); Kahmann et al, *Structure Fold Des.* 8:763 (2000); Banerji et al, *Protein Expr. Purif.* 14:371 (1998); Mahoney et al, *J. Biol Chem.* Published Apr. 3, 2001, JBC, online). In general, the affinities of these link domains is in the $10^6 M^{-1}$ range, which is not suitable for efficient receptor mediated endocytosis. Receptor-ligand complexes targeted to coated pits typically have $K_d$ values in the nM range. ECM proteins containing Link domains can form stable multivalent networks with HA, although the binding affinity of individual HA-Link domain interactions is weak. Based on these above considerations, the extracellular domain of HARE contains multiple HA-binding regions. The formation of multivalent interactions of an HA molecule with several HA-binding domains on separate HAREs would not occur as efficiently as multiple interactions within the same HARE molecule. The longer ~315 kDa HARE isoreceptor probably has more HA-binding domains than the smaller 190 kDa HARE.

Figure 28:
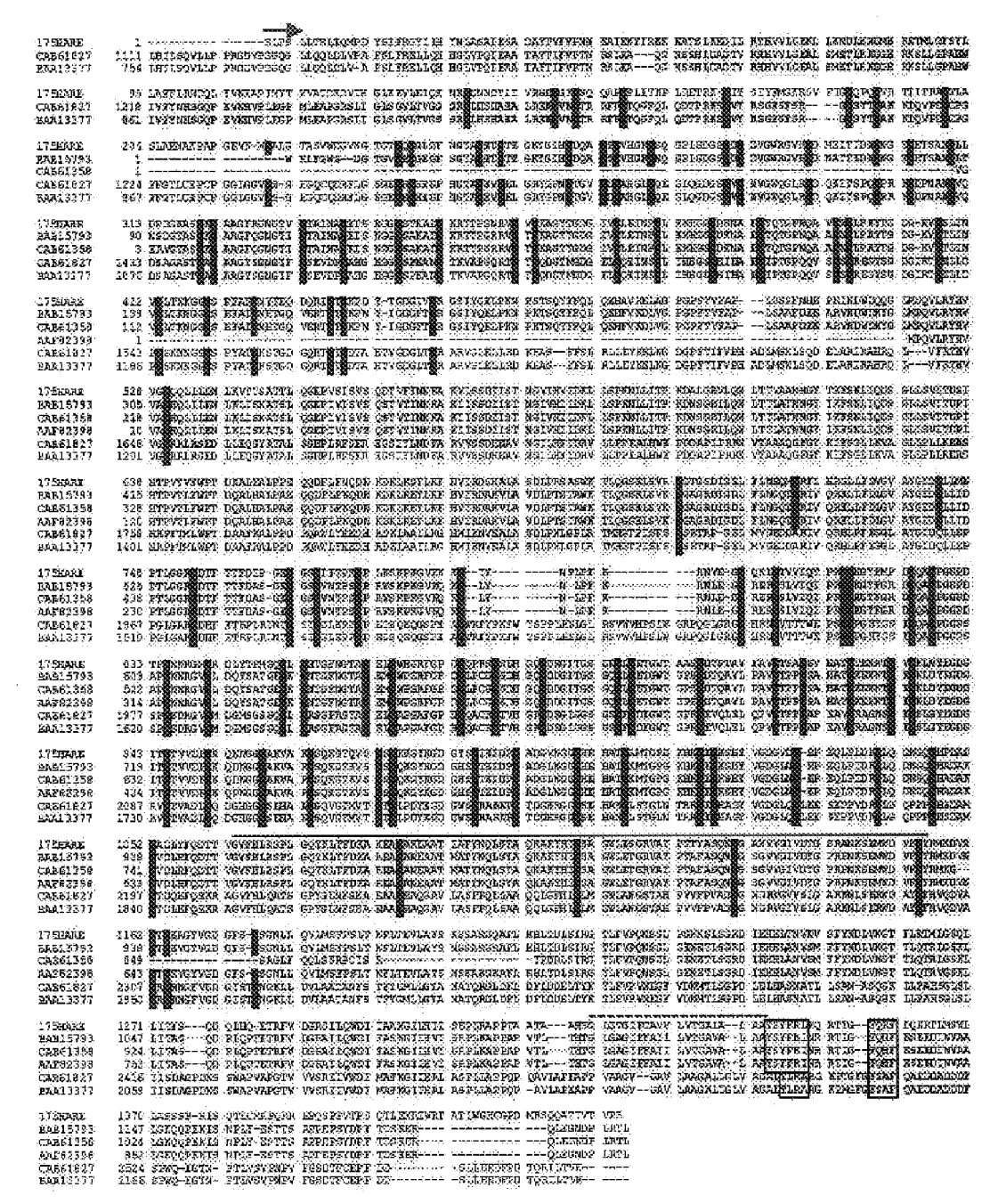

The human HARE sequence reported here shares a high level of identity with a family of human proteins, as well as the rat 175 kDa HARE, shown in FIG. 28. One of these deduced human proteins, derived from accession number AAF82398, was designated FELL because it contains Fasciclin, EGF-Like, and Link domains. The three sequences represented by AAF82398, CAB61358 and BAB15793, have 95% identity among themselves and may be the same species; the slight differences could be due to sequencing errors or alternative splicing. The sequences of BAA13377 and CAB61827, which encodes stabilin-1, are more related to each other than to the three sequences noted above or to HARE. Although the BAA13377 mRNA sequence is present in endothelial cells, the presence of protein or associated HA-binding activity was not determined (Tsifrina et al, *Am. J. Pathol.* 155:1625 (1999)). Because we have identified the first function for a member of this protein family, it may be more relevant now to designate these proteins as HARE or HARE-like rather than FELLS.

The overall similarities in their extracellular, transmembrane and cytoplasmic domains suggest that the members of this HARE protein family may all be able to bind HA, chondroitin, chondroitin sulfate or other glycosaminoglycans and mediate their endocytosis through the clathrin-coated pit pathway. The differences in their membrane and cytoplasmic domains also raise the possibility that the members of this family could interact with different membrane or cytoplasmic regulatory factors and consequently process or route these bound ligands through different intracellular pathways.

Our current model for HA turnover in mammals (FIG. 38) highlights the role of HARE in liver and lymph node and to a lesser extent in spleen. HARE mediates the uptake of HA into these tissues so it can be removed from the lymph or blood and degraded. A large fraction of the ~5 g of HA turned over daily by humans is probably derived from skin, which contains about 50% of our total body HA (Abatangelo and Weigel, *New Frontiers in Medical Sciences: Redefining Hyaluronan* (2000); Laurent and Fraser, *FASEB J.* 6:2397 (1992)) and which remarkably, has a half-life of only ~one day (Tammi et al, *J. Invest. Dermatol.* 97:126 (1991)). Presently there are important clinical uses for HA-containing devices in treating wounds and osteoarthritis and in eye surgery (Laurent and Fraser, *FASEB J.* 6:2397 (1992); Panay and Lower, *Curr. Opin. Obstet Gynecol.* 11:379 (1999)). Additional future uses of HA in clinical applications are likely to be developed based on our growing understanding of the biology of HA and its multiple roles in wound healing (Iocona et al, *J. Surg. Res.* 76:111 (1998); Chen and Abatangelo, *Wound Repair Regen.* 7:79 (1999)), angiogenesis (West et al, *Science,* 14:1324 (1985); Deed et al, *Int. J. Cancer,* 71:251 (1997); Rahmanian et al, *Exp. Cell Res.* 237:223 (1997)), macrophage activation (Horton et al, *J. Biol. Chem.* 273:35088 (1998); Horton et al, *Am. J. Physiol. Lung Cell Mol. Physiol.* 279:707 (2000)) and metastasis (Csoka et al, *Invasion Metastasis,* 17:297 (1997); Delpech et al, *J. Intern. Med.* 242:41 (1997)). A variety of different drug delivery systems utilizing HA are also being developed (Cantor et al, *Proc. Soc. Exp. Biol. Med.* 217:471 (1998); Illum et al, *J. Control Release,* 29:133 (1994); Luo et al, *J. Control Release,* 69:169 (2000)). Given the likely increase in the clinical uses of HA-containing devices and drugs it is important that we now understand the overall mechanism of HA turnover in the body. In particular, the present molecular identification and characterization of the human HA Receptor for Endocytosis responsible for HA clearance is timely and should facilitate further studies in this field.

The human gene encoding HARE, which is in the genome database (under accession # NT_024383.2), is located on chromosome 12 and appears to be a highly fragmented and unusual gene. The HARE coding region for the 1394 amino acids reported here is present as about 37 exons, most of which are only 100-200 bp long, distributed relatively regularly over a ~171 kb region (see FIG. 38 and Table VII). The mouse gene is similarly organized.

Thus it should be apparent that there has been provided in accordance with the present invention a purified nucleic acid segment having a coding region encoding functionally active HARE, methods of producing HARE from the HARE gene, methods of purifying HARE, and the use of fragments of HARE that specifically bind HA, chondroitin and chondroitin sulfate, that fully satisfies the objectives and advantages set forth above. Although the invention has been described in conjunction with specific embodiments thereof, it is evident that many alternatives, modifications, and variations will be apparent to those skilled in the art. Accordingly, it is intended to embrace all such alternatives, modifications, and variations that fall within the spirit and broad scope of the appended claims.

What is claimed is:

1. A purified nucleic acid segment comprising a coding region encoding a functionally active Hyaluronic Acid Receptor for Endocytosis (HARE), wherein the purified nucleic acid segment comprises the nucleotide sequence in accordance with SEQ ID NO:1.

2. A recombinant vector selected from the group consisting of a plasmid, cosmid, phage, or virus vector and wherein the recombinant vector further comprises the purified nucleic acid segment of claim 1.

3. The recombinant vector of claim 2, wherein the plasmid is an expression vector.

4. The recombinant vector of claim 3, wherein the expression vector comprises a promoter operatively linked to the HARE coding region.

5. A recombinant host cell, comprising the recombinant vector of claim 2.

6. The recombinant host cell of claim 5, wherein the host cell is a eucaryotic cell.

7. The recombinant host cell of claim 5, wherein the recombinant host cell produces a functionally active HARE which specifically binds and endocytoses at least one of HA, chondroitin, and chondroitin sulfate.

8. The recombinant host cell of claim 5, wherein the purified nucleic acid segment is integrated into a chromosome of the recombinant host cell.

9. A method of producing a functionally active Hyaluronic Acid Receptor for Endocytosis (HARE) wherein the HARE is able to specifically bind at least one of HA, chondroitin, and chondroitin sulfate, the method comprising the steps of:
 providing the recombinant host cell of claim 5;
 culturing the recombinant host cell under conditions that allow for expression of the recombinant DNA segment encoding a functionally active HARE, thereby producing functionally active HARE; and
 separating and purifying the functionally active HARE from the recombinant host cell.

10. A purified nucleic acid segment comprising a coding region encoding a functionally active Hyaluronic Acid Receptor for Endocytosis (HARE), wherein the purified nucleic acid segment comprises a nucleotide sequence encoding the amino acid sequence of SEQ ID NO:2.

11. A recombinant vector selected from the group consisting of a plasmid, cosmid, phage, or virus vector and wherein the recombinant vector further comprises the purified nucleic acid segment of claim 10.

12. The recombinant vector of claim 11, wherein the plasmid is an expression vector.

13. The recombinant vector of claim 12, wherein the expression vector comprises a promoter operatively linked to the HARE coding region.

14. A recombinant host cell, comprising the recombinant vector of claim 11.

15. The recombinant host cell of claim 14, wherein the host cell is a eucaryotic cell.

16. The recombinant host cell of claim 14, wherein the recombinant host cell produces a functionally active HARE which specifically binds and endocytoses at least one of HA, chondroitin, and chondroitin sulfate.

17. The recombinant host cell of claim 14, wherein the purified nucleic acid segment is integrated into a chromosome of the recombinant host cell.

18. A method of producing a functionally active Hyaluronic Acid Receptor for Endocytosis (HARE) wherein the HARE is able to specifically bind at least one of HA, chondroitin, and chondroitin sulfate, the method comprising the steps of:
 providing the recombinant host cell of claim 14;
 culturing the recombinant host cell under conditions that allow for expression of the recombinant DNA segment encoding a functionally active HARE, thereby producing functionally active HARE; and
 separating and purifying the functionally active HARE from the recombinant host cell.

\* \* \* \* \*

UNITED STATES PATENT AND TRADEMARK OFFICE
CERTIFICATE OF CORRECTION

PATENT NO. : 7,507,556 B2
APPLICATION NO. : 10/990844
DATED : March 21, 2009
INVENTOR(S) : Paul H. Weigel, Janet Weigel and Bin Zhou It is certified that error appears in the above-identified patent and that said Letters Patent is hereby corrected as shown below:

Column 14, line 21: Delete ""™nucleic acid segments ™," and replace with -- "nucleic acid segment," --

Column 14, line 22: Delete ""™DNA segment ™" and replace with -- "DNA segment" --

Column 14, line 25: Delete ""™purified ™" and replace with -- "purified" --

Column 14, line 27: Delete "(™HARE ™)" and replace with -- ("HARE") --

Column 14, line 31: Delete ""™DNA segment™" and replace with -- "DNA segment" --

Column 14, line 39: Delete ""™gene™" and replace with -- "gene" --

Column 14, line 43: Delete ""™Isolated" and replace with -- "Isolated --

Column 14, line 44: Delete "sequence™" and replace with -- sequences" --

Column 15, line 32: Delete ""™a sequence" and replace with -- "a sequence --

Column 15, line 32: Delete "NO:2™" and replace with -- NO:2" --

Column 15, line 33: Delete "NO:25™" and replace with -- NO:25" -

Column 15, line 38: Delete ""™biologi-" and replace with -- "biologi- --

Column 15, line 39: Delete "equivalent™" and replace with -- equivalent" --

UNITED STATES PATENT AND TRADEMARK OFFICE
CERTIFICATE OF CORRECTION

PATENT NO. : 7,507,556 B2
APPLICATION NO. : 10/990844
DATED : March 21, 2009
INVENTOR(S) : Paul H. Weigel, Janet Weigel and Bin Zhou It is certified that error appears in the above-identified patent and that said Letters Patent is hereby corrected as shown below:

Column 16, line 34: Delete ""™recombinant vector™"" and replace with -- "recombinant vector" --

Column 16, line 56: Delete ""™engineered™ or ™recombinant™"" and replace with -- "engineered" or "recombinant" --

Column 17, line 13: Delete ""™replicons™"" and replace with -- "replicons" --

Column 18, line 15: Delete ""™essentially as set forth in SEQ ID NO:1 ™ or ™ essentially" and replace with -- "essentially as set forth in SEQ ID NO:1" or "essentially --

Column 18, line 16: Delete "NO:24 ™"" and replace with -- NO:24" --

Column 18, line 22: Delete ""™ functionally equivalent codon ™"" and replace with -- "functionally equivalent codon" --

Column 18, line 46: Delete ""™essentially" and replace with -- "essentially --

Column 18, line 47: Delete "NO:1 ™ or ™essentially" and replace with -- NO:1" or "essentially --

Column 18, line 48: Delete "NO:24 ™"" and replace with -- NO:24" --

Column 18, line 56: Delete ""™standard hybridization conditions™"" and replace with -- "standard hybridization conditions" --

UNITED STATES PATENT AND TRADEMARK OFFICE
CERTIFICATE OF CORRECTION

PATENT NO. : 7,507,556 B2
APPLICATION NO. : 10/990844
DATED : March 21, 2009
INVENTOR(S) : Paul H. Weigel, Janet Weigel and Bin Zhou It is certified that error appears in the above-identified patent and that said Letters Patent is hereby corrected as shown below:

Column 19, lines 31 and 32: Delete "™complementary™"
and replace with -- "complementary" --

Column 19, line 34: Delete "™ complementary sequences™"
and replace with -- "complentary sequences" --

Column 26, line 15: Delete "100,00xg," and replace with -- 100,000Xg, --

Column 53, line 12: Delete "FELLS." and replace with -- FELLs. --

Signed and Sealed this

Twenty-third Day of June, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,507,556 B2
APPLICATION NO. : 10/990844
DATED : March 24, 2009
INVENTOR(S) : Paul H. Weigel, Janet Weigel and Bin Zhou It is certified that error appears in the above-identified patent and that said Letters Patent is hereby corrected as shown below:

Column 14, line 21: Delete ""™nucleic acid segments ™," and replace with -- "nucleic acid segment," --

Column 14, line 22: Delete ""™DNA segment ™" and replace with -- "DNA segment" --

Column 14, line 25: Delete ""™purified ™" and replace with -- "purified" --

Column 14, line 27: Delete "(™HARE ™)" and replace with -- ("HARE") --

Column 14, line 31: Delete ""™DNA segment™" and replace with -- "DNA segment" --

Column 14, line 39: Delete ""™gene™" and replace with -- "gene" --

Column 14, line 43: Delete ""™Isolated" and replace with -- "Isolated --

Column 14, line 44: Delete "sequence™" and replace with -- sequences" --

Column 15, line 32: Delete ""™a sequence" and replace with -- "a sequence --

Column 15, line 32: Delete "NO:2™" and replace with -- NO:2" --

Column 15, line 33: Delete "NO:25™" and replace with -- NO:25" -

Column 15, line 38: Delete ""™biologi-" and replace with -- "biologi- --

Column 15, line 39: Delete "equivalent™" and replace with -- equivalent" --

UNITED STATES PATENT AND TRADEMARK OFFICE
CERTIFICATE OF CORRECTION

PATENT NO. : 7,507,556 B2
APPLICATION NO. : 10/990844
DATED : March 24, 2009
INVENTOR(S) : Paul H. Weigel, Janet Weigel and Bin Zhou It is certified that error appears in the above-identified patent and that said Letters Patent is hereby corrected as shown below:

Column 16, line 34: Delete ""™recombinant vector™"" and replace with -- "recombinant vector" --

Column 16, line 56: Delete ""™engineered™ or ™recombinant™"" and replace with -- "engineered" or "recombinant" --

Column 17, line 13: Delete ""™replicons™" and replace with -- "replicons" --

Column 18, line 15: Delete ""™essentially as set forth in SEQ ID NO:1 ™ or ™ essentially" and replace with -- "essentially as set forth in SEQ ID NO:1" or "essentially --

Column 18, line 16: Delete "NO:24 ™" and replace with -- NO:24" --

Column 18, line 22: Delete ""™ functionally equivalent codon ™"" and replace with -- "functionally equivalent codon" --

Column 18, line 46: Delete ""™essentially" and replace with -- "essentially --

Column 18, line 47: Delete "NO:1 ™ or ™essentially" and replace with -- NO:1" or "essentially --

Column 18, line 48: Delete "NO:24 ™" and replace with -- NO:24" --

Column 18, line 56: Delete ""™standard hybridization conditions™"" and replace with -- "standard hybridization conditions" --

UNITED STATES PATENT AND TRADEMARK OFFICE
CERTIFICATE OF CORRECTION

PATENT NO. : 7,507,556 B2
APPLICATION NO. : 10/990844
DATED : March 24, 2009
INVENTOR(S) : Paul H. Weigel, Janet Weigel and Bin Zhou It is certified that error appears in the above-identified patent and that said Letters Patent is hereby corrected as shown below:

Column 19, lines 31 and 32: Delete "™complementary™"
 and replace with -- "complementary" --

Column 19, line 34: Delete "™ complementary sequences™"
 and replace with -- "complementary sequences" --

Column 26, line 15: Delete "100,00xg," and replace with -- 100,000Xg, --

Column 53, line 12: Delete "FELLS." and replace with -- FELLs. --

This certificate supersedes the Certificate of Correction issued June 23, 2009.

Signed and Sealed this

Twenty-first Day of July, 2009

JOHN DOLL
*Acting Director of the United States Patent and Trademark Office*

SEQUENCE LISTING

```
<160> NUMBER OF SEQ ID NOS: 56

<210> SEQ ID NO 1
<211> LENGTH: 4706
<212> TYPE: DNA
<213> ORGANISM: Rattus norvegicus

<400> SEQUENCE: 1
tctttaccaa gtctactcac ccgtctggag cagatgcccg actattccat tttccgaggt      60
tacattattc attacaacct ggcaagtgca atcgagtctg cagatgctta tactgtgttc     120
gtgccaaaca atgaagccat cgaaaactat atcagggaga agaaagccac atctctaaag     180
gaagatattc tacggtacca tgtggtcctg ggggaaaagc tcctgaagaa tgacttgcat     240
aacggcatgc accgagagac catgctgggg ttctcctacc tccttgcctt ctttctccgc     300
aatgaccagc tgtatgtaaa tgaagctcca ataaactaca ccaatgtggc cactgataaa     360
ggagtgatcc atggtctgga gaaagttctg gaaattcaga agaacagatg tgacaataat     420
gacaccatta ttgtgagagg ggagtgtgga aagtgttccc agcaagcccc ctgcccactc     480
```

```
gagacaaaac cacttagaga gacgaggaaa tgcatctatt ccatctactt catggggaag    540
agatccgtat tcatcgggtg ccagccacag tgtgtgagaa ccatcattac aagagcctgc    600
tggctggctt ctttggccca caatgccaag cctgccccgg gagaggtcaa aatgtgtgct    660
ctgggaacgg cttctgtctg ggacggtgtg aatggcactg gcacgtgcca gtgcgggctg    720
ggcttcaatg ggacagcctg tgaaacctgc actgagggga agtatggtat ccactgcgac    780
caagcatgct cttgtgtcca tgggagatgt agccaaggac ccttgggaga cggctcctgt    840
gactgtgacg tcggctggcg aggagtgaag tgtgacatgg agatcaccac agacaactgc    900
aacgggacct gtcacaccag tgccaactgc cttctggatc cagacggcaa agcctcgtgc    960
aaatgtgcgg caggattccg agggaatgga acggtctgca cagccatcaa tgcctgtgag   1020
accagcaatg gaggatgttc tacaaaggcc gactgtaaaa gaaccacccc aggaaaccgg   1080
gtgtgtgtgt gcaaggcagg ctataccggc gacggcatcg tgtgccttga aatcaacccg   1140
tgtttggaga accatggtgg ctgtgacaga aatgcagagt gcacacagac agggcccaac   1200
caggccgtct gtaactgctt gccgaagtac actggagatg gaaaggtctg ctcgcttatc   1260
aatgtctgcc taacgaacaa tggcggctgc agtccatttg ccttctgcaa ctacactgag   1320
caagatcaaa ggatatgtac ctgcaagcca gactacacgg gtgatggaat cgtctgccgg   1380
ggcagcatct acggggagct tcccaagaac ccttcgacgt cccagtactt cttccagttg   1440
caggagcatg ctgtccgaga gcttgctgga cctggcccct tcaccgtgtt cgcgcctttg   1500
tctagctcct tcaatcatga gccccggatt aaagactggg atcagcaggg cctcatgtcc   1560
caggttcttc gctatcacgt ggtgggctgc agcagctgc tgttggacaa cctaaaagtg   1620
accacaagtg ccacgaccct ccaaggagag ccagtttcca tctctgtctc tcaggacact   1680
gtgttcataa acaatgaggc gaaggtcctg tccagtgaca tcatcagcac caatggcgtc   1740
atccacgtta tagacaagtt gctgtctccc aaaaacttgc ttatcacccc caaagatgcc   1800
ttgggcaggg ttctgcaaaa tcttactaca gtggcagcaa ccacggata taccaaattc   1860 agcaagttga tacaggactc aggcttgctg tcagtcatca ctgactccat ccacaccccca   1920 gtcactgtct tctggcctac ggacaaagcc ctggaagcct tgcccccaga gcagcaggac   1980
ttcctgttca atcaagacaa caaggacaag ctgaagtctt acctgaagtt ccacgtgatc   2040
cgagactcca aggctttagc ttcagacctc cccaggtctg cttcctggaa gaccctgcaa   2100
ggctcagagc tgagtgtgag gtgtggaact ggcagtgaca tcggtgagct ctttctaaac   2160
gaacaaatgt gcagattcat acaccgggga ctcttgtttg acgtgggtgt ggcctatggc   2220
attgactgcc tactcatgaa tcctacccta ggtggccgat gtgacacttt tactaccttc   2280
gatattccgg gggagtgcgg aagttgcatt ttcactccca aatgcccact gaagagcaag   2340
ccaaagggcg tgaagaagaa gtgtatctac aacccgttac ctttcaggag gaacgtggaa   2400
ggctgccaga acctgtgcac cgtggtgatc caaaccccca ggtgctgcca tggttacttc   2460
atgccagact gtcaggcctg ccctggagga ccagatacac cgtgtaacaa ccggggcatg   2520
tgccgcgatc tgtacacacc catgggacag tgcctatgcc acaccggctt caacgggaca   2580
gcctgcgagc tctgctggca tgggagattt gggcctgact gtcagccccg cagctgctcc   2640
gagcatggac agtgtgatga ggggatcaca ggctccgggg agtgcctctg tgaaacaggg   2700
tggacagccg cttcgtgtga cactcccaca gctgtattcg cagtgtgcac acctgcttgc   2760
tccgtgcacg ccacctgtac ggagaacaac acgtgtgtgt gtaacttgaa ctacgaaggt   2820
gacgggatca catgcacagt cgtggacttc tgcaaacaga acaacggggg ctgtgcgaag   2880
```

```
gtcgctaagt gctcccagaa aggcacccaa gtctcttgca gctgcaagaa aggctacaag    2940
ggggatggct acagctgcat agagatagac ccctgtgcag acggtgtcaa cggggatgc     3000
catgagcacg ccacctgcag gatgacgggc caggcaagc ataagtgtga atgtaaaagt     3060
cactatgtcg gggacggagt ggactgtgag cctgagcagc tgccgctcga ccgttgctta   3120
caggacaacg gacagtgcca cccagatgcc agctgtgcag acctctactt ccaggacacg   3180
accgtaggag tattccatct acgctcccca ctgggccagt acaaactgac atttgacaaa   3240
gccaaagaag cctgtgccaa agaagctgcg accatagcca cctacaacca gctctcctat   3300
gcccagaagg ccaagtatca cctgtgctcg gccggctggc tggagagtgg gcgggttgcc   3360
tacccgacta cgtatgcctc tcagaagtgt ggtgcaaacg ttgttgggat cgtagactac   3420
ggatccaggg ccaacaagag tgaaatgtgg gatgtcttct gttaccggat gaaagatgtg   3480
aactgcacct gcaaggcagg ctatgtggga gatggcttct cgtgcagtgg gaacctgctg   3540
caggtcctca tgtccttccc ctcgctcaca aacttcctga cagaggtgct ggcttttcc    3600
aagagctcag cccgaggaca ggcatttttg aaacacctga ctgacctgtc catccgtggc   3660
accctgtttg tgccacagaa cagtgggcta ccgggaaata gagcctgtc tggccgggac   3720
attgagcacc acctcactaa tgtcaacgtc ccttttaca atgaccttgt caatggtacc   3780
tttctgagga ctatgctggg aagccaactg ctcattacct tcagccagga ccagctccac   3840
caagagacca ggtttgtgga tggaagatcc attctgcagt gggacatcat cgccgccaat   3900
ggaatcctcc atattatttc tgaacctttg agagctcctc ccacggcagc aacggctgcc   3960
cactctggcc tggggacagg tatattctgt gccgtcgtcc tggtcactgg tgcgattgct   4020
ctggcagctt actcttactt ccggctaaag cagcgaacca ctggttttcca gcgttttgat  4080
cagaagagga cattgatgtc ttggcttttg gcaagcagca gcccaagaat atcgcaaacc   4140
ctctgtatga gacctcagcg ccggcacccc cagagtcctc ctgtgacccc ttcacagacc   4200
ctggagaaca ggatctggag gacagcgacc ctctgggggc actgcggtcc tgacatgaga   4260
agccagcaag caaccacagt cacggttcca cggtgattcc cagccccagc tgtctcatgg   4320
atcagttgtt ttaaagaatg acaacactca taagccagcc atacctcacc cttctggtta   4380
atctgggatt gtcgccaggg ctaaggagcc atgttgcctg atacctgggg gacctccac    4440
ctcctctgag cctataccgt ggttctctca cttccatatg gtgcttggtc tgttctgccc   4500
tctcttgtac ccacaaactg tgactctgtg gtattctcct attgacgtaa gcaccaaagg   4560
cggggcttca cctcttatgt tctgtattcc agtacccaga agtacctgcc acacatgtgt   4620
gctcaataaa tgttttggga acaaaataaa gaaggcactg tgtacctaga aggtgtcaaa   4680
ctatgaaagc aaaaaaaaaa aaaaaa                                        4706
```

<210> SEQ ID NO 2
<211> LENGTH: 1431
<212> TYPE: PRT
<213> ORGANISM: Rattus norvegicus

<400> SEQUENCE: 2

```
Ser Leu Pro Ser Leu Leu Thr Arg Leu Glu Gln Met Pro Asp Tyr Ser
1               5                   10                  15

Ile Phe Arg Gly Tyr Ile Ile His Tyr Asn Leu Ala Ser Ala Ile Glu
                20                  25                  30

Ser Ala Asp Ala Tyr Thr Val Phe Val Pro Asn Asn Glu Ala Ile Glu
            35                  40                  45
```

```
Asn Tyr Ile Arg Glu Lys Lys Ala Thr Ser Leu Lys Glu Asp Ile Leu
         50                  55                  60

Arg Tyr His Val Val Leu Gly Glu Lys Leu Leu Lys Asn Asp Leu His
 65                  70                  75                  80

Asn Gly Met His Arg Glu Thr Met Leu Gly Phe Ser Tyr Leu Leu Ala
                 85                  90                  95

Phe Phe Leu Arg Asn Asp Gln Leu Tyr Val Asn Glu Ala Pro Ile Asn
            100                 105                 110

Tyr Thr Asn Val Ala Thr Asp Lys Gly Val Ile His Gly Leu Glu Lys
        115                 120                 125

Val Leu Glu Ile Gln Lys Asn Arg Cys Asp Asn Asp Thr Ile Ile
    130                 135                 140

Val Arg Gly Glu Cys Gly Lys Cys Ser Gln Ala Pro Cys Pro Leu
145                 150                 155                 160

Glu Thr Lys Pro Leu Arg Glu Thr Arg Lys Cys Ile Tyr Ser Ile Tyr
                165                 170                 175

Phe Met Gly Lys Arg Ser Val Phe Ile Gly Cys Gln Pro Gln Cys Val
            180                 185                 190

Arg Thr Ile Ile Thr Arg Ala Cys Trp Leu Ala Ser Leu Ala His Asn
        195                 200                 205

Ala Lys Pro Ala Pro Gly Glu Val Lys Met Cys Ala Leu Gly Thr Ala
    210                 215                 220

Ser Val Trp Asp Gly Val Asn Gly Thr Gly Thr Cys Gln Cys Gly Leu
225                 230                 235                 240

Gly Phe Asn Gly Thr Ala Cys Glu Thr Cys Thr Glu Gly Lys Tyr Gly
                245                 250                 255

Ile His Cys Asp Gln Ala Cys Ser Cys Val His Gly Arg Cys Ser Gln
            260                 265                 270

Gly Pro Leu Gly Asp Gly Ser Cys Asp Cys Asp Val Gly Trp Arg Gly
        275                 280                 285

Val Lys Cys Asp Met Glu Ile Thr Thr Asp Asn Cys Asn Gly Thr Cys
    290                 295                 300

His Thr Ser Ala Asn Cys Leu Leu Asp Pro Asp Gly Lys Ala Ser Cys
305                 310                 315                 320

Lys Cys Ala Ala Gly Phe Arg Gly Asn Gly Thr Val Cys Thr Ala Ile
                325                 330                 335

Asn Ala Cys Glu Thr Ser Asn Gly Gly Cys Ser Thr Lys Ala Asp Cys
            340                 345                 350

Lys Arg Thr Thr Pro Gly Asn Arg Val Cys Val Cys Lys Ala Gly Tyr
        355                 360                 365

Thr Gly Asp Gly Ile Val Cys Leu Glu Ile Asn Pro Cys Leu Glu Asn
    370                 375                 380

His Gly Gly Cys Asp Arg Asn Ala Glu Cys Thr Gln Thr Gly Pro Asn
385                 390                 395                 400

Gln Ala Val Cys Asn Cys Leu Pro Lys Tyr Thr Gly Asp Gly Lys Val
                405                 410                 415

Cys Ser Leu Ile Asn Val Cys Leu Thr Asn Asn Gly Gly Cys Ser Pro
            420                 425                 430

Phe Ala Phe Cys Asn Tyr Thr Glu Gln Asp Gln Arg Ile Cys Thr Cys
        435                 440                 445

Lys Pro Asp Tyr Thr Gly Asp Gly Ile Val Cys Arg Gly Ser Ile Tyr
    450                 455                 460
```

-continued

```
Gly Glu Leu Pro Lys Asn Pro Ser Thr Ser Gln Tyr Phe Phe Gln Leu
465                 470                 475                 480

Gln Glu His Ala Val Arg Glu Leu Ala Gly Pro Gly Pro Phe Thr Val
                485                 490                 495

Phe Ala Pro Leu Ser Ser Phe Asn His Glu Pro Arg Ile Lys Asp
            500                 505                 510

Trp Asp Gln Gln Gly Leu Met Ser Gln Val Leu Arg Tyr His Val Val
                515                 520                 525

Gly Cys Gln Gln Leu Leu Leu Asp Asn Leu Lys Val Thr Thr Ser Ala
530                 535                 540

Thr Thr Leu Gln Gly Glu Pro Val Ser Ile Ser Val Ser Gln Asp Thr
545                 550                 555                 560

Val Phe Ile Asn Asn Glu Ala Lys Val Leu Ser Ser Asp Ile Ile Ser
                565                 570                 575

Thr Asn Gly Val Ile His Val Ile Asp Lys Leu Leu Ser Pro Lys Asn
                580                 585                 590

Leu Leu Ile Thr Pro Lys Asp Ala Leu Gly Arg Val Leu Gln Asn Leu
            595                 600                 605

Thr Thr Val Ala Ala Asn His Gly Tyr Thr Lys Phe Ser Lys Leu Ile
610                 615                 620

Gln Asp Ser Gly Leu Leu Ser Val Ile Thr Asp Ser Ile His Thr Pro
625                 630                 635                 640

Val Thr Val Phe Trp Pro Thr Asp Lys Ala Leu Glu Ala Leu Pro Pro
                645                 650                 655

Glu Gln Gln Asp Phe Leu Phe Asn Gln Asp Asn Lys Asp Lys Leu Lys
                660                 665                 670

Ser Tyr Leu Lys Phe His Val Ile Arg Asp Ser Lys Ala Leu Ala Ser
            675                 680                 685

Asp Leu Pro Arg Ser Ala Ser Trp Lys Thr Leu Gln Gly Ser Glu Leu
            690                 695                 700

Ser Val Arg Cys Gly Thr Gly Ser Asp Ile Gly Glu Leu Phe Leu Asn
705                 710                 715                 720

Glu Gln Met Cys Arg Phe Ile His Arg Gly Leu Leu Phe Asp Val Gly
                725                 730                 735

Val Ala Tyr Gly Ile Asp Cys Leu Leu Met Asn Pro Thr Leu Gly Gly
                740                 745                 750

Arg Cys Asp Thr Phe Thr Thr Phe Asp Ile Pro Gly Glu Cys Gly Ser
            755                 760                 765

Cys Ile Phe Thr Pro Lys Cys Pro Leu Lys Ser Lys Pro Lys Gly Val
770                 775                 780

Lys Lys Lys Cys Ile Tyr Asn Pro Leu Pro Phe Arg Arg Asn Val Glu
785                 790                 795                 800

Gly Cys Gln Asn Leu Cys Thr Val Val Ile Gln Thr Pro Arg Cys Cys
                805                 810                 815

His Gly Tyr Phe Met Pro Asp Cys Gln Ala Cys Pro Gly Gly Pro Asp
            820                 825                 830

Thr Pro Cys Asn Asn Arg Gly Met Cys Arg Asp Leu Tyr Thr Pro Met
            835                 840                 845

Gly Gln Cys Leu Cys His Thr Gly Phe Asn Gly Thr Ala Cys Glu Leu
            850                 855                 860

Cys Trp His Gly Arg Phe Gly Pro Asp Cys Gln Pro Arg Ser Cys Ser
865                 870                 875                 880

Glu His Gly Gln Cys Asp Glu Gly Ile Thr Gly Ser Gly Glu Cys Leu
```

-continued

```
            885              890              895
Cys Glu Thr Gly Trp Thr Ala Ala Ser Cys Asp Thr Pro Thr Ala Val
            900              905              910

Phe Ala Val Cys Thr Pro Ala Cys Ser Val His Ala Thr Cys Thr Glu
            915              920              925

Asn Asn Thr Cys Val Cys Asn Leu Asn Tyr Glu Gly Asp Gly Ile Thr
            930              935              940

Cys Thr Val Val Asp Phe Cys Lys Gln Asn Asn Gly Cys Ala Lys
945              950              955              960

Val Ala Lys Cys Ser Gln Lys Gly Thr Gln Val Ser Cys Ser Cys Lys
            965              970              975

Lys Gly Tyr Lys Gly Asp Gly Tyr Ser Cys Ile Glu Ile Asp Pro Cys
            980              985              990

Ala Asp Gly Val Asn Gly Gly Cys His Glu His Ala Thr Cys Arg Met
            995             1000             1005

Thr Gly Pro Gly Lys His Lys Cys Glu Cys Lys Ser His Tyr Val
           1010             1015             1020

Gly Asp Gly Val Asp Cys Glu Pro Glu Gln Leu Pro Leu Asp Arg
           1025             1030             1035

Cys Leu Gln Asp Asn Gly Gln Cys His Pro Asp Ala Ser Cys Ala
           1040             1045             1050

Asp Leu Tyr Phe Gln Asp Thr Thr Val Gly Val Phe His Leu Arg
           1055             1060             1065

Ser Pro Leu Gly Gln Tyr Lys Leu Thr Phe Asp Lys Ala Lys Glu
           1070             1075             1080

Ala Cys Ala Lys Glu Ala Ala Thr Ile Ala Thr Tyr Asn Gln Leu
           1085             1090             1095

Ser Tyr Ala Gln Lys Ala Lys Tyr His Leu Cys Ser Ala Gly Trp
           1100             1105             1110

Leu Glu Ser Gly Arg Val Ala Tyr Pro Thr Thr Tyr Ala Ser Gln
           1115             1120             1125

Lys Cys Gly Ala Asn Val Val Gly Ile Val Asp Tyr Gly Ser Arg
           1130             1135             1140

Ala Asn Lys Ser Glu Met Trp Asp Val Phe Cys Tyr Arg Met Lys
           1145             1150             1155

Asp Val Asn Cys Thr Cys Lys Ala Gly Tyr Val Gly Asp Gly Phe
           1160             1165             1170

Ser Cys Ser Gly Asn Leu Leu Gln Val Leu Met Ser Phe Pro Ser
           1175             1180             1185

Leu Thr Asn Phe Leu Thr Glu Val Leu Ala Phe Ser Lys Ser Ser
           1190             1195             1200

Ala Arg Gly Gln Ala Phe Leu Lys His Leu Thr Asp Leu Ser Ile
           1205             1210             1215

Arg Gly Thr Leu Phe Val Pro Gln Asn Ser Gly Leu Pro Gly Asn
           1220             1225             1230

Lys Ser Leu Ser Gly Arg Asp Ile Glu His His Leu Thr Asn Val
           1235             1240             1245

Asn Val Ser Phe Tyr Asn Asp Leu Val Asn Gly Thr Phe Leu Arg
           1250             1255             1260

Thr Met Leu Gly Ser Gln Leu Leu Ile Thr Phe Ser Gln Asp Gln
           1265             1270             1275

Leu His Gln Glu Thr Arg Phe Val Asp Gly Arg Ser Ile Leu Gln
           1280             1285             1290
```

```
Trp Asp Ile Ile Ala Ala Asn Gly Ile Leu His Ile Ile Ser Glu
    1295                1300                1305

Pro Leu Arg Ala Pro Pro Thr Ala Ala Thr Ala Ala His Ser Gly
    1310                1315                1320

Leu Gly Thr Gly Ile Phe Cys Ala Val Val Leu Val Thr Gly Ala
    1325                1330                1335

Ile Ala Leu Ala Ala Tyr Ser Tyr Phe Arg Leu Lys Gln Arg Thr
    1340                1345                1350

Thr Gly Phe Gln Arg Phe Asp Gln Lys Arg Thr Leu Met Ser Trp
    1355                1360                1365

Leu Leu Ala Ser Ser Ser Pro Arg Ile Ser Gln Thr Leu Cys Met
    1370                1375                1380

Arg Pro Gln Arg Arg His Pro Gln Ser Pro Pro Val Thr Pro Ser
    1385                1390                1395

Gln Thr Leu Glu Asn Arg Ile Trp Arg Thr Ala Thr Leu Trp Gly
    1400                1405                1410

His Cys Gly Pro Asp Met Arg Ser Gln Gln Ala Thr Thr Val Thr
    1415                1420                1425

Val Pro Arg
    1430

<210> SEQ ID NO 3
<211> LENGTH: 20
<212> TYPE: DNA
<213> ORGANISM: Rattus norvegicus
<220> FEATURE:
<221> NAME/KEY: misc_feature
<222> LOCATION: (3)..(3)
<223> OTHER INFORMATION: a or g or c or t
<220> FEATURE:
<221> NAME/KEY: misc_feature
<222> LOCATION: (9)..(9)
<223> OTHER INFORMATION: a or g or c or t
<220> FEATURE:
<221> NAME/KEY: misc_feature
<222> LOCATION: (12)..(12)
<223> OTHER INFORMATION: a or g or c or t
<220> FEATURE:
<221> NAME/KEY: misc_feature
<222> LOCATION: (6)..(6)
<223> OTHER INFORMATION: t or c
<220> FEATURE:
<221> NAME/KEY: misc_feature
<222> LOCATION: (18)..(18)
<223> OTHER INFORMATION: modified_base
<220> FEATURE:
<221> NAME/KEY: modified_base
<222> LOCATION: (18)..(18)
<223> OTHER INFORMATION: I
<220> FEATURE:
<221> NAME/KEY: misc_feature
<222> LOCATION: (15)..(15)
<223> OTHER INFORMATION: t or c

<400> SEQUENCE: 3
ccnttyacng tnttygcncc                                         20

<210> SEQ ID NO 4
<211> LENGTH: 21
<212> TYPE: DNA
<213> ORGANISM: Rattus norvegicus

<400> SEQUENCE: 4
ggcatacgta gtcgggtagg c                                       21
```

```
<210> SEQ ID NO 5
<211> LENGTH: 24
<212> TYPE: DNA
<213> ORGANISM: Homo sapiens

<400> SEQUENCE: 5
tcaatataat ctggcgaatg caat                                          24

<210> SEQ ID NO 6
<211> LENGTH: 21
<212> TYPE: DNA
<213> ORGANISM: Homo sapiens

<400> SEQUENCE: 6
ggtgccagct gaagagtaca a                                             21

<210> SEQ ID NO 7
<211> LENGTH: 24
<212> TYPE: DNA
<213> ORGANISM: Homo sapiens

<400> SEQUENCE: 7
agttccgaat gggcaggtca gctc                                          24

<210> SEQ ID NO 8
<211> LENGTH: 6
<212> TYPE: PRT
<213> ORGANISM: Rattus norvegicus

<400> SEQUENCE: 8

Pro Leu Gly Gln Tyr Lys
1               5

<210> SEQ ID NO 9
<211> LENGTH: 10
<212> TYPE: PRT
<213> ORGANISM: Rattus norvegicus

<400> SEQUENCE: 9

Ala Tyr Pro Thr Thr Tyr Ala Ser Gln Lys
1               5                   10

<210> SEQ ID NO 10
<211> LENGTH: 16
<212> TYPE: PRT
<213> ORGANISM: Rattus norvegicus

<400> SEQUENCE: 10

Val Leu Gln Asp Leu Thr Thr Val Ala Ala Asn His Gly Tyr Thr Lys
1               5                   10                  15

<210> SEQ ID NO 11
<211> LENGTH: 18
<212> TYPE: PRT
<213> ORGANISM: Rattus norvegicus

<400> SEQUENCE: 11

Gln Leu Tyr Val Asn Glu Ala Pro Ile Asp Tyr Thr Asn Val Ala Thr
1               5                   10                  15

Asp Lys

<210> SEQ ID NO 12
<211> LENGTH: 22
```

```
<212> TYPE: PRT
<213> ORGANISM: Rattus norvegicus

<400> SEQUENCE: 12

Leu Ala Gly Pro Gly Pro Phe Thr Val Phe Ala Pro Leu Ser Ser Ser
1               5                   10                  15

Phe Asn His Glu Pro Arg
            20

<210> SEQ ID NO 13
<211> LENGTH: 12
<212> TYPE: PRT
<213> ORGANISM: Rattus norvegicus

<400> SEQUENCE: 13

Asp Ile Leu Arg Tyr His Val Val Leu Gly Glu Lys
1               5                   10

<210> SEQ ID NO 14
<211> LENGTH: 6
<212> TYPE: PRT
<213> ORGANISM: Rattus norvegicus

<400> SEQUENCE: 14

Val Leu Glu Ile Asn Lys
1               5

<210> SEQ ID NO 15
<211> LENGTH: 17
<212> TYPE: PRT
<213> ORGANISM: Rattus norvegicus

<400> SEQUENCE: 15

Leu Glu Ala Leu Pro Glu Gln Gln Asp Phe Leu Phe Asn Gln Asp Asn
1               5                   10                  15

Lys

<210> SEQ ID NO 16
<211> LENGTH: 20
<212> TYPE: DNA
<213> ORGANISM: Rattus norvegicus
<220> FEATURE:
<221> NAME/KEY: misc_feature
<222> LOCATION: (12)..(12)
<223> OTHER INFORMATION: a or g or c or t
<220> FEATURE:
<221> NAME/KEY: misc_feature
<222> LOCATION: (3)..(3)
<223> OTHER INFORMATION: modified_base
<220> FEATURE:
<221> NAME/KEY: modified_base
<222> LOCATION: (3)..(3)
<223> OTHER INFORMATION: I
<220> FEATURE:
<221> NAME/KEY: misc_feature
<222> LOCATION: (15)..(15)
<223> OTHER INFORMATION: a or g or c or t
<220> FEATURE:
<221> NAME/KEY: misc_feature
<222> LOCATION: (18)..(18)
<223> OTHER INFORMATION: a or g or c or t

<400> SEQUENCE: 16
tanccrtgrt tngcngcnac                                          20

<210> SEQ ID NO 17
<211> LENGTH: 20
```

```
<212> TYPE: DNA
<213> ORGANISM: Rattus norvegicus
<220> FEATURE:
<221> NAME/KEY: misc_feature
<222> LOCATION: (3)..(3)
<223> OTHER INFORMATION: a or g or c or t
<220> FEATURE:
<221> NAME/KEY: modified_base
<222> LOCATION: (18)..(18)
<223> OTHER INFORMATION: I
<220> FEATURE:
<221> NAME/KEY: misc_feature
<222> LOCATION: (18)..(18)
<223> OTHER INFORMATION: modified_base
<220> FEATURE:
<221> NAME/KEY: misc_feature
<222> LOCATION: (6)..(6)
<223> OTHER INFORMATION: a or g or c or t
<220> FEATURE:
<221> NAME/KEY: misc_feature
<222> LOCATION: (9)..(9)
<223> OTHER INFORMATION: a or g or c or t

<400> SEQUENCE: 17
gtngcngcna aycayggnta                                              20

<210> SEQ ID NO 18
<211> LENGTH: 20
<212> TYPE: DNA
<213> ORGANISM: Rattus norvegicus
<220> FEATURE:
<221> NAME/KEY: misc_feature
<222> LOCATION: (9)..(9)
<223> OTHER INFORMATION: a or g or c or t
<220> FEATURE:
<221> NAME/KEY: misc_feature
<222> LOCATION: (6)..(6)
<223> OTHER INFORMATION: modified_base
<220> FEATURE:
<221> NAME/KEY: modified_base
<222> LOCATION: (6)..(6)
<223> OTHER INFORMATION: I
<220> FEATURE:
<221> NAME/KEY: misc_feature
<222> LOCATION: (12)..(12)
<223> OTHER INFORMATION: a or g or c or t
<220> FEATURE:
<221> NAME/KEY: misc_feature
<222> LOCATION: (18)..(18)
<223> OTHER INFORMATION: a or g or c or t

<400> SEQUENCE: 18
gcrtangtng tnggrtangc                                              20

<210> SEQ ID NO 19
<211> LENGTH: 21
<212> TYPE: DNA
<213> ORGANISM: Rattus norvegicus

<400> SEQUENCE: 19
ctccaaacac gggttgattt c                                            21

<210> SEQ ID NO 20
<211> LENGTH: 21
<212> TYPE: DNA
<213> ORGANISM: Rattus norvegicus

<400> SEQUENCE: 20
tggggtggtt cttttacagt c                                            21

<210> SEQ ID NO 21
```

```
<211> LENGTH: 30
<212> TYPE: DNA
<213> ORGANISM: Rattus norvegicus

<400> SEQUENCE: 21
tggtggaatt ctttaccaag tctactcacc                                       30

<210> SEQ ID NO 22
<211> LENGTH: 21
<212> TYPE: DNA
<213> ORGANISM: Rattus norvegicus

<400> SEQUENCE: 22
ctccaaacac ggattaattt c                                                21

<210> SEQ ID NO 23
<211> LENGTH: 21
<212> TYPE: DNA
<213> ORGANISM: Rattus norvegicus

<400> SEQUENCE: 23
gaaattaatc cgtgtttgga g                                                21

<210> SEQ ID NO 24
<211> LENGTH: 4576
<212> TYPE: DNA
<213> ORGANISM: Homo sapiens

<400> SEQUENCE: 24
attcaatata atctggcgaa tgcaattgag gctgccgatg cctacacagt gtttgctcca      60
aacaacaatg ccatcgagaa ttacatcagg gagaagaaag tcttgtctct agaggaggac     120
gtcctccggt atcatgtggt cctggaggag aaactcctga agaatgacct gcacaatggc     180
atgcatcgtg agaccatgct gggtttctcc tatttcctta gcttctttct ccataatgac     240
cagctctatg taaatgaggc tccaataaac tacaccaatg tagccactga taagggagtg     300
atccatggct tgggaaaagt tctggaaatt cagaagaaca gatgtgataa taatgacact     360
actattatac gaggaagatg taggacatgc tcctcagagc tgacctgccc attcggaact     420
aaatctctag gtaatgagaa gaggagatgc atctataccc tctatttcat gggaagacga     480 accctgtttta ttgggtgcca gccaaaatgt gtgagaaccg tcattacgag agaatgctgt     540
gccggcttct ttggcccccca atgccagccc tgtccaggga tgcccagaa tgtctgcttt     600 ggtaatggca tctgtttgga tggagtgaat ggcacaggtg tgtgtgagtg tggggagggc     660
ttcagcggca cagcctgcga gacctgcacc gagggcaagt acggcatcca ctgtgaccaa     720
gcatgttctt gtgtccatgg agatgcaac caaggaccct gggagatgg ctcctgtgac     780 tgtgatgttg ctggcgagg agtgcattgt gacaatgcaa ccacagaaga caactgcaat     840
gggacatgcc ataccagcgc caactgcctc accaactcag atggtacagc ttcatgcaag     900
tgtgcagcag gattccaagg aaacgggacc atctgcacag caatcaatgc ctgtgagatc     960
agcaatggag gttgctctgc caaggctgac tgtaagagaa ccaccccagg aaggcgagtg    1020
tgcacgtgca aagcaggcta cacgggtgat ggcattgtgt gcctggaaat caacccgtgt    1080
ttggagaacc atggtggctg tgacaagaat gcggagtgca cacagacagg acccaaccag    1140
gctgcctgta actgtttgcc agcatacact ggagatggaa aggtctgcac actcatcaat    1200
gtctgcttaa ctaaaaatgg cggctgtagt gaatttgcca tctgcaacca cactgggcaa    1260
gtagaaagga cttgtacttg caagccaaac tacattggag atggatttac ctgccgcggc    1320
```

```
agcatttatc aggagcttcc caagaacccg aaaacttccc agtatttctt ccagttgcag   1380
gagcatttcg tgaaagatct ggtcggccca ggccccttca ctgttttttgc acctttatct  1440 gcagcctttg atgaggaagc tcgggttaaa gactgggaca atacggttt aatgccccag    1500 gttcttcggt accatgtggt cgcctgccac cagctgcttc tggaaaacct gaaattgatc   1560
tcaaatgcta cttccctcca aggagagcca atagtcatct ccgtctctca gagcacggtg   1620
tatataaaca ataaggctaa gatcatatcc agtgatatca tcagtactaa tgggattgtt   1680
catatcatag acaaattgct atctcccaaa aatttgctta tcactcccaa agacaactct   1740
ggaagaattc tgcaaaatct tacgactttg gcaacaaaca atggctacat caaatttagc   1800
aacttaatac aggactcagg tttgctgagt gtcatcaccg atcccatcca caccccagtc   1860
actctcttct ggcccaccga ccaagccctc catgccctac ctgctgaaca acaggacttc   1920
ctgttcaacc aagacaacaa ggacaagctg aaggagtatt tgaagtttca tgtgatacga   1980
gatgccaagg ttttagctgt ggatcttccc acatccactg cctggaagac cctgcaaggt   2040
tcagagctga gtgtgaaatg tggagctggc agggacatcg tgacctctt tctgaatggc    2100 caaacctgca gaattgtgca gcgggagctc ttgtttgacc tgggtgtggc ctacggcatt   2160
gactgtctgc tgattgatcc caccctgggg ggccgctgtg acacctttac tactttcgat   2220
gcctcggggg agtgtgggag ctgtgtcaat actcccagct gcccaaggtg gagtaaacca   2280
aagggtgtga agcagaagtg tctctacaac ctgcccttca gaggaacct ggaaggctgc    2340 cgggagcggt gcagcctggt gatacagatc cccaggtgct gcaagggcta cttcgggcga   2400
gactgtcagg cctgccctgg aggaccagat gccccgtgta ataaccgggg tgtctgcctt   2460
gatcagtact cggccaccgg agagtgtaaa tgcaacaccg gcttcaatgg acggcgtgt    2520 gagatgtgct ggccggggag atttgggcct gattgtctgc cctgtggctg ctcagaccac   2580
ggacagtgcg atgatggcat cacgggctcc ggcagtgcc tctgtgaaac ggggtggaca   2640
ggcccctcgt gtgacactca ggcagttttg cctgcagtgt gtacgcctcc ttgttctgct   2700
catgccacct gtaaggagaa caacacgtgt gagtgtaacc tggattatga aggtgacgga   2760
atcacatgca cagttgtgga tttctgcaaa caggacaacg ggggctgtgc aaaggtggcc   2820
agatgctccc agaagggcac gaaggtctcc tgcagctgcc agaagggata caaaggggac   2880
gggcacagct gcacagagat agacccctgt gcagacggcc ttaacggagg tgtcacgag    2940 cacgccacct gtaagatgac aggcccgggc aagcacaagt gtgagtgtaa aagtcactat   3000
gtcggagatg ggctgaactg tgagccggag cagctgccca ttgaccgctg cttacaggac   3060
aatgggcagt gccatgcaga cgccaaatgt gtcgacctcc acttccagga taccactgtt   3120
ggggtgttcc atctacgctc cccactgggc cagtataagc tgacctttga caaagccaga   3180
gaggcctgtg ccaacgaagc tgcgaccatg gcaacctaca accagctctc ctatgcccag   3240
aaggccaagt accacctgtg ctcagcaggc tggctggaga ccgggcgggt tgcctacccc   3300
acagccttcg cctcccagaa ctgtggctct ggtgtggttg ggatagtgga ctatggacct   3360
agacccaaca agagtgaaat gtgggatgtc ttctgctatc ggatgaaaga tgtgaactgc   3420
acctgcaagg tgggctatgt gggagatggc ttctcatgca gtgggaacct gctgcaggtc   3480
ctgatgtcct tcccctcact cacaaaactc ctgacggaag tgctggccta ttccaacagc   3540
tcagctcgag gccgtgcatt tctagaacac ctgactgacc tgtccatccg cggcacctc    3600 tttgtgccac agaacagtgg gctggggag aatgagacct tgtctgggcg ggacatcgag   3660
```

```
caccacctcg ccaatgtcag catgttttc tacaatgacc ttgtcaatgg caccaccctg    3720
caaacgaggc tgggaagcaa gctgctcatc actgccagcc aggacccact ccaaccgacg    3780
gagaccaggt ttgttgatgg aagagccatt ctgcagtggg acatctttgc ctccaatggg    3840
atcattcatg tcatttccag gcctttaaaa gcacccctg cccccgtgac cttgacccac    3900
actggcttgg gagcagggat cttctttgcc atcatcctgg tgactggggc tgttgccttg    3960
gctgcttact cctactttcg gataaaccgg agaacaatcg gcttccagca ttttgagtcg    4020
gaagaggaca ttaatgttgc agctcttggc aagcagcagc ctgagaatat ctcgaacccc    4080
ttgtatgaga gcacaacctc agctccccca gaaccttcct acgacccctt cacggactct    4140
gaagaacggc agcttgaggg caatgacccc ttgaggacac tgtgagggcc tggacgggag    4200
atgccagcca tcactcactg ccacctgggc atcaactgt gaattctcag caccagttgc    4260
cttttaggaa cgtaaagtcc tttaagcact cagaagccat acctcatctc tctggctgat    4320 ctggggttg tttctgtggg tgagagatgt gttgctgtgc ccacccagta cagcttcctc    4380
ctctgaccct ttggctcttc ttcctttgta ctcttcagct ggcacctgct ccattctgcc    4440
ctacatgatg ggtaactgtg atcttcttc cctgttagat tgtaagcctc cgtcttttgta   4500 tcccagcccc tagcccagtg cctgacacag gaactgtgca aataaaggt ttatggaaca    4560 gaaacaaagt caacag                                                     4576
```

<210> SEQ ID NO 25
<211> LENGTH: 1394
<212> TYPE: PRT
<213> ORGANISM: Homo sapiens

<400> SEQUENCE: 25

```
Ile Gln Tyr Asn Leu Ala Asn Ala Ile Glu Ala Ala Asp Ala Tyr Thr
 1               5                  10                  15

Val Phe Ala Pro Asn Asn Asn Ala Ile Glu Asn Tyr Ile Arg Glu Lys
            20                  25                  30

Lys Val Leu Ser Leu Glu Glu Asp Val Leu Arg Tyr His Val Val Leu
        35                  40                  45

Glu Glu Lys Leu Leu Lys Asn Asp Leu His Asn Gly Met His Arg Glu
    50                  55                  60

Thr Met Leu Gly Phe Ser Tyr Phe Leu Ser Phe Leu His Asn Asp
 65                  70                  75                  80

Gln Leu Tyr Val Asn Glu Ala Pro Ile Asn Tyr Thr Asn Val Ala Thr
                85                  90                  95

Asp Lys Gly Val Ile Gln Tyr Asn Leu Ala Asn Ala Ile Glu Ala Ala
            100                 105                 110

Asp Ala Tyr Thr Val Phe Ala Pro Asn Asn Asn Ala Ile Glu Asn Tyr
        115                 120                 125

Ile Arg Glu Lys Lys Val Leu Ser Leu Glu Glu Asp Val Leu Arg Tyr
    130                 135                 140

His Val Val Leu Glu Glu Lys Leu Leu Lys Asn Asp Leu His Asn Gly
145                 150                 155                 160

Met His Arg Glu Thr Met Leu Gly Phe Ser Tyr Phe Leu Ser Phe
                165                 170                 175

Leu His Asn Asp Gln Leu Tyr Val Asn Glu Ala Pro Ile Asn Tyr Thr
            180                 185                 190

Asn Val Ala Thr Asp Lys Gly Val Ile Gln Tyr Asn Leu Ala Asn Ala
        195                 200                 205
```

```
Ile Glu Ala Ala Asp Ala Tyr Thr Val Phe Ala Pro Asn Asn Asn Ala
210                 215                 220

Ile Glu Asn Tyr Ile Arg Glu Lys Lys Val Leu Ser Leu Glu Glu Asp
225                 230                 235                 240

Val Leu Arg Tyr His Val Val Leu Glu Glu Lys Leu Leu Lys Asn Asp
                245                 250                 255

Leu His Asn Gly Met His Arg Glu Thr Met Leu Gly Phe Ser Tyr Phe
            260                 265                 270

Leu Ser Phe Phe Leu His Asn Asp Gln Leu Tyr Val Asn Glu Ala Pro
        275                 280                 285

Ile Asn Tyr Thr Asn Val Ala Thr Asp Lys Gly Val Cys Ala Ala Gly
    290                 295                 300

Phe Gln Gly Asn Gly Thr Ile Cys Thr Ala Ile Asn Ala Cys Glu Ile
305                 310                 315                 320

Ser Asn Gly Gly Cys Ser Ala Lys Ala Asp Cys Lys Arg Thr Thr Pro
                325                 330                 335

Gly Arg Arg Val Cys Thr Cys Lys Ala Gly Tyr Thr Gly Asp Gly Ile
                340                 345                 350

Val Cys Leu Glu Ile Asn Pro Cys Leu Glu Asn His Gly Gly Cys Asp
            355                 360                 365

Lys Asn Ala Glu Cys Thr Gln Thr Gly Pro Asn Gln Ala Ala Cys Asn
370                 375                 380

Cys Leu Pro Ala Tyr Thr Gly Asp Gly Lys Val Cys Thr Leu Ile Asn
385                 390                 395                 400

Val Cys Leu Thr Lys Asn Gly Gly Cys Ser Glu Phe Ala Ile Cys Asn
                405                 410                 415

His Thr Gly Gln Val Glu Arg Thr Cys Thr Cys Lys Pro Asn Tyr Ile
            420                 425                 430

Gly Asp Gly Phe Thr Cys Arg Gly Ser Ile Tyr Gln Glu Leu Pro Lys
        435                 440                 445

Asn Pro Lys Thr Ser Gln Tyr Phe Gln Leu Gln Glu His Phe Val
    450                 455                 460

Lys Asp Leu Val Gly Pro Gly Pro Phe Thr Phe Ala Pro Leu Ser
465                 470                 475                 480

Ala Ala Phe Asp Glu Glu Ala Arg Val Lys Asp Trp Asp Lys Tyr Gly
                485                 490                 495

Leu Met Pro Gln Val Leu Arg Tyr His Val Val Ala Cys His Gln Leu
            500                 505                 510

Leu Leu Glu Asn Leu Lys Leu Ile Ser Asn Ala Thr Ser Leu Gln Gly
        515                 520                 525

Glu Pro Ile Val Ile Ser Val Ser Gln Ser Thr Val Tyr Ile Asn Asn
    530                 535                 540

Lys Ala Lys Ile Ile Ser Ser Asp Ile Ser Thr Asn Gly Ile Val
545                 550                 555                 560

His Ile Ile Asp Lys Leu Leu Ser Pro Lys Asn Leu Leu Ile Thr Pro
                565                 570                 575

Lys Asp Asn Ser Gly Arg Ile Leu Gln Asn Leu Thr Thr Leu Ala Thr
            580                 585                 590

Asn Asn Gly Tyr Ile Lys Phe Ser Asn Leu Ile Gln Asp Ser Gly Leu
        595                 600                 605

Leu Ser Val Ile Thr Asp Pro Ile His Thr Pro Val Thr Leu Phe Trp
    610                 615                 620

Pro Thr Asp Gln Ala Leu His Ala Leu Pro Ala Glu Gln Gln Asp Phe
```

-continued

```
            625                 630                 635                 640
Leu Phe Asn Gln Asp Asn Lys Asp Lys Leu Lys Glu Tyr Leu Lys Phe
                    645                 650                 655
His Val Ile Arg Asp Ala Lys Val Leu Ala Val Asp Leu Pro Thr Ser
                    660                 665                 670
Thr Ala Trp Lys Thr Leu Gln Gly Ser Glu Leu Ser Val Lys Cys Gly
                    675                 680                 685
Ala Gly Arg Asp Ile Gly Asp Leu Phe Leu Asn Gly Gln Thr Cys Arg
                    690                 695                 700
Ile Val Gln Arg Glu Leu Leu Phe Asp Leu Gly Val Ala Tyr Gly Ile
705                 710                 715                 720
Asp Cys Leu Leu Ile Asp Pro Thr Leu Gly Gly Arg Cys Asp Thr Phe
                    725                 730                 735
Thr Thr Phe Asp Ala Ser Gly Glu Cys Gly Ser Cys Val Asn Thr Pro
                    740                 745                 750
Ser Cys Pro Arg Trp Ser Lys Pro Lys Gly Val Lys Gln Lys Cys Leu
                    755                 760                 765
Tyr Asn Leu Pro Phe Lys Arg Asn Leu Glu Gly Cys Arg Glu Arg Cys
                    770                 775                 780
Ser Leu Val Ile Gln Ile Pro Arg Cys Cys Lys Gly Tyr Phe Gly Arg
785                 790                 795                 800
Asp Cys Gln Ala Cys Pro Gly Gly Pro Asp Ala Pro Cys Asn Asn Arg
                    805                 810                 815
Gly Val Cys Leu Asp Gln Tyr Ser Ala Thr Gly Glu Cys Lys Cys Asn
                    820                 825                 830
Thr Gly Phe Asn Gly Thr Ala Cys Glu Met Cys Trp Pro Gly Arg Phe
                    835                 840                 845
Gly Pro Asp Cys Leu Pro Cys Gly Cys Ser Asp His Gly Gln Cys Asp
                    850                 855                 860
Asp Gly Ile Thr Gly Ser Gly Gln Cys Leu Cys Glu Thr Gly Trp Thr
865                 870                 875                 880
Gly Pro Ser Cys Asp Thr Gln Ala Val Leu Pro Ala Val Cys Thr Pro
                    885                 890                 895
Pro Cys Ser Ala His Ala Thr Cys Lys Glu Asn Asn Thr Cys Glu Cys
                    900                 905                 910
Asn Leu Asp Tyr Glu Gly Asp Gly Ile Thr Cys Thr Val Val Asp Phe
                    915                 920                 925
Cys Lys Gln Asp Asn Gly Gly Cys Ala Lys Val Ala Arg Cys Ser Gln
                    930                 935                 940
Lys Gly Thr Lys Val Ser Cys Ser Cys Gln Lys Gly Tyr Lys Gly Asp
945                 950                 955                 960
Gly His Ser Cys Thr Glu Ile Asp Pro Cys Ala Asp Gly Leu Asn Gly
                    965                 970                 975
Gly Cys His Glu His Ala Thr Cys Lys Met Thr Gly Pro Gly Lys His
                    980                 985                 990
Lys Cys Glu Cys Lys Ser His Tyr  Val Gly Asp Gly Leu  Asn Cys Glu
                    995                 1000                1005
Pro Glu  Gln Leu Pro Ile Asp  Arg Cys Leu Gln Asp  Asn Gly Gln
        1010                1015                1020
Cys His  Ala Asp Ala Lys Cys  Val Asp Leu His Phe  Gln Asp Thr
        1025                1030                1035
Thr Val  Gly Val Phe His Leu  Arg Ser Pro Leu Gly  Gln Tyr Lys
        1040                1045                1050
```

Leu Thr Phe Asp Lys Ala Arg Glu Ala Cys Ala Asn Glu Ala Ala
    1055                1060                1065

Thr Met Ala Thr Tyr Asn Gln Leu Ser Tyr Ala Gln Lys Ala Lys
    1070                1075                1080

Tyr His Leu Cys Ser Ala Gly Trp Leu Glu Thr Gly Arg Val Ala
    1085                1090                1095

Tyr Pro Thr Ala Phe Ala Ser Gln Asn Cys Gly Ser Gly Val Val
    1100                1105                1110

Gly Ile Val Asp Tyr Gly Pro Arg Pro Asn Lys Ser Glu Met Trp
    1115                1120                1125

Asp Val Phe Cys Tyr Arg Met Lys Asp Val Asn Cys Thr Cys Lys
    1130                1135                1140

Val Gly Tyr Val Gly Asp Gly Phe Ser Cys Ser Gly Asn Leu Leu
    1145                1150                1155

Gln Val Leu Met Ser Phe Pro Ser Leu Thr Asn Phe Leu Thr Glu
    1160                1165                1170

Val Leu Ala Tyr Ser Asn Ser Ser Ala Arg Gly Arg Ala Phe Leu
    1175                1180                1185

Glu His Leu Thr Asp Leu Ser Ile Arg Gly Thr Leu Phe Val Pro
    1190                1195                1200

Gln Asn Ser Gly Leu Gly Glu Asn Glu Thr Leu Ser Gly Arg Asp
    1205                1210                1215

Ile Glu His His Leu Ala Asn Val Ser Met Phe Phe Tyr Asn Asp
    1220                1225                1230

Leu Val Asn Gly Thr Thr Leu Gln Thr Arg Leu Gly Ser Lys Leu
    1235                1240                1245

Leu Ile Thr Ala Ser Gln Asp Pro Leu Gln Pro Thr Glu Thr Arg
    1250                1255                1260

Phe Val Asp Gly Arg Ala Ile Leu Gln Trp Asp Ile Phe Ala Ser
    1265                1270                1275

Asn Gly Ile Ile His Val Ile Ser Arg Pro Leu Lys Ala Pro Pro
    1280                1285                1290

Ala Pro Val Thr Leu Thr His Thr Gly Leu Gly Ala Gly Ile Phe
    1295                1300                1305

Phe Ala Ile Ile Leu Val Thr Gly Ala Val Ala Leu Ala Ala Tyr
    1310                1315                1320

Ser Tyr Phe Arg Ile Asn Arg Arg Thr Ile Gly Phe Gln His Phe
    1325                1330                1335

Glu Ser Glu Glu Asp Ile Asn Val Ala Ala Leu Gly Lys Gln Gln
    1340                1345                1350

Pro Glu Asn Ile Ser Asn Pro Leu Tyr Glu Ser Thr Thr Ser Ala
    1355                1360                1365

Pro Pro Glu Pro Ser Tyr Asp Pro Phe Thr Asp Ser Glu Glu Arg
    1370                1375                1380

Gln Leu Glu Gly Asn Asp Pro Leu Arg Thr Leu
    1385                1390

<210> SEQ ID NO 26
<211> LENGTH: 21
<212> TYPE: DNA
<213> ORGANISM: Homo sapiens

<400> SEQUENCE: 26
atgaggaagc tcgggttaaa g                                              21

```
<210> SEQ ID NO 27
<211> LENGTH: 18
<212> TYPE: PRT
<213> ORGANISM: Rattus norvegicus

<400> SEQUENCE: 27

Ser Leu Pro Ser Leu Leu Thr Arg Leu Glu Gln Met Pro Asp Tyr Ser
1               5                   10                  15

Ile Phe

<210> SEQ ID NO 28
<211> LENGTH: 17
<212> TYPE: PRT
<213> ORGANISM: Rattus norvegicus
<220> FEATURE:
<221> NAME/KEY: MISC_FEATURE
<222> LOCATION: (12)..(12)
<223> OTHER INFORMATION: UNKNOWN
<220> FEATURE:
<221> NAME/KEY: MISC_FEATURE
<222> LOCATION: (1)..(1)
<223> OTHER INFORMATION: UNKNOWN
<220> FEATURE:
<221> NAME/KEY: MISC_FEATURE
<222> LOCATION: (2)..(2)
<223> OTHER INFORMATION: UNKNOWN
<220> FEATURE:
<221> NAME/KEY: MISC_FEATURE
<222> LOCATION: (11)..(11)
<223> OTHER INFORMATION: UNKNOWN

<400> SEQUENCE: 28

Xaa Xaa Val Ile His Gly Leu Glu Lys Val Xaa Xaa Ile Gln Lys Asn
1               5                   10                  15

Arg

<210> SEQ ID NO 29
<211> LENGTH: 24
<212> TYPE: DNA
<213> ORGANISM: Homo sapiens

<400> SEQUENCE: 29
gatgtagcca ttgtttgttg ccaa                                          24

<210> SEQ ID NO 30
<211> LENGTH: 24
<212> TYPE: DNA
<213> ORGANISM: Homo sapiens

<400> SEQUENCE: 30
agacgccaaa tgtgtcgacc tcca                                          24

<210> SEQ ID NO 31
<211> LENGTH: 24
<212> TYPE: DNA
<213> ORGANISM: Homo sapiens

<400> SEQUENCE: 31
gaataggcca gcacttccgt cagg                                          24

<210> SEQ ID NO 32
<211> LENGTH: 24
<212> TYPE: DNA
<213> ORGANISM: Homo sapiens
```

<400> SEQUENCE: 32
ggtgaggcag ttggcgctgg tatg                                              24

<210> SEQ ID NO 33
<211> LENGTH: 24
<212> TYPE: DNA
<213> ORGANISM: Homo sapiens

<400> SEQUENCE: 33
gagctgacct gcccattcgg aact                                              24

<210> SEQ ID NO 34
<211> LENGTH: 24
<212> TYPE: DNA
<213> ORGANISM: Homo sapiens

<400> SEQUENCE: 34
cataccagcg ccaactgcct cacc                                              24

<210> SEQ ID NO 35
<211> LENGTH: 21
<212> TYPE: DNA
<213> ORGANISM: Homo sapiens

<400> SEQUENCE: 35
ctttaacccg agcttcctca t                                                 21

<210> SEQ ID NO 36
<211> LENGTH: 24
<212> TYPE: DNA
<213> ORGANISM: Homo sapiens

<400> SEQUENCE: 36
caagtacggc atccactgtg acca                                              24

<210> SEQ ID NO 37
<211> LENGTH: 24
<212> TYPE: DNA
<213> ORGANISM: Homo sapiens

<400> SEQUENCE: 37
ggctacttcg ggcgagactg tcag                                              24

<210> SEQ ID NO 38
<211> LENGTH: 24
<212> TYPE: DNA
<213> ORGANISM: Homo sapiens

<400> SEQUENCE: 38
ctgacagtct cgcccgaagt agcc                                              24

<210> SEQ ID NO 39
<211> LENGTH: 21
<212> TYPE: DNA
<213> ORGANISM: Homo sapiens

<400> SEQUENCE: 39
ttgtactctt cagctggcac c                                                 21

<210> SEQ ID NO 40
<211> LENGTH: 5
<212> TYPE: PRT
<213> ORGANISM: Homo sapiens

```
<220> FEATURE:
<221> NAME/KEY: MISC_FEATURE
<222> LOCATION: (1)..(1)
<223> OTHER INFORMATION: unknown

<400> SEQUENCE: 40

Xaa Ser Lys Pro Lys
1               5

<210> SEQ ID NO 41
<211> LENGTH: 5
<212> TYPE: PRT
<213> ORGANISM: Homo sapiens

<400> SEQUENCE: 41

Leu Thr Phe Asp Lys
1               5

<210> SEQ ID NO 42
<211> LENGTH: 9
<212> TYPE: PRT
<213> ORGANISM: Homo sapiens

<400> SEQUENCE: 42

Gly Ser Ile Tyr Gln Glu Leu Pro Lys
1               5

<210> SEQ ID NO 43
<211> LENGTH: 13
<212> TYPE: PRT
<213> ORGANISM: Homo sapiens

<400> SEQUENCE: 43

Gly Thr Leu Phe Val Pro Gln Asn Ser Gly Leu Gly Glu
1               5                   10

<210> SEQ ID NO 44
<211> LENGTH: 23
<212> TYPE: PRT
<213> ORGANISM: Homo sapiens

<400> SEQUENCE: 44

Asp Leu Val Gly Pro Gly Pro Phe Thr Val Phe Ala Pro Leu Ser Ala
1               5                   10                  15

Ala Phe Asp Glu Glu Ala Arg
                20

<210> SEQ ID NO 45
<211> LENGTH: 9
<212> TYPE: PRT
<213> ORGANISM: Homo sapiens

<400> SEQUENCE: 45

Glu Leu Thr Ser Pro Phe Gly Thr Lys
1               5

<210> SEQ ID NO 46
<211> LENGTH: 6
<212> TYPE: PRT
<213> ORGANISM: Homo sapiens

<400> SEQUENCE: 46

Met Pro Gln Val Leu Arg
1               5
```

```
<210> SEQ ID NO 47
<211> LENGTH: 7
<212> TYPE: PRT
<213> ORGANISM: Homo sapiens

<400> SEQUENCE: 47

Ser Pro Leu Gly Gln Tyr Lys
1               5

<210> SEQ ID NO 48
<211> LENGTH: 6
<212> TYPE: PRT
<213> ORGANISM: Homo sapiens

<400> SEQUENCE: 48

Val Leu Glu Ile Gln Lys
1               5

<210> SEQ ID NO 49
<211> LENGTH: 7
<212> TYPE: PRT
<213> ORGANISM: Homo sapiens

<400> SEQUENCE: 49

Val Ile His Gly Leu Gly Lys
1               5

<210> SEQ ID NO 50
<211> LENGTH: 6
<212> TYPE: PRT
<213> ORGANISM: Homo sapiens

<400> SEQUENCE: 50

Lys Gly Tyr Phe Gly Arg
1               5

<210> SEQ ID NO 51
<211> LENGTH: 6
<212> TYPE: PRT
<213> ORGANISM: Homo sapiens

<400> SEQUENCE: 51

Lys Phe His Val Ile Arg
1               5

<210> SEQ ID NO 52
<211> LENGTH: 8
<212> TYPE: PRT
<213> ORGANISM: Homo sapiens

<400> SEQUENCE: 52

Arg Ser Pro Leu Gly Gln Tyr Lys
1               5

<210> SEQ ID NO 53
<211> LENGTH: 10
<212> TYPE: PRT
<213> ORGANISM: Homo sapiens

<400> SEQUENCE: 53

Arg Gly Ser Ile Tyr Gln Glu Leu Pro Lys
1               5                   10

<210> SEQ ID NO 54
```

-continued

```
<211> LENGTH: 11
<212> TYPE: PRT
<213> ORGANISM: Homo sapiens

<400> SEQUENCE: 54

Lys Thr Leu Gln Gly Ser Glu Leu Ser Val Lys
1               5                   10

<210> SEQ ID NO 55
<211> LENGTH: 15
<212> TYPE: PRT
<213> ORGANISM: Homo sapiens

<400> SEQUENCE: 55

Arg Ser Pro Leu Gly Gln Tyr Lys Leu Thr Phe Asp Lys Ala Arg
1               5                   10                  15

<210> SEQ ID NO 56
<211> LENGTH: 10
<212> TYPE: PRT
<213> ORGANISM: Homo sapiens

<400> SEQUENCE: 56

Lys Tyr Gly Leu Met Pro Gln Val Leu Arg
1               5                   10
```